(12) United States Patent
Kshirsagar et al.

(10) Patent No.: US 8,343,993 B2
(45) Date of Patent: Jan. 1, 2013

(54) HYDROXYALKYL SUBSTITUTED IMIDAZONAPHTHYRIDINES

(75) Inventors: Tushar A. Kshirsagar, Woodbury, MN (US); Scott E. Langer, Woodbury, MN (US); Shri Niwas, Maple Grove, MN (US); George W. Griesgraber, Eagan, MN (US); Philip D. Heppner, Forest Lake, MN (US); Kyle J. Lindstrom, Houlton, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 807 days.

(21) Appl. No.: 11/885,007

(22) PCT Filed: Feb. 22, 2006

(86) PCT No.: PCT/US2006/006043
§ 371 (c)(1),
(2), (4) Date: Jun. 16, 2009

(87) PCT Pub. No.: WO2006/091568
PCT Pub. Date: Aug. 31, 2006

(65) Prior Publication Data
US 2009/0253695 A1 Oct. 8, 2009

Related U.S. Application Data

(60) Provisional application No. 60/655,508, filed on Feb. 23, 2005.

(51) Int. Cl.
*A61K 31/4375* (2006.01)
*C07D 513/16* (2006.01)
(52) U.S. Cl. .............. 514/290; 546/80; 546/81
(58) Field of Classification Search ............ 546/80, 546/81; 514/290
See application file for complete search history.

(56) References Cited

U.S. PATENT DOCUMENTS

| | | |
|---|---|---|
| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,444,065 A | 8/1995 | Nikolaides et al. |
| 5,446,153 A | 8/1995 | Lindstrom et al. |
| 5,482,936 A | 1/1996 | Lindstrom |
| 5,494,916 A | 2/1996 | Lindstrom et al. |
| 5,525,612 A | 6/1996 | Gerster |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,741,908 A | 4/1998 | Gerster et al. |
| 5,756,747 A | 5/1998 | Gerster et al. |
| 5,886,006 A | 3/1999 | Nikolaides et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 * | 2/2001 | Gerster et al. ............... 514/293 |
| 6,200,592 B1 | 3/2001 | Tomai et al. |
| 6,245,776 B1 | 6/2001 | Skwierczynski et al. |
| 6,331,539 B1 | 12/2001 | Crooks et al. |
| 6,365,166 B2 | 4/2002 | Beaurline et al. |
| 6,376,669 B1 | 4/2002 | Rice et al. |
| 6,440,992 B1 | 8/2002 | Gerster et al. |
| 6,451,810 B1 | 9/2002 | Coleman et al. |
| 6,486,168 B1 | 11/2002 | Skwierczynski et al. |
| 6,514,985 B1 * | 2/2003 | Gerster et al. ............... 514/293 |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,610,319 B2 | 8/2003 | Tomai et al. |
| 6,627,638 B2 | 9/2003 | Gerster et al. |
| 6,627,640 B2 | 9/2003 | Gerster et al. |
| 6,630,588 B2 | 10/2003 | Rice et al. |
| 6,638,944 B2 * | 10/2003 | Mickelson ............... 514/293 |
| 6,656,938 B2 | 12/2003 | Crooks et al. |
| 6,660,735 B2 | 12/2003 | Crooks et al. |
| 6,660,747 B2 | 12/2003 | Crooks et al. |

(Continued)

FOREIGN PATENT DOCUMENTS

| | | |
|---|---|---|
| WO | WO 99/29693 A1 | 6/1999 |
| WO | WO 03/045391 A1 | 6/2003 |
| WO | WO 2005/051324 A3 | 6/2005 |

OTHER PUBLICATIONS

Dorwald F. A. Side Reactions in Organic Synthesis, 2005, Wiley: VCH, Weinheim p. IX of Preface.*

*Primary Examiner* — Rita Desai

(57) ABSTRACT

Certain imidazonaphthyridines with a hydroxymethyl or hydroxyethyl substituent at the 2-position, pharmaceutical compositions containing the compounds, intermediates, methods of making and methods of use of these compounds as immunomodulators, for preferentially inducing IFN-α biosynthesis in animals and in the treatment of diseases including viral and neoplastic diseases are disclosed.

18 Claims, 1 Drawing Sheet

U.S. PATENT DOCUMENTS

| | | | |
|---|---|---|---|
| 6,664,260 | B2 | 12/2003 | Charles et al. |
| 6,664,264 | B2 | 12/2003 | Dellaria et al. |
| 6,664,265 | B2 | 12/2003 | Crooks et al. |
| 6,667,312 | B2 | 12/2003 | Bonk et al. |
| 6,670,372 | B2 | 12/2003 | Charles et al. |
| 6,677,347 | B2 | 1/2004 | Crooks et al. |
| 6,677,348 | B2 | 1/2004 | Heppner et al. |
| 6,677,349 | B1 | 1/2004 | Griesgraber |
| 6,683,088 | B2 | 1/2004 | Crooks et al. |
| 6,696,076 | B2 | 2/2004 | Tomai et al. |
| 6,696,465 | B2 | 2/2004 | Dellaria et al. |
| 6,703,402 | B2 | 3/2004 | Gerster et al. |
| 6,706,728 | B2 | 3/2004 | Hedenstrom et al. |
| 6,716,988 | B2 | 4/2004 | Dellaria et al. |
| 6,720,333 | B2 | 4/2004 | Dellaria et al. |
| 6,720,334 | B2 | 4/2004 | Dellaria et al. |
| 6,720,422 | B2 | 4/2004 | Dellaria et al. |
| 6,743,920 | B2 | 6/2004 | Lindstrom et al. |
| 6,756,382 | B2 | 6/2004 | Coleman et al. |
| 6,797,718 | B2 | 9/2004 | Dellaria et al. |
| 6,800,624 | B2 | 10/2004 | Crooks et al. |
| 6,809,203 | B2 | 10/2004 | Gerster et al. |
| 6,818,650 | B2 | 11/2004 | Griesgraber |
| 6,825,350 | B2 | 11/2004 | Crooks et al. |
| 6,841,678 | B2 | 1/2005 | Merli et al. |
| 6,852,861 | B2 | 2/2005 | Merli et al. |
| 6,878,719 | B2 | 4/2005 | Lindstrom et al. |
| 6,888,000 | B2 | 5/2005 | Crooks et al. |
| 6,894,060 | B2 | 5/2005 | Slade |
| 6,897,221 | B2 | 5/2005 | Crooks et al. |
| 6,903,113 | B2 | 6/2005 | Heppner et al. |
| 6,916,925 | B1 | 7/2005 | Rice et al. |
| 6,921,826 | B2 | 7/2005 | Dellaria et al. |
| 6,924,293 | B2 | 8/2005 | Lindstrom |
| 6,943,225 | B2 | 9/2005 | Lee et al. |
| 6,949,649 | B2 | 9/2005 | Bonk et al. |
| 6,953,804 | B2 | 10/2005 | Dellaria et al. |
| 6,969,722 | B2 | 11/2005 | Heppner et al. |
| 6,989,389 | B2 | 1/2006 | Heppner et al. |
| 7,030,129 | B2 | 4/2006 | Miller et al. |
| 7,030,131 | B2 | 4/2006 | Crooks et al. |
| 7,038,053 | B2 | 5/2006 | Lindstrom et al. |
| 7,049,439 | B2 | 5/2006 | Crooks et al. |
| 7,078,523 | B2 | 7/2006 | Crooks et al. |
| 7,091,214 | B2 | 8/2006 | Hays et al. |
| 7,098,221 | B2 | 8/2006 | Heppner et al. |
| 7,112,677 | B2 | 9/2006 | Griesgraber |
| 7,115,622 | B2 | 10/2006 | Crooks et al. |
| 7,125,890 | B2 | 10/2006 | Dellaria et al. |
| 7,132,429 | B2 | 11/2006 | Griesgraber et al. |
| 7,132,438 | B2 | 11/2006 | Frenkel et al. |
| 7,148,232 | B2 | 12/2006 | Gerster et al. |
| 7,157,453 | B2 | 1/2007 | Crooks et al. |
| 7,163,947 | B2 | 1/2007 | Griesgraber et al. |
| 7,179,253 | B2 | 2/2007 | Graham et al. |
| 7,199,131 | B2 | 4/2007 | Lindstrom |
| 7,214,675 | B2 | 5/2007 | Griesgraber |
| 7,220,758 | B2 | 5/2007 | Dellaria et al. |
| 7,226,928 | B2 | 6/2007 | Mitra et al. |
| 7,276,515 | B2 | 10/2007 | Dellaria et al. |
| 7,288,550 | B2 | 10/2007 | Dellaria et al. |
| 7,301,027 | B2 | 11/2007 | Colombo et al. |
| 7,375,180 | B2 | 5/2008 | Gorden et al. |
| 7,387,271 | B2 | 6/2008 | Noelle et al. |
| 7,393,859 | B2 | 7/2008 | Coleman et al. |
| 7,427,629 | B2 | 9/2008 | Kedl et al. |
| 7,485,432 | B2 | 2/2009 | Fink et al. |
| 7,544,697 | B2 | 6/2009 | Hays et al. |
| 7,576,068 | B2 | 8/2009 | Averett |
| 7,578,170 | B2 | 8/2009 | Mayer et al. |
| 7,579,359 | B2 | 8/2009 | Krepski et al. |
| 7,598,382 | B2 | 10/2009 | Hays et al. |
| 7,612,083 | B2 | 11/2009 | Griesgraber |
| 7,648,997 | B2 | 1/2010 | Kshirsagar et al. |
| 7,655,672 | B2 | 2/2010 | Statham et al. |
| 7,687,628 | B2 | 3/2010 | Gutman et al. |
| 7,696,159 | B2 | 4/2010 | Owens et al. |
| 7,699,057 | B2 | 4/2010 | Miller et al. |
| 7,731,967 | B2 | 6/2010 | O'Hagan et al. |
| 7,799,800 | B2 * | 9/2010 | Wightman ............... 514/303 |
| 7,879,849 | B2 | 2/2011 | Hays et al. |
| 7,884,207 | B2 | 2/2011 | Stoermer et al. |
| 7,888,349 | B2 | 2/2011 | Kshirsagar et al. |
| 7,897,597 | B2 | 3/2011 | Lindstrom et al. |
| 7,897,609 | B2 | 3/2011 | Niwas et al. |
| 7,897,767 | B2 | 3/2011 | Kshirsagar et al. |
| 7,902,209 | B2 | 3/2011 | Statham et al. |
| 7,902,210 | B2 | 3/2011 | Statham et al. |
| 7,902,211 | B2 | 3/2011 | Statham et al. |
| 7,902,212 | B2 | 3/2011 | Statham et al. |
| 7,902,213 | B2 | 3/2011 | Statham et al. |
| 7,902,214 | B2 | 3/2011 | Statham et al. |
| 7,902,215 | B2 | 3/2011 | Statham et al. |
| 7,902,216 | B2 | 3/2011 | Statham et al. |
| 7,902,242 | B2 | 3/2011 | Statham et al. |
| 7,902,243 | B2 | 3/2011 | Statham et al. |
| 7,902,244 | B2 | 3/2011 | Statham et al. |
| 7,902,245 | B2 | 3/2011 | Statham et al. |
| 7,902,246 | B2 | 3/2011 | Statham et al. |
| 7,915,281 | B2 * | 3/2011 | Moser et al. ............ 514/293 |
| 7,939,526 | B2 * | 5/2011 | Radmer et al. .......... 514/229.8 |
| 7,968,562 | B2 | 6/2011 | Skwierczynski et al. |
| 7,968,563 | B2 | 6/2011 | Kshirsagar et al. |
| 7,993,659 | B2 | 8/2011 | Noelle et al. |
| 8,017,779 | B2 | 9/2011 | Merrill et al. |
| 8,026,366 | B2 | 9/2011 | Prince et al. |
| 2002/0055517 | A1 | 5/2002 | Smith |
| 2002/0058674 | A1 | 5/2002 | Hedenstrom et al. |
| 2002/0107262 | A1 | 8/2002 | Lindstrom |
| 2003/0133913 | A1 | 7/2003 | Tomai et al. |
| 2003/0139364 | A1 | 7/2003 | Krieg et al. |
| 2004/0014779 | A1 | 1/2004 | Gorden et al. |
| 2004/0132079 | A1 | 7/2004 | Gupta et al. |
| 2004/0175336 | A1 | 9/2004 | Egging et al. |
| 2004/0180919 | A1 | 9/2004 | Lee et al. |
| 2004/0191833 | A1 | 9/2004 | Fink et al. |
| 2004/0197865 | A1 | 10/2004 | Gupta et al. |
| 2004/0202720 | A1 | 10/2004 | Wightman et al. |
| 2004/0214851 | A1 | 10/2004 | Birmachu et al. |
| 2004/0258698 | A1 | 12/2004 | Wightman et al. |
| 2004/0265351 | A1 | 12/2004 | Miller et al. |
| 2005/0048072 | A1 | 3/2005 | Kedl et al. |
| 2005/0059072 | A1 | 3/2005 | Birmachu et al. |
| 2005/0070460 | A1 | 3/2005 | Hammerbeck et al. |
| 2005/0096259 | A1 | 5/2005 | Tomai et al. |
| 2005/0106300 | A1 | 5/2005 | Chen et al. |
| 2005/0158325 | A1 | 7/2005 | Hammerbeck et al. |
| 2005/0165043 | A1 | 7/2005 | Miller et al. |
| 2005/0171072 | A1 | 8/2005 | Tomai et al. |
| 2005/0239735 | A1 | 10/2005 | Miller et al. |
| 2005/0245562 | A1 | 11/2005 | Garcia-Echeverria et al. |
| 2006/0045885 | A1 | 3/2006 | Kedl et al. |
| 2006/0045886 | A1 | 3/2006 | Kedl |
| 2006/0051374 | A1 | 3/2006 | Miller et al. |
| 2006/0088542 | A1 | 4/2006 | Braun |
| 2006/0142202 | A1 | 6/2006 | Alkan et al. |
| 2006/0142235 | A1 | 6/2006 | Miller et al. |
| 2006/0195067 | A1 | 8/2006 | Wolter et al. |
| 2006/0216333 | A1 | 9/2006 | Miller et al. |
| 2007/0060754 | A1 | 3/2007 | Lindstrom et al. |
| 2007/0066639 | A1 | 3/2007 | Kshirsagar et al. |
| 2007/0072893 | A1 | 3/2007 | Krepski et al. |
| 2007/0099901 | A1 | 5/2007 | Krepski et al. |
| 2007/0123559 | A1 | 5/2007 | Statham et al. |
| 2007/0155767 | A1 | 7/2007 | Radmer et al. |
| 2007/0166384 | A1 | 7/2007 | Zarraga et al. |
| 2007/0167479 | A1 | 7/2007 | Busch et al. |
| 2007/0213355 | A1 | 9/2007 | Capraro et al. |
| 2007/0219196 | A1 | 9/2007 | Krepski et al. |
| 2007/0243215 | A1 | 10/2007 | Miller et al. |
| 2007/0259881 | A1 | 11/2007 | Dellaria et al. |
| 2007/0259907 | A1 | 11/2007 | Prince |
| 2007/0287725 | A1 | 12/2007 | Moser et al. |
| 2007/0292456 | A1 | 12/2007 | Hammerbeck et al. |
| 2008/0015184 | A1 | 1/2008 | Kshirsagar et al. |
| 2008/0039533 | A1 | 2/2008 | Sahouani et al. |
| 2008/0063714 | A1 | 3/2008 | Sahouani et al. |

| | | | | | | |
|---|---|---|---|---|---|---|
| 2008/0070907 | A1 | 3/2008 | Griesgraber et al. | 2008/0213308 A1 | 9/2008 | Valiante et al. |
| 2008/0085895 | A1 | 4/2008 | Griesgraber et al. | 2008/0262021 A1 | 10/2008 | Capraro et al. |
| 2008/0119508 | A1 | 5/2008 | Slade et al. | 2008/0262022 A1 | 10/2008 | Lee et al. |
| 2008/0188513 | A1 | 8/2008 | Skwierczynski et al. | 2008/0269192 A1 | 10/2008 | Griesgraber et al. |
| 2008/0193468 | A1 | 8/2008 | Levy et al. | 2008/0306252 A1 | 12/2008 | Crooks et al. |
| 2008/0193474 | A1 | 8/2008 | Griesgraber et al. | | | |
| 2008/0207674 | A1 | 8/2008 | Stoesz et al. | | | |

\* cited by examiner

HYDROXYALKYL SUBSTITUTED IMIDAZONAPHTHYRIDINES

CROSS REFERENCE TO RELATED APPLICATIONS

This application is a national stage filing under 35 U.S.C.§371 of PCT International application PCT/US2006/006043 designating the United States of America, and filed Feb. 22, 2006. This application claims the benefit under 35 U.S.C. §119(e) of U.S. provisional application Ser. No. 60/655,508, filed Feb. 23, 2005, which is incorporated herein by reference.

BACKGROUND

Certain compounds have been found to be useful as immune response modifiers (IRMs), rendering them useful in the treatment of a variety of disorders. However, there continues to be interest in and a need for compounds that have the ability to modulate the immune response, by induction of cytokine biosynthesis or other means.

SUMMARY

The present invention provides a new class of compounds which preferentially induce the biosynthesis of interferon (α) (IFN-α) in animals. Such compounds are of the following Formulas I, II, and III:

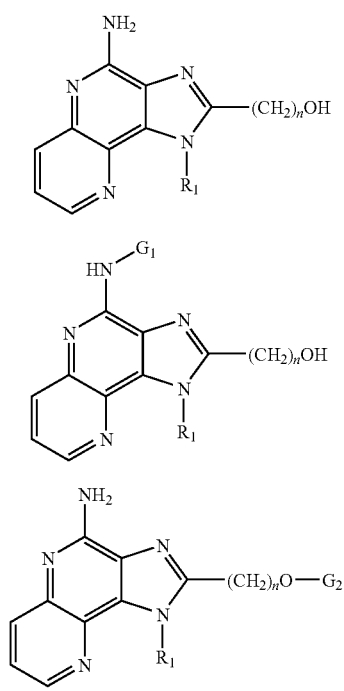

wherein $R_1$, $G_1$, $G_2$, and n are as defined below.

It has now surprisingly been discovered that the amount of TNF-α induced by the 2-(hydroxyalkyl) substituted compounds of the invention is substantially less than the amount of TNF-α induced by closely related analogs having an alkyl or alkyl ether substituent at the 2-position and that the compounds of the invention still retain the ability to induce the biosynthesis of IFN-α. See, for example, FIGS. 1 and 2 below. The reduction in the amount of TNF-α induced is seen over a broad, range of test concentrations. In some embodiments the amount of TNF-α induced by the compounds of the invention is at least two-fold less than the amount of TNF-α induced by analogs having an alkyl or alkyl ether substituent at the 2-position. In other embodiments the amount of TNF-α induced by the compounds of the invention is at least three-fold less than the amount of TNF-α induced by analogs having an alkyl, or alkyl ether substituent at the 2-position. In still other embodiments the amount of TNF-α induced by the compounds of the invention is at least four-fold less than the amount of TNF-α induced by analogs having an alkyl or alkyl ether substituent at the 2-position.

As used herein "substantially less than the amount of TNF-α" means that there is at least a two-fold reduction in the maximal TNF-α response as determined using the test methods described herein.

The compounds or salts of Formulas I, II, and III are especially useful as immune response modifiers due to their ability to preferentially induce interferon-α, thus providing a benefit over compounds that also induce pro-inflammatory cytokines (e.g. TNF-α) or that induce pro-inflammatory cytokines at higher levels.

A compound is said to preferentially induce IFN-α if, when tested according to the test methods described herein, the effective minimum concentration for IFN-α induction is less than the effective minimum concentration for TNF-α induction. In some embodiments, the effective minimum concentration for IFN-α induction is at least 3-fold less than the effective minimum concentration for TNF-α induction. In some embodiments, the effective minimum concentration for IFN-α induction is at least 6-fold less than the effective minimum concentration for TNF-α induction. In other embodiments, the effective minimum concentration for IFN-α induction is at least 9-fold less than the effective minimum concentration for TNF-α induction. In some embodiments, when tested according to the test methods described herein, the amount TNF-α induced by compounds of the invention is at or below the background level of TNF-α in the test method.

The invention further provides pharmaceutical compositions containing an effective amount of a compound or salt of Formulas I, II, and/or III and methods of preferentially inducing the biosynthesis of IFN-α in an animal, and treating a viral infection or disease and/or treating a neoplastic disease in an animal by administering an effective amount of a compound or salt of Formulas I, II, and/or III or a pharmaceutical compositions containing an effective amount of a compound or salt of Formulas I, II, and/or III to the animal.

In addition, methods of synthesizing compounds of Formulas I, II, and III and intermediates useful in the synthesis of these compounds are provided.

As used herein, "a," "an," "the," "at least one," and "one or more" are used interchangeably.

The terms "comprises" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. In several places throughout the description, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS OF THE INVENTION

Figure 1:
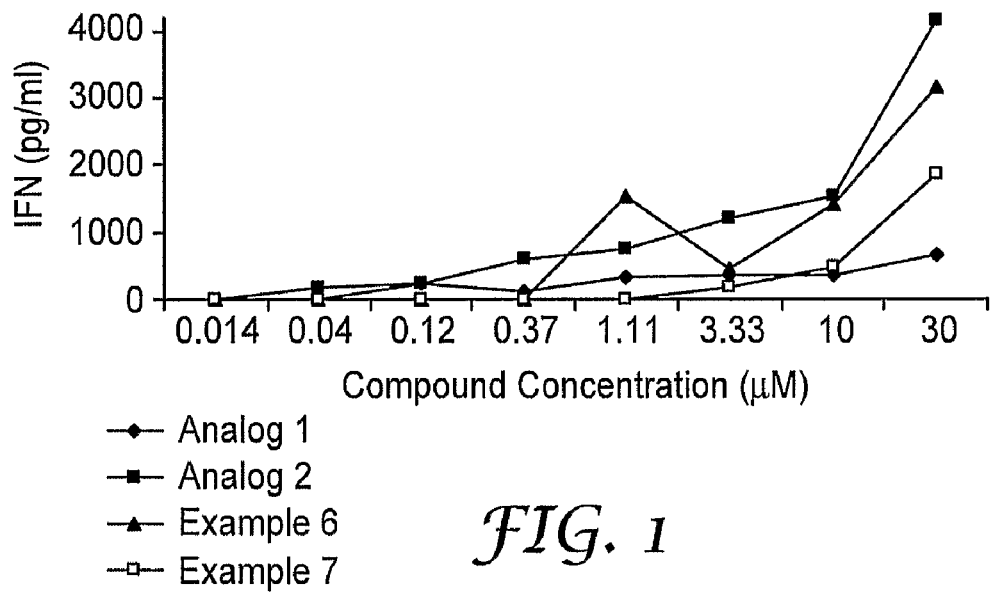
FIG. 1 shows the IFN-α dose response curves (corresponding to values shown in Table 3 below) for Example 6, Example 7, Analog 1, and Analog 2.

The present invention provides compounds of the following Formulas I, II, and III:

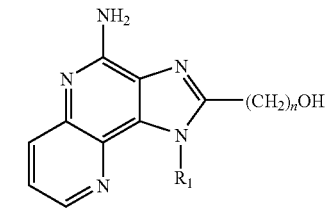

I

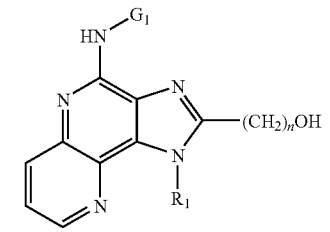

II

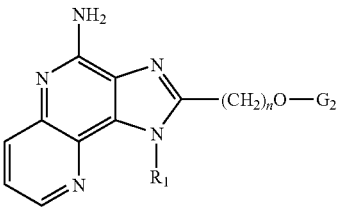

III wherein $R_1$, $G_1$, $G_2$, and n are as defined below; and pharmaceutically acceptable salts thereof.

In one embodiment, the present invention provides a compound of the following Formula I:

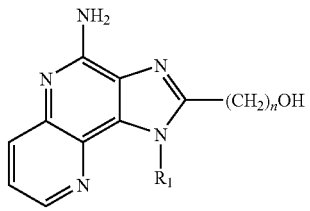

I wherein:
n is 1 or 2;
$R_1$ is selected from the group consisting of:
—$R_4$,
—X—$R_4$,
—X—Y—$R_4$, and
—X—$R_5$;

X is straight chain or branched chain alkylene which can be optionally interrupted or terminated by arylene and optionally interrupted by one —O— group;

Y is selected from the group consisting of:

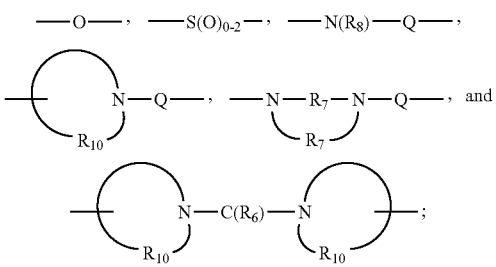

$R_4$ is selected from the group consisting of hydrogen, straight chain or branched chain alkyl, alkenyl, aryl, arylalkylenyl, heteroaryl, heteroarylalkylenyl, and heterocyclylalkylenyl, wherein the alkyl, alkenyl, aryl, arylalkylenyl, heteroaryl, and heteroarylalkylenyl, groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, heteroaryl, heteroaryloxy, heterocyclyl, amino, alkylamino, dialkylamino, and in the case of alkyl and alkenyl, oxo, and wherein heterocyclylalkylenyl can be unsubstituted or substituted by one or more $C_{1-4}$ alkyl groups;

with the proviso that when $R_1$ is —X—Y—$R_4$, then $R_4$ can also be cycloalkyl; and with the further proviso that when $R_1$ is —$R_4$ or —X—$R_4$, then $R_4$ is other than isoxazolyl, isoxazolylalkylenyl, oxadiazolyl, oxadiazolylalkylenyl, dihydroisoxazolyl, or dihydroisoxazolylalkylenyl;

$R_5$ is selected from the group consisting of:

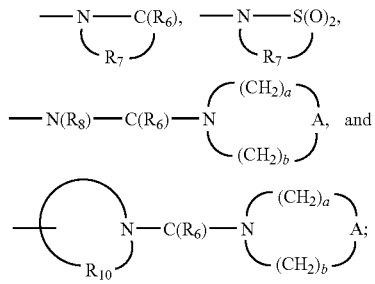

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_{10}$ is $C_{3-8}$ alkylene;
A is selected from the group consisting of —O—, —C(O)—, —$CH_2$—, —$S(O)_{0-2}$—, and —N(Q-$R_4$)—;
Q is selected from the group consisting of a bond, —C($R_6$)—, —$S(O)_2$—, —C($R_6$)—N($R_8$)—, —$S(O)_2$—N($R_8$)—, —C($R_6$)—O—, and —C($R_6$)—S—; and
a and b are independently integers from 1 to 6 with the proviso that a+b is ≦7;
with the further proviso that when Y is —$S(O)_{0-2}$— then X does not contain an —O— group;
or a pharmaceutically acceptable salt thereof.

In another embodiment, the present invention provides a compound of the following Formula II, which is a prodrug:

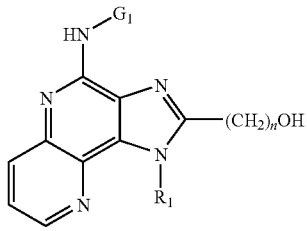

II wherein:
G₁ is selected from the group consisting of:
—C(O)—R',
α-aminoacyl,
α-aminoacyl-α-aminoacyl,
—C(O)—O—R',
—C(O)—N(R")R',
—C(═NY')—R',
—CH(OH)—C(O)—OY',
—CH(OC$_{1-4}$ alkyl)Y₀,
—CH₂Y₁, and
—CH(CH₃)Y₁;

R' and R" are independently selected from the group consisting of C$_{1-10}$ alkyl, C$_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH₃, —C(O)—O—CH₃, —C(O)—NH₂, —O—CH₂—C(O)—NH₂, —NH₂, and —S(O)₂—NH₂, with the proviso that R" can also be hydrogen;

α-aminoacyl is an α-aminoacyl group derived from an α-amino acid selected from the group consisting of racemic, D-, and L-amino acids;

Y' is selected from the group consisting of hydrogen, C$_{1-6}$ alkyl, and benzyl;

Y₀ is selected from the group consisting of C$_{1-6}$ alkyl, carboxy-C$_{1-6}$ alkylenyl, amino-C$_{1-4}$ alkylenyl, mono-N—C$_{1-6}$ alkylamino-C$_{1-4}$ alkylenyl, and di-N,N—C$_{1-6}$ alkylamino-C$_{1-4}$ alkylenyl;

Y₁ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl;

n is 1 or 2;

R₁ is selected from the group consisting of:
—R₄,
—X—R₄,
—X—Y—R₄, and
—X—R₅;

X is straight chain or branched chain alkylene which can be optionally interrupted or terminated by arylene and optionally interrupted by one —O— group;

Y is selected from the group consisting of:

—O—, —S(O)$_{0-2}$—, —N(R₈)—Q—,

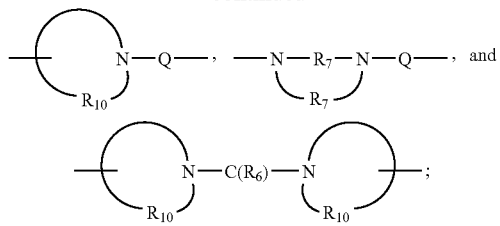

R₄ is selected from the group consisting of hydrogen, straight chain or branched chain alkyl, alkenyl, aryl, arylalkylenyl, heteroaryl, heteroarylalkylenyl, and heterocyclylalkylenyl, wherein the alkyl, alkenyl, aryl, arylalkylenyl, heteroaryl, and heteroarylalkylenyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, heteroaryl, heteroaryloxy, heterocyclyl, amino, alkylamino, dialkylamino, and in the case of alkyl and alkenyl, oxo, and wherein heterocyclylalkylenyl can be unsubstituted or substituted by one or more C$_{1-4}$ alkyl groups;

with the proviso that when R₁ is —X—Y—R₄, then R₄ can also be cycloalkyl; and with the further proviso that when R₁ is —R₄ or —X—R₄, then R₄ is other than isoxazolyl, isoxazolylalkylenyl, oxadiazolyl, oxadiazolylalkylenyl, dihydroisoxazolyl, or dihydroisoxazolylalkylenyl;

R₅ is selected from the group consisting of:

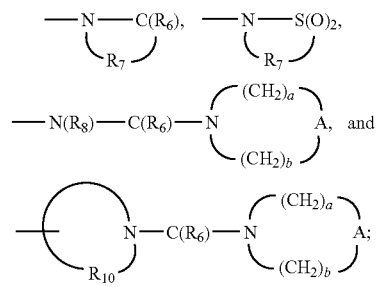

R₆ is selected from the group consisting of ═O and ═S;
R₇ is C$_{2-7}$ alkylene;
R₈ is selected from the group consisting of hydrogen, alkyl, alkoxyalkylenyl, hydroxyalkylenyl, arylalkylenyl, and heteroarylalkylenyl;
R₁₀ is C$_{3-8}$ alkylene;
A is selected from the group consisting of —O—, —C(O)—, —CH₂—, —S(O)$_{0-2}$—, and —N(Q-R₄)—;
Q is selected from the group consisting of a bond, —C(R₆)—, —S(O)₂—, —C(R₆)—N(R₈)—, —S(O)₂—N(R)—, —C(R₆)—O—, and —C(R₆)—S—; and
a and b are independently integers from 1 to 6 with the proviso that a+b is ≦7;
with the further proviso that when Y is —S(O)$_{0-2}$— then X does not contain an —O— group;
or a pharmaceutically acceptable salt thereof.

In another embodiment, the present invention provides a compound of the following Formula III, which is a prodrug:

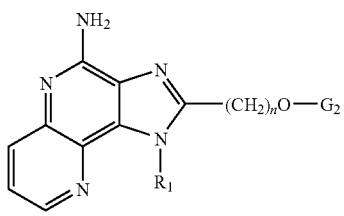

III wherein:

G$_2$ is selected from the group consisting of:
—X$_2$—C(O)—R',
α-aminoacyl,
α-aminoacyl-α-aminoacyl,
—X$_2$—C(O)—O—R', and
—C(O)—N(R")R';

X$_2$ is selected from the group consisting of a bond; —CH$_2$—O—; —CH(CH$_3$)—O—; —C(CH$_3$)$_2$—O—; and, in the case of —X$_2$—C(O)—O—R', —CH$_2$—NH—;

R' and R" are independently selected from the group consisting of C$_{1-10}$ alkyl, C$_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R' can also be hydrogen;

α-aminoacyl is an α-aminoacyl group derived from an α-amino acid selected from the group consisting of racemic, D-, and L-amino acids;

n is 1 or 2;

R$_1$ is selected from the group consisting of:
—R$_4$,
—X—R$_4$,
—X—Y—R$_4$, and
—X—R$_5$;

X is straight chain or branched chain alkylene which can be optionally interrupted or terminated by arylene and optionally interrupted by one —O— group;

Y is selected from the group consisting of:

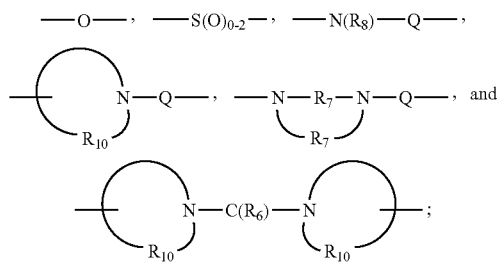

R$_4$ is selected from the group consisting of hydrogen, straight chain or branched chain allyl, alkenyl, aryl, arylalkylenyl, heteroaryl, heteroarylalkylenyl, and heterocyclylalkylenyl, wherein the alkyl, alkenyl, aryl, arylalkylenyl, heteroaryl, and heteroarylalkylenyl, groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, heteroaryl, heteroaryloxy, heterocyclyl, amino, alkylamino, dialkylamino, and in the case of alkyl and alkenyl, oxo, and wherein heterocyclylallylenyl can be unsubstituted or substituted by one or more C$_{1-4}$ alkyl groups;

with the proviso that when R$_1$ is —X—Y—R$_4$, then R$_4$ can also be cycloalkyl; and with the further proviso that when R$_1$ is —R$_4$ or —X—R$_4$, then R$_4$ is other than isoxazolyl, isoxazolylalkylenyl, oxadiazolyl, oxadiazolylalkylenyl, dihydroisoxazolyl, or dihydroisoxazolylalkylenyl;

R$_5$ is selected from the group consisting of:

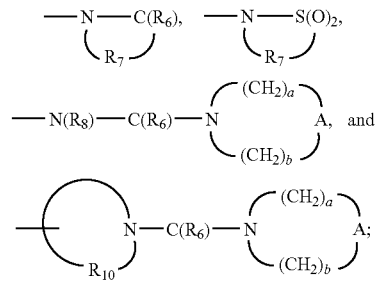

R$_6$ is selected from the group consisting of =O and =S;
R$_7$ is C$_{2-7}$ alkylene;
R$_8$ is selected from the group consisting of hydrogen, alkyl, alkoxyalkylenyl, hydroxyalkylenyl, arylalkylenyl, and heteroarylalkylenyl;
R$_{10}$ is C$_{3-8}$ alkylene;
A is selected from the group consisting of —O—, —C(O)—, —CH$_2$—, —S(O)$_{0-2}$—, and —N(Q-R$_4$)—;
Q is selected from the group consisting of a bond, —C(R$_6$)—, —S(O)$_2$, —C(R$_6$)—N(R$_8$)—, —S(O)$_2$—N(R$_8$)—, —C(R$_6$)—O—, and —C(R$_6$)—S—; and
a and b are independently integers from 1 to 6 with the proviso that a+b is ≦7;
with the further proviso that when Y is —S(O)$_{0-2}$— then X does not contain an —O— group;
or a pharmaceutically acceptable salt thereof.

Unless otherwise specified, as used herein, the terms "alkyl", "alkenyl", "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene", "alkenylene", and "alkynylene" are the divalent forms of the "alkyl", "alkenyl", and "alkynyl" groups defined above. The terms, "alkylenyl", "alkenylenyl", and "alkynylenyl" are use when "alkylene.", "alkenylene", and "alkynylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-." Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

Unless otherwise indicated, the term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. Exemplary heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

Unless otherwise indicated, the term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

Unless otherwise indicated, the term "heterocyclyl" includes bicyclic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene", "heteroarylene", and "heterocyclylene", respectively, are substituted. For example, an alkylarylenyl group comprises an arylene moiety to which an alkyl group is attached.

When a group (or substituent or variable) is present more than once in any Formula described herein, each group (or substituent or variable) is independently selected, whether explicitly stated or not. For example, for the formula —N($R_8$)—C(O)—N(R)— each $R_8$ group is independently selected. In another example, when two $R_{10}$ groups are present each $R_{10}$ group is independently selected.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term "prodrug" means a compound that can be transformed in vivo to yield an immune response modifying compound, including any of the salt, solvated, polymorphic, or isomeric forms described above. The prodrug, itself, may be an immune response modifying compound, including any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and, W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For any of the compounds presented herein, each one of the following variables (e.g., Y, X, $R_1$, Q, $G_1$, $G_2$, n, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments of Formula I, II, or III, n is 1.

For certain embodiments of Formula I, II, or III, n is 2.

For certain embodiments of Formula I, II, or III, including any one of the above embodiments, $R_1$ is selected from the group consisting of alkyl, aminoalkyl, dihydroxyalkyl, haloalkyl, and hydroxyalkyl; wherein alkyl is straight chain or branched chain. For certain of these embodiments, $R_1$ is selected from the group consisting of methyl, ethyl, n-propyl, n-butyl, 2-methylpropyl, 2-amino-2-methylpropyl, 3-amino-2,2-dimethylpropyl, 2,3-dihydroxypropyl, 2-fluoro-2-methylpropyl, and 2-hydroxy-2-methylpropyl.

For certain embodiments of Formula I, II, or III, including any one of the above embodiments, $R_1$ is heterocyclylalkylenyl which is unsubstituted or substituted by one or more $C_{1-4}$ alkyl groups, except where $R_1$ as defined does not include this definition. For certain of these embodiments, $C_{1-4}$ alkyl is methyl. For certain of these embodiments, heterocyclyl is selected from the group consisting of 1,3-dioxolanyl, tetrahydropyranyl, tetrahydrofuranyl, pyrrolidinyl, piperidinyl, and morpholinyl, and alkylenyl is $C_{1-4}$ alkylenyl. For certain of these embodiments, as well as any one of the above embodiments which does not exclude this definition, $R_1$ is selected from the group consisting of tetrahydro-2H-pyran-4-ylmethyl and (2,2-dimethyl-1,3-dioxolan-4-yl)methyl.

For certain embodiments of Formula I, II, or III, including any one of the above embodiments, $R_1$ is —X—Y—$R_4$, except where $R_1$ as defined does not include this definition, wherein X is straight chain or branched chain $C_{1-6}$ alkylene which may be interrupted by one —O— group; Y is selected from the group consisting of —N($R_8$)—C(O)—, —N($R_8$)—S(O)$_2$—, —N($R_8$)—C(O)—N($R_8$)—, and —S(O)$_2$— wherein $R_8$ is selected from hydrogen and methyl; and $R_4$ is selected from the group consisting of $C_{1-6}$ alkyl, isoquinolinyl, N-methylimidazolyl, pyridinyl, quinolinyl, phenyl, and phenyl substituted by a substituent selected from the group consisting of chloro, cyano, fluoro, hydroxy, and methyl; with the proviso that when Y is —S(O)$_2$— then X does not contain an —O— group. For certain of these embodiments, as well as any one of the above embodiments, $R_1$ is selected from the group consisting of 2-[(cyclopropylcarbonyl)amino]ethyl, 4-[(cyclopropylcarbonyl)amino]butyl, 2-[(cyclohexylcarbonyl)amino]-2-methylpropyl, 2-{[(1-methylethyl)carbonyl]amino}ethyl, 4-{[(1-methylethyl)carbonyl]amino}butyl, 2-methyl-2-{[(1-methylethyl)carbonyl]amino}propyl, 2-[(methylsulfonyl)amino]ethyl, 4-[(methylsulfonyl)amino]butyl, 2-methyl-2-[(methylsulfonyl)amino]propyl, 2-methyl-2-({[(1-methylethyl)amino]carbonyl}amino)propyl, and 2,2-dimethyl-3-(methylsulfonyl)propyl, except where $R_1$ as defined does not include this definition.

For certain embodiments of Formula I, II, or III, including any one of the above embodiments, except where $R_1$ as defined does not include this definition, $R_1$ is —X—Y—$R_4$ wherein X is straight chain or branched chain $C_{1-6}$ alkylene which may be interrupted by one —O— group; Y is selected from the group consisting of —N($R_8$)—C(O)—, —N($R_8$)—S(O)$_2$—, —N($R_8$)—C(O)—N($R_8$)—, —N($R_8$)—S(O)$_2$—N($R_8$)—, and —S(O)$_2$— wherein $R_8$ is selected from hydrogen and methyl; and $R_4$ is selected from the group consisting of $C_{1-6}$ alkyl, aryl, arylalkylenyl, and heteroaryl which is unsubstituted or substituted by methyl, wherein aryl, and arylalkylenyl are unsubstituted or substituted by a substituent selected from the group consisting of chloro, cyano, fluoro, hydroxy, and methyl; with the proviso that when Y is —S(O)$_2$— then X does not contain an —O— group. For certain of these embodiments, $R_4$ is heteroaryl. For certain of these embodiments, heteroaryl is isoquinolinyl, N-methylimidazolyl, pyridinyl, or quinolinyl. Alternatively, for certain of these embodiments, $R_4$ is aryl which is unsubstituted or substituted by a substituent selected from the group consisting of chloro, cyano, fluoro, hydroxy, and methyl. For certain of these embodiments, aryl is phenyl which is unsubstituted or substituted by a substituent selected from the group consisting of chloro, cyano, fluoro, hydroxy, and methyl. Alternatively, for certain of these embodiments, $R_4$ is arylalkylenyl which is unsubstituted or substituted by a substituent selected from the group consisting of chloro, cyano, fluoro, hydroxy, and methyl. For certain of these embodiments, arylalkylenyl is phenyl-$C_{1-4}$ alkylenyl. For certain of these embodiments, $C_{1-4}$ alkylenyl is methylene, ethylene, or cyclopropylene. Alternatively, $R_4$ is $C_{1-6}$ alkyl.

For certain embodiments of Formula I, including any one of the above embodiments, $R_1$ is —X—$R_5$, except where $R_1$ as defined does not include this definition, wherein X is straight chain or branched chain $C_{1-6}$ alkylene, and $R_5$ is

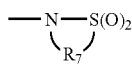

or

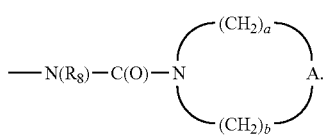

For certain of these embodiments, $R_5$ is

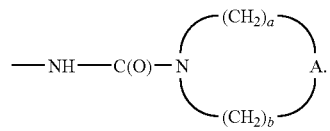

For certain of these embodiments, as well as any one of the above embodiments, $R_1$ is selected from the group consisting of 4-(1,1-dioxidoisothiazolidin-2-yl)butyl, 4-[(4-morpholinecarbonyl)amino]butyl, and 2-[(4-morpholinecarbonyl)amino]ethyl, except where $R_1$ as defined does not include this definition.

For certain embodiments, for example, embodiments of Formula I, the present invention provides the compound 2-hydroxymethyl-1-(2-methylpropyl)-1H-imidazo[4,5-c][1,5]naphthyridin-4-amine or a pharmaceutically acceptable salt thereof. These are also embodiments of any one of the above embodiments, except where an above embodiment does not include this compound or the salts thereof.

For certain embodiments, for example, embodiments of Formula I, the present invention provides a compound selected from the group consisting of 1-(4-amino-2-hydroxymethyl-1H-imidazo[4,5-c][1,5]naphthyrin-1-yl)-2-methylpropan-2-ol and 1-[4-amino-2-(2-hydroxyethyl)-1H-imidazo[4,5-c][1,5]naphthyrin-1-yl]-2-methylpropan-2-ol, or a pharmaceutically acceptable salt thereof. These are also embodiments of any one of the above embodiments, except where an above embodiment does not include these compounds or salts.

For certain embodiments, for example, embodiments of Formula I, the present invention provides a compound selected from the group consisting of N-[4-(4-amino-2-hydroxymethyl-1H-imidazo[4,5-c][1,5]naphthyrin-1-yl)butyl]methanesulfonamide and N-{4-[4-amino-2-(2-hydroxyethyl)-1H-imidazo[4,5-c][1,5]naphthyrin-1-yl]butyl]}methanesulfonamide, or a pharmaceutically acceptable salt thereof. These are also embodiments of any one of the above embodiments, except where an above embodiment does not include these compounds or salts.

For certain embodiments, the present invention provides a pharmaceutical composition comprising a therapeutically effective amount of a compound or salt of Formula I, II, III, or of any one of the above embodiments and a pharmaceutically acceptable carrier.

For certain embodiments, the present invention provides a method of preferentially inducing the biosynthesis of IFN-α in an animal comprising administering an effective amount of a compound or salt of Formula I, II, III, or of any one of the above embodiments or the above pharmaceutical composition to the animal.

For certain embodiments, the present invention provides a method of treating a viral disease in an animal in need thereof comprising administering a therapeutically effective amount of a compound or salt of Formula I, II, III, or of any one of the above embodiments or the above pharmaceutical composition to the animal. For certain of these embodiments, the method includes preferentially inducing the biosynthesis of IFN-α.

For certain embodiments, the present invention provides a method of treating a neoplastic disease in an animal in need thereof comprising administering a therapeutically effective amount of a compound or salt of Formula I, II, III, or of any one of the above embodiments or the above pharmaceutical composition to the animal. For certain of these embodiments, the method includes preferentially inducing the biosynthesis of IFN-α.

For certain embodiments of the above methods, the compound or salt or pharmaceutical composition is administered systemically.

For certain embodiments, $R_1$ is selected from the group consisting of —$R_4$, —X—$R_4$—, —X—Y—$R_4$, and —X—$R_5$.

For certain embodiments, $R_1$ is —$R_4$.

For certain embodiments, $R_1$ is selected from the group consisting of alkyl, aminoalkyl, dihydroxyalkyl, haloalkyl, and hydroxyalkyl; wherein alkyl is straight chain or branched chain.

For certain embodiments, $R_1$ is selected from the group consisting of methyl, ethyl, n-propyl, n-butyl, 2-methylpropyl, 2-amino-2-methylpropyl, 3-amino-2,2-dimethylpropyl, 2,3-dihydroxypropyl, 2-fluoro-2-methylpropyl, and 2-hydroxy-2-methylpropyl.

For certain embodiments, $R_1$ is heterocyclylalkylenyl which can be unsubstituted or substituted by one or more $C_{1-4}$ alkyl groups.

For certain embodiments, $R_1$ is heterocyclylalkylenyl wherein heterocyclyl is selected from the group consisting of 1,3-dioxolanyl, tetrahydropyranyl, tetrahydrofuranyl, pyrrolidinyl, piperidinyl, and morpholinyl, and alkylenyl is $C_{1-4}$ alkylenyl.

For certain embodiments, $R_1$ is selected from the group consisting of tetrahydro-2H-pyran-4-ylmethyl and (2,2-dimethyl-1,3-dioxolan-4-yl)methyl.

For certain embodiments, $R_1$ is —X—Y—$R_4$.

For certain embodiments, $R_1$ is —X—Y—$R_4$ wherein X is straight chain or branched chain $C_{1-6}$ alkylene which may be interrupted by one —O— group; Y is selected from the group consisting of —N($R_8$)—C(O)—, —N($R_8$)—S(O)$_2$—, —N($R_8$)—C(O)—N($R_8$)—, —N($R_8$)—S(O)$_2$—N($R_8$)—, and —S(O)$_2$— wherein $R_8$ is selected from hydrogen and methyl; and $R_4$ is selected from the group consisting of $C_{1-6}$ alkyl, aryl, arylalkylenyl, and heteroaryl which is unsubstituted or substituted by methyl, wherein aryl and arylalkylenyl are unsubstituted or substituted by a substituent selected from the group consisting of chloro, cyano, fluoro, hydroxy, and methyl; with the proviso that when Y is —S(O)$_2$— then X does not contain an —O— group. For certain of these embodiments, $R_4$ is heteroaryl. For certain of these embodiments, heteroaryl is isoquinolinyl, N-methylimidazolyl, pyridinyl, or quinolinyl. Alternatively, for certain of these embodiments, $R_4$ is aryl which is unsubstituted or substituted by a substituent selected from the group consisting of chloro, cyano, fluoro, hydroxy, and methyl. For certain of these embodiments, aryl is phenyl which is unsubstituted or substituted by a substituent selected from the group consisting of chloro, cyano, fluoro, hydroxy, and methyl. Alternatively, for certain of these embodiments, $R_4$ is arylalkylenyl which is unsubstituted or substituted by a substituent selected from the group consisting of chloro, cyano, fluoro, hydroxy, and methyl. For certain of these embodiments, arylalkylenyl is phenyl-$C_{1-4}$ alkylenyl. Alternatively, $R_4$ is $C_{1-6}$ alkyl.

For certain embodiments, $R_1$ is —X—Y—$R_4$ wherein X is straight chain or branched chain $C_{1-6}$ alkylene which may be interrupted by one —O— group; Y is selected from the group consisting of —N($R_8$)—C(O)—, —N($R_8$)—S(O)$_2$—, —N($R_8$)—C(O)—N($R_8$)—, and —S(O)$_2$— wherein $R_8$ is selected from hydrogen and methyl; and $R_4$ is selected from the group consisting of $C_{1-6}$ alkyl, isoquinolinyl, N-methylimidazolyl, pyridinyl, quinolinyl, phenyl, and phenyl substituted by a substituent selected from the group consisting of chloro, cyano, fluoro, hydroxy, and methyl; with the proviso that when Y is —S(O)$_2$— then X does not contain an —O— group.

For certain embodiments, $R_1$ is selected from the group consisting of 2-[(cyclopropylcarbonyl)amino]ethyl, 4-[(cyclopropylcarbonyl)amino]butyl, 2-[(cyclohexylcarbonyl)amino]-2-methylpropyl, 2-{[(1-methylethyl)carbonyl]amino}ethyl, 4-{[(1-methylethyl)carbonyl]amino}butyl, 2-methyl-2-{[(1-methylethyl)carbonyl]amino}propyl, 2-[(methylsulfonyl)amino]ethyl, 4-[(methylsulfonyl)amino]butyl, 2-methyl-2-[(methylsulfonyl)amino]propyl, 2-methyl-2-({[(1-methylethyl)amino]carbonyl}amino)propyl, and 2,2-dimethyl-3-(methylsulfonyl)propyl.

For certain embodiments, except where excluded, $R_1$ is, —X—Y—$R_4$ wherein X is straight chain or branched chain $C_{1-6}$ alkylene which may be interrupted by one —O— group; Y is selected from the group consisting of —N($R_8$)—C(O)—, —N($R_8$)—S(O)$_2$—, —N($R_8$)—C(O)—N($R_8$)—, and —S(O)$_2$— wherein $R_8$ is selected from hydrogen and methyl; and $R_4$ is arylalkylenyl, wherein aryl is unsubstituted or substituted by a substituent selected from the group consisting of chloro, cyano, fluoro, hydroxy, and methyl; with the proviso that when Y is —S(O)$_2$— then X does not contain an —O— group. For certain of these embodiments, arylalkylenyl is phenyl-$C_{1-4}$ alkylenyl. For certain of these embodiments, $C_{1-4}$ alkylenyl is methylene, ethylene, or cyclopropylene.

For certain embodiments, $R_1$ is —X—$R_5$.

For certain embodiments, $R_1$ is —X—$R_5$ wherein X is straight chain or branched chain $C_{1-6}$ alkylene, and $R_5$ is

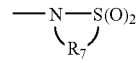

or

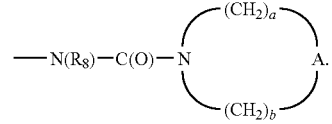

For certain of these embodiments, $R_5$ is

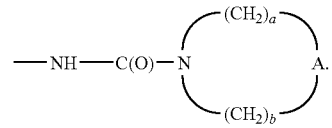

For certain of these embodiments, A is —O—, —CH$_2$—, or —N(Q-$R_4$)—. For certain of these embodiments, a and b are each 2. For certain of these embodiments, A is —O—. Alternatively, for certain of these embodiments, A is —CH$_2$—. Alternatively, for certain of these embodiments, A is —N(Q-$R_4$)—. For certain of these embodiments, Q is a bond and $R_4$ is alkyl. For certain of these embodiments, $R_4$ is methyl.

For certain embodiments, $R_1$ is selected from the group consisting of 4-(1,1-dioxidoisothiazolidin-2-yl)butyl, 4-[(4-morpholinecarbonyl)amino]butyl, and 2-[(4-morpholinecarbonyl)amino]ethyl.

For certain embodiments, $R_4$ is selected from the group consisting of hydrogen, straight chain or branched chain alkyl, alkenyl, aryl, arylalkylenyl, heteroaryl, heteroarylalkylenyl, and heterocyclylalkylenyl, wherein the alkyl, alkenyl, aryl, arylalkylenyl, heteroaryl, and heteroarylalkylenyl, groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, heteroaryl, heteroaryloxy, heterocyclyl, amino, alkylamino, dialkylamino, and in the case of alkyl and alkenyl, oxo, and wherein heterocyclylalkylenyl can be unsubstituted or substituted by one or more $C_{1-4}$ alkyl groups; with the proviso that when $R_1$ is —X—Y—$R_4$, then $R_4$ can also be cycloalkyl; and with the further proviso that when $R_1$ is —$R_4$ or —X—$R_4$, then $R_4$ is other than isoxazolyl, isoxazolylalkylenyl, oxadiazolyl, oxadiazolylalkylenyl, dihydroisoxazolyl, or dihydroisoxazolylalkylenyl.

For certain embodiments, $R_4$ is selected from the group consisting of hydrogen, straight chain or branched chain alkyl, alkenyl, aryl, arylalkylenyl, heteroaryl, and heteroarylalkylenyl, wherein the alkyl, alkenyl, aryl, arylalkylenyl, heteroaryl, and heteroarylalkylenyl, groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, heteroaryl, heteroaryloxy, heterocyclyl, amino, alkylamino, dialkylamino, and in the case of alkyl and alkenyl, oxo; with the proviso that when $R_1$ is —X—Y—$R_4$, then $R_4$ can also be cycloalkyl; and with the further proviso that when $R_1$ is —$R_4$ or —X—$R_4$, then $R_4$ is other than isoxazolyl, isoxazolylalkylenyl, oxadiazolyl, oxadiazolylalkylenyl, dihydroisoxazolyl, or dihydroisoxazolylalkylenyl.

For certain embodiments, $R_4$ in —X—Y—$R_4$ is arylalkylenyl, wherein aryl is unsubstituted or substituted by a substituent selected from the group consisting of chloro, cyano, fluoro, hydroxy, and methyl. For certain of these embodiments, arylalkylenyl is phenyl-$C_{1-4}$ alkylenyl. For certain of these embodiments, $C_{1-4}$ alkylenyl is methylene, ethylene, or cyclopropylene.

For certain embodiments, $R_4$ in —X—Y—$R_4$ is selected from the group consisting of $C_{1-6}$ alkyl, isoquinolinyl, N-methylimidazolyl, pyridinyl, quinolinyl, phenyl, and phenyl substituted by a substituent selected from the group consisting of chloro, cyano, fluoro, hydroxy, and methyl.

For certain embodiments, $R_4$ is $C_{1-6}$ alkyl.

For certain embodiments, $R_4$ is cyclopropyl, cyclobutyl, cyclopentyl or cyclohexyl.

For certain embodiments, $R_4$ is methyl.

For certain embodiments, $R_4$ is aryl.

For certain embodiments, $R_4$ is phenyl.

For certain embodiments, $R_4$ is phenyl substituted by a substituent selected from the group consisting of chloro, cyano, fluoro, hydroxy, and methyl.

For certain embodiments, $R_4$ is arylalkylenyl.

For certain embodiments, $R_4$ is phenyl-$C_{1-4}$ alkylenyl.

For certain embodiments, $R_4$ is heteroaryl.

For certain embodiments, $R_4$ is isoquinolinyl, N-methylimidazolyl, pyridinyl, or quinolinyl.

For certain embodiments, $R_4$ is pyridin-3-yl or pyridin-4-yl.

For certain embodiments, $R_5$ is selected from the group consisting of:

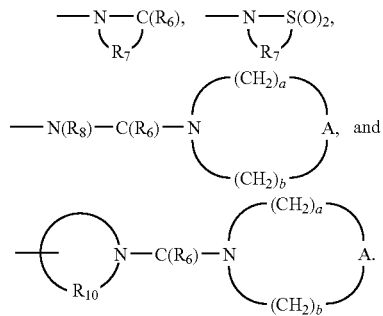

For certain embodiments, $R_5$ is

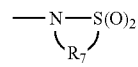

or

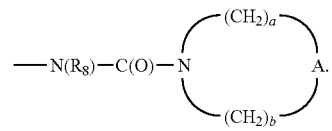

For certain embodiments, $R_5$ is

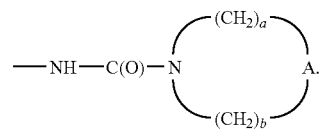

For certain embodiments, $R_6$ is selected from the group consisting of =O and =S.

For certain embodiments, $R_6$ is =O.

For certain embodiments, $R_6$ is =S.

For certain embodiments, $R_7$ is $C_{2-7}$ alkylene.

For certain embodiments, $R_7$ is $C_{2-4}$ alkylene.

For certain embodiments, $R_8$ is selected from the group consisting of hydrogen, alkyl, alkoxyalkylenyl, hydroxyalkylenyl, arylalkylenyl, and heteroarylalkylenyl.

For certain embodiments, $R_8$ is selected from the group consisting of hydrogen, $C_{1-4}$ alkyl, and $C_{1-4}$ alkoxy$C_{1-4}$ alkylenyl.

For certain embodiments, $R_8$ is hydrogen or $C_{1-4}$ alkyl.

For certain embodiments, $R_8$ is selected from hydrogen and methyl.

For certain embodiments, $R_8$ is methyl.

For certain embodiments, $R_8$ is hydrogen.

For certain embodiments, $R_{10}$ is $C_{3-8}$ alkylene.

For certain embodiments, $R_{10}$ is $C_{4-6}$ alkylene.

For certain embodiments, A is selected from the group consisting of —O—, —C(O)—, —CH$_2$—, —S(O)$_{0-2}$—, and —N(Q-$R_4$)—.

For certain embodiments, A is —O—, —CH$_2$—, —S—, or —S(O)$_2$—.

For certain embodiments, A is —O— or —S(O)$_2$—.

For certain embodiments, A is —O—.

For certain embodiments, A is —CH$_2$—.

For certain embodiments, A is —N(Q-R$_4$)—.

For certain embodiments, including any one of the above embodiments of Formula II, G$_1$ is selected from the group consisting of —C(O)—R', α-aminoacyl, α-aminoacyl-α-aminoacyl, —C(O)—O—R', —C(O)—N(R")R', —C(=NY')—R', —CH(OH)—C(O)—OY', —CH(OC$_{1-4}$ alkyl)Y$_0$, —CH$_2$Y$_1$, and —CH(CH$_3$)Y$_1$; R' and R" are independently selected from the group consisting of C$_{1-10}$ alkyl, C$_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, C$_{1-6}$ alkyl, C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —(O)$_2$—NH$_2$, with the proviso that R" can also be hydrogen; α-aminoacyl is an α-aminoacyl group derived from an α-amino acid selected from the group consisting of racemic, D-, and L-amino acids; Y' is selected from the group consisting of hydrogen, C$_{1-6}$ alkyl, and benzyl; Y$_0$ is selected from the group, consisting of C$_{1-6}$ alkyl, carboxy-C$_{1-6}$ alkylenyl, amino-C$_{1-4}$ alkylenyl, mono-N—C$_{1-6}$ alkylamino-C$_{1-4}$ alkylenyl, and di-N,N—C$_{1-6}$ alkylamino-C$_{1-4}$ alkylenyl; and Y$_1$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl.

For certain embodiments, including any one of the above embodiments of Formula. II, G$_1$ is selected from the group consisting of —C(O)—R', α-aminoacyl, and —C(O)—O—R'. For certain of these embodiments, R' contains one to ten carbon atoms. For certain of these embodiments, α-aminoacyl is an α-C$_{2-11}$ aminoacyl group derived from an α-amino acid selected from the group consisting of racemic, D-, and L-amino acids containing a total of at least 2 carbon atoms and a total of up to 11 carbon atoms, and may also include one or more heteroatoms selected from the group consisting of O, S, and N.

For certain embodiments, including any one of the above embodiments of Formula III, G$_2$ is selected from the group consisting of —X$_2$—C(O)—R', α-aminoacyl, α-aminoacyl-α-aminoacyl, —X$_2$—C(O)—O—R', and —C(O)—N(R")R'. For certain of these embodiments, X$_2$ is selected from the group consisting of a bond; —CH$_2$—O—; —CH(CH$_3$)—O—; —C(CH$_3$)$_2$—O—; and, in the case of —X$_2$—C(O)—O—R', —CH$_2$—NH—; R' and R" are independently selected from the group consisting of C$_{1-10}$ alkyl, C$_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, C$_{1-6}$ alkyl C$_{1-4}$ alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen; and α-aminoacyl is an α-aminoacyl group derived from an α-amino acid selected from the group consisting of racemic, D-, and L-amino acids.

For certain embodiments, including any one of the above embodiments of Formula III, G$_2$ is selected from the group consisting of —C(O)—R' and α-aminoacyl, wherein R' is C$_{1-6}$ alkyl or phenyl which is unsubstituted or substituted by one or more substituents independently selected from the group consisting of halogen, hydroxy, nitro, cyano, carboxy, C$_{1-6}$ alkyl, C$_{1-4}$-alkoxy, aryl, heteroaryl, aryl-C$_{1-4}$ alkylenyl, heteroaryl-C$_{1-4}$ alkylenyl, halo-C$_{1-4}$ alkylenyl, halo-C$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$.

For certain embodiments, including any one of the above embodiments of Formula III, G$_2$ is selected from the group consisting of α-amino-C$_{2-5}$ alkanoyl, C$_{2-6}$ alkanoyl, C$_{1-6}$ alkoxycarbonyl, and C$_{1-6}$ alkylcarbamoyl.

For certain embodiments, including any one of the above embodiments which include an α-aminoacyl group, α-aminoacyl is an α-aminoacyl group derived from a naturally occurring α-amino acid selected from the group consisting of racemic, D-, and L-amino acids.

For certain embodiments, including any one of the above embodiments which include an α-aminoacyl group, α-aminoacyl is an α-aminoacyl group derived from an α-amino acid found in proteins, wherein the amino acid is selected from the group consisting of racemic, D-, and L-amino acids.

For certain embodiments, the hydrogen atom of the hydroxy group of Formula II (including any one of its embodiments) is replaced by G$_2$, wherein G$_2$ is defined as in any one of the above embodiments of G$_2$.

For certain embodiments, Q is selected from the group consisting of a bond, —C(R$_6$)—, —S(O)$_2$, —C(R$_6$)—N(R)—, —S(O)$_2$—N(R$_8$)—, —C(R$_6$)—O—, and —C(R$_6$)—S—.

For certain embodiments, Q is selected from the group consisting of a bond, —C(R$_6$)—, —S(O)$_2$—, and —C(R$_6$)—N(R$_8$)—.

For certain embodiments, Q is selected from the group consisting of —C(O)—, —S(O)$_2$—, and —C(O)—N(R$_8$)—. In certain of these embodiments, R$_8$ is hydrogen or methyl.

For certain embodiments, Q is —C(O)—.

For certain embodiments, Q is —S(O)$_2$—.

For certain embodiments, Q is —C(R$_6$)—N(R$_8$)—.

For certain embodiments, Q is —C(O)—N(R$_8$)— wherein R$_8$ is hydrogen or methyl.

For certain embodiments, Q is a bond.

For certain embodiments, X is straight chain or branched chain alkylene which can be optionally interrupted or terminated by arylene and optionally interrupted by one —O— group.

For certain embodiments, X is straight chain or branched chain C$_{1-6}$ alkylene which may be interrupted by one —O— group.

For certain embodiments, X is straight chain or branched chain C$_{1-6}$ alkylene.

For certain embodiments, X is —CH$_2$—C(CH$_3$)$_2$—.

For certain embodiments, X is methylene.

For certain embodiments, X is ethylene.

For certain embodiments, X is propylene.

For certain embodiments, X is butylene.

For certain embodiments, Y is selected from the group consisting of —O—, —S(O)$_{0-1}$—,

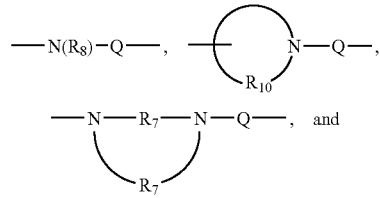

-continued

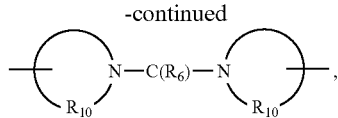

with the proviso that when Y is —S(O)$_{0-2}$— then X does not contain an —O— group.

For certain embodiments, Y is selected from the group consisting of —N(R$_8$)—C(O)—, —N(R$_8$)—S(O)$_2$—, —N(R$_8$)—C(O)—N(R$_8$)—, —N(R$_8$)—S(O)$_2$—N(R$_8$)—, and —S(O)$_2$— wherein R$_8$ is selected from hydrogen and methyl, with the proviso that when Y is —S(O)$_2$— then X does not contain an —O— group.

For certain embodiments, Y is selected from the group consisting of —N(R$_8$)—C(O)—; —N(R$_8$)—S(O)$_2$—, —N(R$_8$)—C(O)—N(R$_8$)—, and —S(O)$_2$—, with the proviso that when Y is —S(O)$_2$— then X does not contain an —O— group. In certain of these embodiments, R$_8$ is selected from hydrogen and methyl.

For certain embodiments, Y is —N(R$_8$)—C(O)—. For certain of these embodiments, X is straight chain or branched chain C$_{1-4}$ alkylene, R$_4$ is C$_{1-6}$ alkyl and R$_8$ is hydrogen.

For certain embodiments, Y is —N(R$_8$)—S(O)$_2$—. For certain of these embodiments, X is straight chain or branched chain C$_{1-4}$ alkylene, R$_4$ is C$_{1-6}$ alkyl, and is hydrogen.

For certain embodiments, Y is —NH—C(O)—N(R$_8$)—. For certain of these embodiments, R$_8$ is hydrogen. Alternatively, for certain of these embodiments, R$_8$ is methyl. For certain of these embodiments, X is straight chain or branched chain C$_{1-4}$ alkylene. For certain of these embodiments, R$_4$ is C$_{1-6}$ alkyl.

For certain embodiments, Y is —S(O)$_2$— with the proviso that when Y is —S(O)$_2$— then X does not contain an —O— group. For certain of these embodiments, X is straight chain or branched chain C$_{1-4}$ alkylene, and R$_4$ is C$_{1-6}$ alkyl.

For certain embodiments, a and b are independently integers from 1 to 6 with the proviso that a+b is ≦7.

For certain embodiments, a and b are each independently 1 to 3.

For certain embodiments, a and b are each 2.

For certain embodiments, a is 1, 2, or 3, and b is 2.

For n certain embodiments, n is 1 or 2.

For certain embodiments, n is 1.

For certain embodiments, n is 2.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v. 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie,* 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

In the preparation of compounds of the invention it may sometimes be necessary to protect a particular functionality while reacting other functional groups on an intermediate. The need for such protection will vary depending on the nature of the particular functional group and the conditions of the reaction step. Suitable amino protecting groups include acetyl, trifluoroacetyl, tert-butoxycarbonyl (Boc), benzyloxycarbonyl, and 9-fluorenylmethoxycarbonyl (Fmoc). Suitable hydroxy protecting groups include acetyl and silyl groups such as the tert-butyl dimethylsilyl group. For a general description of protecting groups and their use, see T. W. Greene and P. G. M. Wuts, *Protective Groups in Organic Synthesis*, John Wiley & Sons, New York, USA, 1991.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

Compounds of the invention can be prepared according to Reaction Scheme I, wherein R$_1$ and n are as defined above and alkyl is methyl or ethyl.

In Reaction Scheme I an ether substituted 1H-imidazo[4,5-c][1,5]naphthyridin-4-amine of Formula X is cleaved to provide a hydroxyalkyl substituted 1H-imidazo[4,5-c][1,5] naphthyridin-4-amine of Formula I. The reaction is conveniently carried out by adding a solution of boron tribromide in a suitable solvent such as dichloromethane to a solution or suspension of a compound of Formula X in a suitable solvent such as dichloromethane at ambient temperature or at a subambient temperature, for example, at 0° C. The product or pharmaceutically acceptable salt thereof can be isolated using conventional methods.

Some compounds of Formula X are known; others can be prepared using known synthetic methods. See, for example, U.S. Pat. No. 6,194,425 and International Publication No. WO 2005/076783. Numerous compounds of Formula X can also be prepared by using 4-chloro-3-nitro[1,5]naphthyridine in lieu of 4-chloro-3-nitroquinoline in the synthetic routes described in U.S. Pat. Nos. 6,756,382; 6,677,349; 6,573,273; 6,664,265; 6,670,372; 6,677,347; 6,660,735; and 6,667,312.

Reaction Scheme I

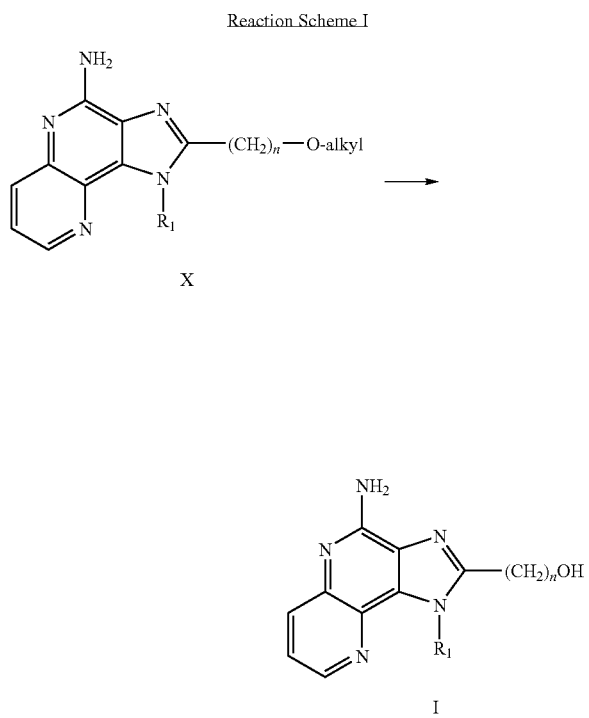

In some embodiments, compounds of the invention can be prepared according to Reaction Scheme II where n is 1 or 2 and $R_{1a}$ is a subset of $R_1$ as defined above that does not include those substituents that one of skill in the art would recognize as being incompatible with the oxidation conditions of step (3), for example, nitrogen containing heteroaryl groups, or the hydrogenolysis conditions of step (5), for example, benzyloxy or benzylamino groups.

In step (1) of Reaction Scheme II, a 1H-imidazo[4,5-c][1,5]naphthyridine-3,4-diamine of Formula XI is reacted with either benzyloxyacetyl chloride or 3-(benzyloxy)propanoyl chloride to provide an N-[1,5]naphthyridin-3-yl amide of Formula XII. The reaction can be carried out by adding the acid chloride to a solution of a compound of Formula XI in a suitable solvent such as dichloromethane in the presence of a tertiary amine such as triethyl amine. The reaction can be carried out at a sub-ambient temperature such as 0° C. Some compounds of Formula XI are known, others can be prepared using known synthetic methods. See, for example, U.S. Pat. No. 6,194,425 and International Publication No. WO 2005/076783. Numerous compounds of Formula XI can also be prepared by using 4-chloro-3-nitro[1,5]naphthyridine in lieu of 4-chloro-3-nitroquinoline in the synthetic routes described in U.S. Pat. Nos. 6,756,382; 6,677,349; 6,573,273; 6,664,265; 6,670,372; 6,677,347; 6,660,735; and 6,667,312.

In step (2) of Reaction Scheme II, an N-[1,5]naphthyridin-3-yl amide of Formula XII is cyclized to provide a 1H-imidazo[4,5-c][1,5]naphthyridine of Formula XIII. The reaction can be carried out by heating a solution of a compound of Formula XII in suitable solvent such as ethanol or methanol in the presence of a base such as triethylamine.

In step (3) of Reaction Scheme II, a 1H-imidazo[4,5-c][1,5]naphthyridine of Formula XIII is oxidized to provide a 5N-oxide of Formula XIV using a conventional oxidizing agent capable of forming N-oxides. The reaction can be carried out by treating a solution of a compound of Formula XIII in a suitable solvent such as dichloromethane or chloroform with 3-chloroperoxybenzoic acid. The reaction can be carried out at ambient temperature.

In step (4) of Reaction Scheme II, a 1H-imidazo[4,5-c][1,5]naphthyridine-5N-oxide of Formula XIV is aminated to provide a 1H-imidazo[4,5-c][1,5]naphthyridin-4-amine of Formula XV. The amination can be carried out by the activation of a 5N-oxide of Formula XIV by conversion to an ester and then reacting the ester with an aminating agent. Suitable activating agents include alkyl- or aryl-sulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide followed by p-toluenesulfonyl chloride to a solution of the 5N-oxide of Formula XIV in a suitable solvent such as chloroform or dichloromethane at ambient temperature.

In step (5) of Reaction Scheme II, the benzyl group of benzyloxyalkyl-substituted 1H-imidazo[4,5-c][1,5]naphthyridin-4-amine of Formula XV is cleaved to provide a hydroxyalkyl-substituted 1H-imidazo[4,5-c][1,5]naphthyridin-4-amine of Formula Ic, which is a subgenus of Formula I. The cleavage is conveniently carried out on a Parr apparatus under hydrogenolysis conditions using a suitable heterogeneous catalyst such as palladium on carbon in a solvent such as ethanol. The reaction can be carried out at ambient temperature.

Reaction Scheme II

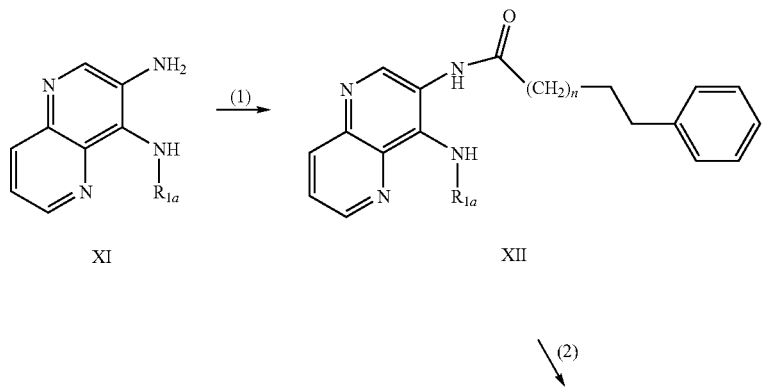

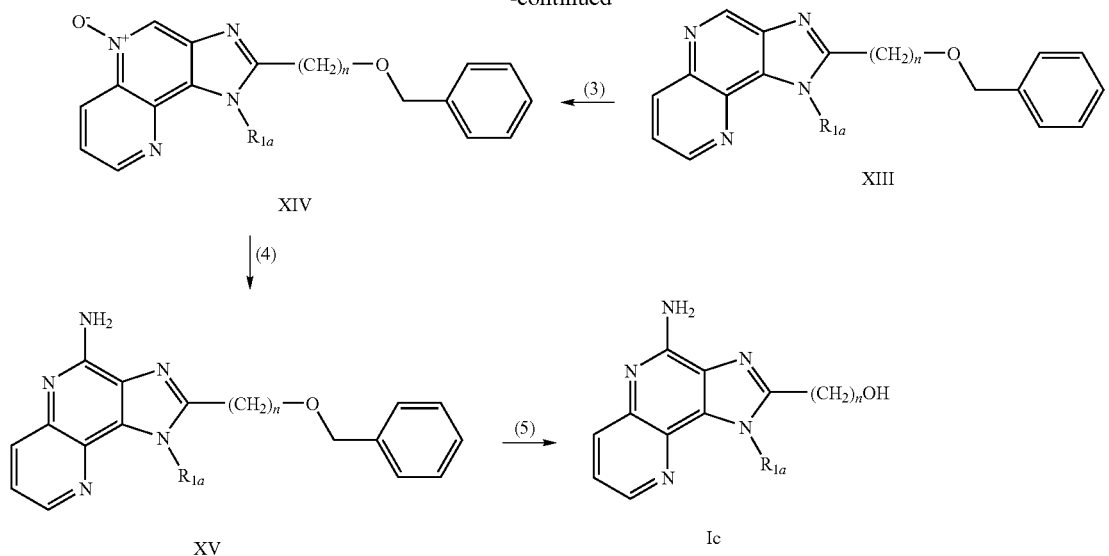

XIV → (4) → XV

XIII → (3)

Ic ← (5)

In some embodiments, compounds of the invention can be prepared according to Reaction Scheme III, wherein $R_1$, $G_1$, and n are as defined above. Compounds of Formula I can be prepared according to the methods described above. The amino group of a compound of Formula I can be converted by conventional methods to a functional group such as an amide, carbamate, urea, amidine, or another hydrolyzable group. A compound of this type can be made by the replacement of a hydrogen atom in an amino group with a group such as —C(O)—R', α-aminoacyl, α-aminoacyl-α-aminoacyl, —C(O)—O—R', —C(O)—N(R")R', —C(=NY')—R', —CH(OH)—C(O)—OY', —CH(OC$_{1-4}$ alkyl)Y$_0$, —CH$_2$Y$_1$, and —CH(CH$_3$)Y$_1$; wherein R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—N$_2$, —O—CH$_2$—C(O)—NH$_2$, —NH$_2$, and —S(O)$_2$—NH$_2$, with the proviso that R" can also be hydrogen; each α-aminoacyl is an α-aminoacyl group derived from an α-amino acid selected from the group consisting of racemic, D-, and L-amino acids; Y$_1$ is selected from the group consisting of hydrogen, $C_{1-6}$ alkyl, and benzyl; Y$_0$ is selected from the group consisting of $C_{1-6}$ alkyl, carboxy-$C_{1-6}$ alkylenyl, amino-$C_{1-4}$ alkylenyl, mono-N—$C_{1-6}$ alkylamino-$C_{1-4}$ alkylenyl, and di-N,N—$C_{1-6}$ alkylamino-$C_{1-4}$ alkylenyl; and Y$_1$ is selected from the group consisting of mono-N—$C_{1-6}$ alkylamino, di-N,N—$C_{1-6}$ alkylamino, morpholin-4-yl, piperidin-1-yl, pyrrolidin-1-yl, and 4-$C_{1-4}$ alkylpiperazin-1-yl. Particularly useful compounds of Formula II are amides derived from carboxylic acids containing one to ten carbon atoms, amides derived from amino acids, and carbamates containing one to ten carbon atoms. The reaction can be carried out, for example, by combining a compound of Formula I with a chloroformate or acid chloride, such as ethyl chloroformate or acetyl chloride, in the presence of a base such as triethylamine in a suitable solvent such as dichloromethane at ambient temperature.

Alternatively, the hydroxy group on a compound of Formula I can be protected using a suitable silyl group such as tert-butyl dimethylsilyl using conventional methods. The $G_1$ group may then be installed using conventional methods followed by the removal of the hydroxy protecting group under acidic conditions to provide a compound of Formula II.

Reaction Scheme III

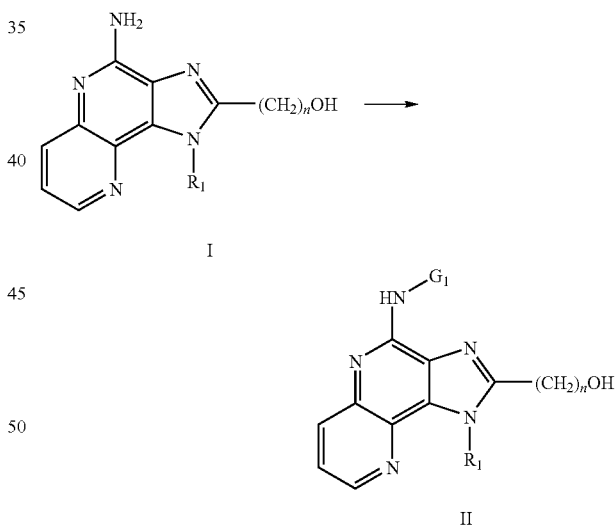

In some embodiments, compounds of the invention can be prepared according to Reaction Scheme IV, wherein $R_1$, $G_2$, and n are as defined above. Compounds of Formula I can be prepared according to the methods described above. The hydrogen atom of the alcohol group of a compound of Formula I can be replaced using conventional methods with a group such as X$_2$—C(O)—R', α-aminoacyl, α-aminoacyl-α-aminoacyl, —X$_2$—C(O)—O—R', and —C(O)—N(R")R'; wherein X$_2$ is selected from the group consisting of a bond; —CH$_2$—O—; —CH(CH$_3$)—O—; —C(CH$_3$)$_2$—O—; and, in the case of —X$_2$—C(O)—O—R', —CH$_2$—NH—; R' and R" are independently selected from the group consisting of $C_{1-10}$ alkyl, $C_{3-7}$ cycloalkyl, phenyl, benzyl, and 2-phenylethyl, each of which may be unsubstituted or substituted by one or more substituents independently selected from the group consisting of halogen, hydroxy, nitro, cyano, carboxy, $C_{1-6}$ alkyl, $C_{1-4}$ alkoxy, aryl, heteroaryl, aryl-$C_{1-4}$ alkylenyl, heteroaryl-$C_{1-4}$ alkylenyl, halo-$C_{1-4}$ alkylenyl, halo-$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen; and each α-aminoacyl is an α-aminoacyl group derived from an α-amino acid selected from the group consisting of racemic, D-, and L-amino acids. Particularly useful compounds of Formula III are esters made from carboxylic acids containing one to six carbon atoms, unsubstituted or substituted benzoic acid esters, or esters made from naturally occurring amino acids. For example, the reaction can be carried out by treating a compound of Formula I with a carboxylic acid or amino acid under Mitsunobu reaction conditions by adding triphenylphosphine and a carboxylic acid to a solution or suspension of a compound of Formula I in a suitable solvent such as tetrahydrofuran and then slowly adding diisopropyl azodicarboxylate. The reaction can be run at a sub-ambient temperature such as 0° C.

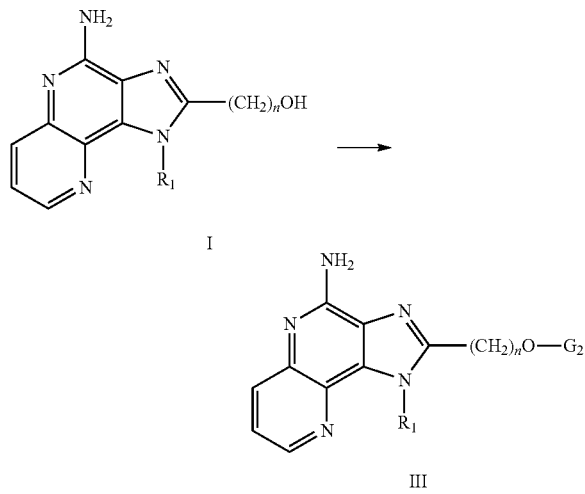

Reaction Scheme IV

In some embodiments, compounds of the invention can also be prepared using the synthetic methods described in the EXAMPLES below.

Pharmaceutical Compositions and Biological Activity

Pharmaceutical compositions of the invention contain a therapeutically effective amount of a compound or salt described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Cytokine induction can include preferentially inducing the biosynthesis of IFN-α. The exact amount of compound or salt used in a pharmaceutical composition of the invention will vary according to factors known to those of skill in the art, such as the physical and chemical nature of the compound or salt, the nature of the carrier, and the intended dosing regimen.

In some embodiments, the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject.

In other embodiments, the compositions of the invention will contain sufficient active ingredient or prodrug to provide a dose of, for example, from about 0.01 mg/m$^2$ to about 5.0 mg/m$^2$, computed according to the Dubois method, in which the body surface area of a subject (m$^2$) is computed using the subject's body weight: m$^2$=(wt kg$^{0.425}$×height cm$^{0.725}$)×0.007184, although in some embodiments the methods may be performed by administering a compound or salt or composition in a dose outside this range. In some of these embodiments, the method includes administering sufficient compound to provide a dose of from about 0.1 mg/m$^2$ to about 2.0 mg/m$^2$ to the subject, for example, a dose of from about 0.4 mg/m$^2$ to about 1.2 mg/m$^2$.

A variety of dosage forms may be used, such as tablets, lozenges, capsules, parenteral formulations (e.g., intravenous formulations), syrups, creams, ointments, aerosol formulations, transdermal patches, transmucosal patches and the like. These dosage forms can be prepared with conventional pharmaceutically acceptable carriers and additives using conventional methods, which generally include the step of bringing the active ingredient into association with the carrier.

The compounds or salts of the invention can be administered as the single therapeutic agent in the treatment regimen, or the compounds or salts described herein may be administered in combination with one another or with other active agents, including additional immune response modifiers, antivirals, antibiotics, antibodies, proteins, peptides, oligonucleotides, etc.

Compounds or salts of the invention have been shown to induce the production of certain cytokines in experiments performed according to the tests set forth below. These results indicate that the compounds or salts are useful for modulating the immune response in a number of different ways, rendering them useful in the treatment of a variety of disorders. The compounds or salts of the invention are especially useful as immune response modifiers due to their ability to preferentially induce interferon-α, thus providing a benefit over compounds that also induce pro-inflammatory cytokines (e.g. TNF-α) or that induce pro-inflammatory cytokines at higher levels. While interferon-α and pro-inflammatory cytokines are beneficial in treating certain conditions, interferon-α preferentially induced is believed to be better tolerated by patients, because the significantly lower levels of pro-inflammatory cytokines can result in fewer or less severe adverse side effects experienced by patients. For example, if a subject is treated for a disease (e.g., hepatitis C, metastatic cancer) with a compound that induces significant levels of pro-inflammatory cytokines, while treating the disease, the compound may also cause side effects, such as severe and/or widespread inflammation, tissue destruction, or emesis, that render the subject unable or unwilling to receive the treatment. Alternatively, if a subject is treated with a compound that preferentially induces interferon-α then the compound may treat the disease with less risk of adverse side effects from pro-inflammatory cytokines such as TNF-α. Therefore, by maintaining the ability to treat a condition and reducing adverse side effects, compounds that preferentially induce IFN-α provide an advantage over compounds that would also induce pro-inflammatory cytokines, such as TNF-α, at higher levels.

The ability of the compounds or salts of the invention to preferentially induce the biosynthesis of IFN-α may be particularly advantageous when administered systemically, since adverse side effects, including for example widespread inflammation, may be reduced or even eliminated. Compounds of the invention may be administered systemically in a number of ways, including but not limited to oral and intravenous administration.

Cytokines whose biosynthesis may be induced by compounds or salts of the invention include IFN-α, IP-10, MCP-1, and a variety of other cytokines. In some instances, cytokines such as TNF-α, IL-12 may be induced, albeit at significantly reduced levels. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt of the invention to the animal. The animal to which the compound or salt is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, the compounds or salts may cause maturation of dendritic cells or proliferation and differentiation of B-lymphocytes.

Whether for prophylaxis or therapeutic treatment of a disease, and whether for effecting innate or acquired immunity, the compound or salt or composition may be administered alone or in combination with one or more active components as in for example, a vaccine adjuvant. When administered with other components, the compound or salt or composition and other component or components may be administered separately; together but independently such as in a solution; or together and associated with one another such as (a) covalently linked or (b) non-covalently associated, e.g., in a colloidal suspension.

Conditions for which compounds or salts or compositions identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagibsum), a picormavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus, or Bordetella;

(c) other infectious diseases, such as chlamydia, fungal diseases including but not limited to candidiasis, aspergillosis, histoplasmosis, cryptococcal meningitis, or parasitic diseases including but not limited to malaria, pneumocystis carnii pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to acute myeloid leukemia, acute lymphocytic leukemia, chronic myeloid leukemia, chronic lymphocytic leukemia, multiple myeloma, Hodgkin's lymphoma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia greata; and (g) diseases associated with wound repair such as, for example, inhibition of keloid formation and other types of scarring (e.g., enhancing wound healing, including chronic wounds).

Additionally, a compound or salt identified herein may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneurnococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts identified herein may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An animal may also be vaccinated by administering an effective amount of a compound or salt described herein, as a vaccine adjuvant. In one embodiment, there is provided a method of vaccinating an animal comprising administering an effective amount of a compound or salt described herein to the animal as a vaccine adjuvant.

An amount of a compound or salt effective to induce cytokine biosynthesis is an amount sufficient to cause one or more cell types, such as dendritic cells and B-cells to produce an amount of one or more cytokines such as, for example, IFN-α, IP-10, and MCP-1 that is increased (induced) over a background level of such cytokines. The precise amount will vary according to factors known in the art but is expected to be a dose of about 100 ng/kg to about 50 mg/kg, preferably about 10 μg/kg to, about 5 mg/kg. In other embodiments, the amount is expected to be a dose of, for example, from about 0.01 mg/m$^2$ to about 5.0 mg/m$^2$, (computed according to the Dubois method as described above) although in some embodiments the induction of cytokine biosynthesis may be performed by administering a compound or salt in a dose outside this range. In some of these embodiments, the method includes administering sufficient compound or salt or composition to provide a dose of from about 0.1 mg/m$^2$ to about 2.0 mg/m$^2$ to the subject, for example, a dose of from about 0.4 mg/m$^2$ to about 1.2 mg/m$^2$.

The invention provides a method of treating a disease which is responsive to the induction of cytokine biosynthesis, particularly the preferential induction of IFN-α, including a method of treating a viral infection in an animal and a method of treating a neoplastic disease in an animal, comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound or salt effective to treat a neoplastic condition is an amount that will cause a reduction in tumor size or in the number of tumor foci. Again, the precise amount will vary according to factors known in the art but is expected, to be a dose of about 100 ng/kg to about 50 mg/kg, preferably about 10 μg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments either of these methods may be performed by administering a compound or salt in a dose outside this range. In some of these embodiments, the method includes administering sufficient compound or salt to provide a dose of from about 0.1 mg/m$^2$ to about 2.0 mg/m$^2$ to the subject, for example, a dose of from about 0.4 mg/m$^2$ to about 1.2 mg/m$^2$.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

Objects and advantages of this invention are further illustrated by the following examples, but the particular materials and amounts thereof recited in these examples, as well as other conditions and details, should not be construed to unduly limit this invention.

EXAMPLES

In the examples below normal high performance flash chromatography (prep HPLC) was carried out using a COMBIFLASH system (an automated high-performance flash purification product available from Teledyne Isco, Inc., Lincoln, Nebr., USA) or a HORIZON HPFC system (an automated high-performance flash purification product available from Biotage, Inc, Charlottesville, Va., USA). The eluent used for each purification is given in the example. In some chromatographic separations, the solvent mixture 80/18/2 v/v/v chloroform/methanol/concentrated ammonium hydroxide (CMA) was used as the polar component of the eluent. In these separations, CMA was mixed with chloroform in the indicated ratio.

Example 1

N-[2-(4-Amino-2-hydroxymethyl-1H-imidazo[4,5-c][1,5]naphthyridin-1-yl)-1,1-dimethylethyl]cyclohexanecarboxamide

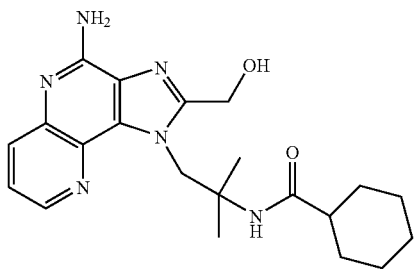 [SMILES: CC(C)(Cn1c(CO)nc2c(N)nc3cccnc3c21)NC(=O)C1CCCCC1]

Part A 1,2-Diamino-2-methylpropane (8.4 mL, 80.0 mmol) was added to a chilled (0° C.), solution of 4-chloro-3-nitro[1,5]naphthyridine (15.2 g, 72.7 mmol) and triethylamine (20.2 mL, 145 mmol) in dichloromethane (350 mL). The reaction mixture was stirred overnight and then concentrated under reduced pressure. The residue was combined with water (300 mL) and heated at reflux with stirring for 1 hour. The reaction mixture was cooled and filtered. The isolated solid was washed with water and then dried under high vacuum to provide 18.5 g of $N^1$-(3-nitro[1,5]naphthyridin-4-yl)-2-methylpropane-1,2-diamine as a bright yellow powder.

Part B

Under a nitrogen atmosphere, a solution of sodium hydroxide (3.12 g, 78.0 mmol) in water (50 mL) was added to a solution of the material from Part A (18.5 g, 70.9 mmol) in tetrahydrofuran (200 mL). A solution of di-tert-butyl dicarbonate (17.0 g, 78.0 mmol) in tetrahydrofuran (100 mL) was added dropwise over a period of 30 minutes. Two (2) days later additional di-tert-butyl dicarbonate (2.0 g) was added. The reaction mixture was stirred for another 8 hours and then concentrated under reduced pressure. The residue was dissolved in ethyl acetate (250 mL), washed sequentially with water (×2) and brine, dried over sodium sulfate, filtered, and then concentrated under reduced pressure. The residue was dissolved in warm 1/1 ethyl acetate/hexanes. The solution was allowed to slowly cool. The resulting precipitate was isolated by filtration and washed with hexanes to provide 17.7 g of tert-butyl N-{2-[(3-nitro[1,5]naphthyridin-4-yl)amino]-1,1-dimethylethyl}carbamate as a bright yellow crystalline solid.

Part C

A Parr vessel was charged with a solution of tert-butyl N-{2-[(3-nitro[1,5]naphthyridin-4-yl)amino]-1,1-dimethylethyl}carbamate (12.62 g, 34.9 mmol) in acetonitrile (100 mL) and 5% Pt/C (2.00 g). The vessel was placed under hydrogen pressure (50 psi, 3.4×10$^5$ Pa) until hydrogen uptake ceased. The reaction mixture was filtered through a layer of CELITE filter aid and the filter cake was rinsed with acetonitrile. The filtrate was concentrated under reduced pressure to provide 11.07 g of tert-butyl N-{2-[(3-amino[1,5]naphthynidin-4-yl)amino]-1,1-dimethylethyl]carbamate as a bright yellow foam.

Part D

Under a nitrogen atmosphere, a solution of the material from Part C (11.07 g, 33.4 mmol) in dichloromethane (330 mL) was cooled to 0° C. Triethylamine (5.11 mL, 36.7 mmol) and ethoxyacetyl chloride (3.70 mL, 36.7 mmol) were added sequentially. The reaction mixture was stirred overnight while warming to ambient temperature and then concentrated under reduced pressure. The residue was dissolved in ethanol (300 mL). Triethylamine (16 mL) was added and the solution was heated at reflux under a nitrogen atmosphere over the weekend. The reaction mixture was allowed to cool to ambient temperature and then concentrated under reduced pressure. The residue was dissolved in dichloromethane (250 mL), washed sequentially with water and brine, dried over magnesium sulfate, filtered, and then concentrated under reduced pressure. The residue was purified by flash chromatography (6×12 cm silica gel column eluting with ethyl acetate) to provide 11.5 g of a purple foam. This material was purified by flash chromatography (eluting with 2.5% methanol in chloroform) to provide 10.07 g of tert-butyl N-[2-(2-ethoxymethyl-1H-imidazo[4,5-c][1,5]naphthyridin-1-yl)-1,1-dimethylethyl]carbamate a purple foam.

Part E

3-Chloroperoxybenzoic acid (7.50 g of 57-86%) was added to a solution of the material from Part D in dichloromethane (250 mL). After 2.5 hours, additional 3-chloroperoxybenzoic acid (250 mg) was added and the reaction mixture was; stirred for 1.5 hours. The reaction mixture was washed sequentially with 1% sodium carbonate (4×75 mL), water, and brine, dried over sodium sulfate, filtered, and then concentrated under reduced pressure to provide 10.32 g of tert-butyl N-[2-(2-ethoxymethyl-5N-oxide-1H-imidazo[4,5-c][1,5]naphthyridin-1-yl)-1,1-dimethylethyl]carbamate as a purple foam.

Part F

Concentrated ammonium hydroxide (20 mL) was added to a solution of the material from Part E (10.32 g, 24.9 mmol) in dichloromethane (200 mL). Toluenesulfonyl chloride (5.02 g, 26.3 mmol) was added in small portions over a period of 2 minutes. The reaction mixture was stirred for 2 hours and then diluted with water. The layers were separated. The organic layer was washed sequentially with 1% sodium carbonate (×3), water, and brine, dried over sodium sulfate, filtered, and then concentrated under reduced pressure. The residue was purified by flash chromatography (6×15 cm column of silica gel, eluting with 10% CMA in chloroform) to provide about 8 g of a purple foam. The foam was dissolved in ethanol, combined with activated charcoal (2 g), heated at reflux for 15 minutes, filtered, and then concentrated under reduced pressure to provide 7.59 g of tert-butyl N-[2-(4-amino-2-ethoxymethyl-1H-imidazo[4,5-c][1,5]naphthyridin-1-yl)-1,1-dimethylethyl]carbamate as a violet foam.

Part G

A solution of hydrochloric acid in ethanol (17 mL of 4.3 M) was added to a solution of the material from Part F in ethanol (100 mL). The reaction mixture was heated at 90° C. for 2 hours, allowed to cool, and then concentrated under reduced pressure. The residue was dissolved in water (100 mL) and extracted with chloroform (2×25 mL). The extracts were discarded. The aqueous was made basic with concentrated ammonium hydroxide and then extracted with chloroform (4×50 mL). The combined extracts were dried over sodium sulfate, filtered, and then concentrated under reduced pressure. The residue was crystallized from ethyl acetate/hexanes (about 100 mL). The solid was isolated by filtration, rinsed with cold 20% ethyl acetate in hexanes, and dried under vacuum. A second crop was obtained and combined with the first crop to provide 3.82 g of 1-(2-amino-2-methylpropyl)-2-ethoxymethyl-1H-imidazo[4,5-c][1,5]naphthyridin-4-amine as a gray crystalline solid.

Part H

Under a nitrogen atmosphere, a solution of 1-(2-amino-2-methylpropyl)-2-ethoxymethyl-1H-imidazo[4,5-c][1,5]naphthyridin-4-amine (1.552 g, 4.94 mmol) in dichloromethane (50 mL) was cooled to 0° C. Triethylamine (1.38 mL, 9.92 mmol) and cyclohexylcarbonyl chloride (661 µL, 4.94 mmol) were added sequentially. Two (2) days later the reaction mixture was cooled and additional cyclohexylcarbonyl chloride (40 µL) was added. The reaction mixture was stirred overnight and then diluted with saturated sodium bicarbonate and dichloromethane (50 mL). The layers were separated. The organic layer was washed sequentially with water (×2) and brine, dried over sodium sulfate, filtered, and then concentrated under reduced pressure. The residue was purified by flash chromatography (4×13 cm silica gel column, eluting with 3% methanol in chloroform). The purified material was dissolved in refluxing propyl acetate (80 mL) with the aid of methanol, the methanol was boiled off, and the solution was allowed to slowly cool. The resulting precipitate was isolated by filtration, rinsed with cold propyl acetate, and dried under high vacuum at 70° C. to provide 1.37 g of N-[2-(4-amino-2-ethoxymethyl-1H-imidazo[4,5-c][1,5]naphthyridin-1-yl)-1,1-dimethylethyl]cyclohexanecarboxamide as a colorless crystalline solid, mp 210-211° C. Anal. calcd for $C_{23}H_{32}N_6O_2$: % C, 65.07; % H, 7.60; % N, 19.80. Found: % C, 64.93; % H, 7.76; % N, 19.97.

Part I

Boron tribromide (1.24 mL of 1 M in dichloromethane) was added dropwise to a chilled (ice bath) suspension of N-[2-(4-amino-2-ethoxymethyl-1H-imidazo[4,5-c][1,5]naphthyridin-1-yl)-1,1-dimethylethyl]cyclohexanecarboxamide (500 mg, 1.18 mmol) in dichloromethane (15 mL). The reaction mixture was allowed to slowly warm to ambient temperature and then stirred over the weekend. Additional boron tribromide (1 mL) was added and the reaction mixture was stirred for 24 hours. The reaction was quenched with methanol (10 mL) and then concentrated under reduced pressure. The residue was combined with hydrochloric acid (15 mL of 6 M), heated to 50° C., and stirred for 2 hours. The resulting solution was cooled to ambient temperature and then neutralized (pH 7) with 10% sodium hydroxide. The resulting gummy precipitate was extracted with chloroform (3×15 mL). The combined extracts were washed with brine (15 mL), dried over sodium sulfate, filtered, and then concentrated under reduced pressure to provide an off white solid. This material was purified by prep HPLC (HORIZON HPFC system, eluting with a gradient of 10-50% CMA in chloroform) to provide a white solid. The solid was triturated with hot acetonitrile, allowed to cool, isolated by filtration, and dried under vacuum to provide 233 mg of N-[2-(4-amino-2-hydroxymethyl-1H-imidazo[4,5-c][1,5]naphthyridin-1-yl)-1,1-dimethylethyl]cyclohexanecarboxamide as a fine white solid, mp 230-232° C.; $^1$H NMR (300 MHz, DMSO-$d_6$, 350 K) δ 8.53 (dd, J=4.3, 1.6 Hz, 1H), 7.95 (dd, J=8.4, 1.5 Hz, 1H), 7.87 (s, 1H), 7.47 (dd, J=8.4, 4.4 Hz, 1H), 6.55 (s, 2H), 5.31 (s, 1H), 5.15 (s, 2H), 4.79 (d, J=5.4 Hz, 2H), 1.90-1.80 (m, 1H), 1.67-1.43 (m, 5H), 1.31 (s, 6H), 1.24-1.02 (m, 5H); $^{13}$C NMR (75 MHz, DMSO-$d_6$) δ 175.9, 154.6, 152.8, 142.8, 140.8, 134.2, 133.5, 133.3, 129.3, 122.5, 56.4, 55.0, 52.3, 44.9, 29.4, 25.7, 25.6, 24.9; MS (ESI) m/z 397 (M+H)+; Anal. Calcd for $C_{21}H_{29}N_6O_2$: C, 63.62; H, 7.12; N, 21.20. Found: C, 63.77; H, 7.34; N, 21.50.

Example 2

N-[2-(4-Amino-2-hydroxymethyl-1H-imidazo[4,5-c][1,5]naphthyridin-1-yl)-1,1-dimethylethyl]methanesulfonamide

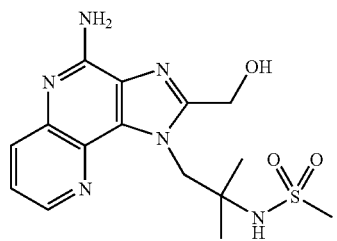 [SMILES: CC(C)(Cn1c(CO)nc2c(N)nc3cccnc3c21)NS(C)(=O)=O]

Part A

Under a nitrogen atmosphere, a solution of 1-(2-amino-2-methylpropyl)-2-ethoxymethyl-1H-imidazo[4,5-c][1,5]naphthyridin-4-amine (1.588 g, 5.06 mmol) in dichloromethane (50 mL) was cooled to 0° C. Triethylamine (1.41 μL, 10.12 mmol) and methanesulfonyl chloride (392 μL, 5.06 mmol) were added sequentially. The reaction mixture was allowed to slowly warm to ambient temperature overnight. Additional methanesulfonyl chloride (40 μL) was added and the reaction mixture was stirred at ambient temperature for an additional 5 hours. The reaction mixture was diluted with aqueous saturated sodium bicarbonate and the layers were separated. The organic layer was washed sequentially with water and brine, dried over sodium sulfate, filtered, and then concentrated under reduced pressure. The residue was purified by flash chromatography (4×15 cm silica gel column, eluting with a gradient of 5-7.5% methanol in chloroform). The purified material was dissolved in refluxing propyl acetate (80 mL) with the aid of methanol, the methanol was boiled off, and the solution was allowed to slowly cool. The resulting precipitate was isolated by filtration, rinsed with cold propyl acetate, and dried under high vacuum at 70° C. to provide 1.35 g of N-[2-(4-amino-2-ethoxoxymethyl-1H-imidazo[4,5-c][1,5]naphthyridin-1-yl)-1,1-dimethylethyl]methanesulfonamide as colorless needles, mp 209-210° C. Anal. calcd for $C_{17}H_{24}N_6O_3S$: % C, 52.02; % H, 6.16; % N, 21.41. Found: % C, 52.09; % H, 6.35; % N, 21.60.

Part B

Boron tribromide (1.34 mL of 1 M in dichloromethane) was added dropwise to a chilled (ice bath) suspension of N-[2-(4-amino-2-ethoxoxymethyl-1H-imidazo[4,5-c][1,5]naphthyridin-1-yl)-1,1-dimethylethyl]methanesulfonamide (500 mg, 1.27 mmol) in dichloromethane (15 mL). The reaction mixture was allowed to slowly warm to ambient temperature and then stirred over the weekend. Additional boron tribromide (1.5 mL) was added and the reaction mixture was stirred for 4 hours. Additional boron tribromide (1.5 mL) was added and the reaction mixture was stirred overnight. The reaction was quenched with methanol (15 mL) and then concentrated under reduced pressure. The residue was combined with hydrochloric acid (15 mL of 6 M), heated to 50° C., and stirred for 2 hours. The resulting solution was cooled to ambient temperature and then neutralized (pH 7) with 10% sodium hydroxide. The resulting precipitate was isolated by filtration and rinsed with water to provide a white solid. This material was purified by prep HPLC(HORIZON HPFC system, eluting with a gradient of 10-50% CMA in chloroform) to provide a white solid. This material was recrystallized from acetonitrile and dried in a vacuum oven to provide 103 mg of N-[2-(4-amino-2-hydroxymethyl-1H-imidazo[4,5-c][1,5]naphthyridin-1-yl)-1,1-dimethylethyl]methanesulfonamide as a white crystalline solid, mp 268-271° C.; $^1$H NMR (300 MHz, DMSO-$d_6$) δ 8.50 (dd, J=4.4, 1.6 Hz, 1H), 7.95 (dd, J=8.4, 1.5 Hz, 1H), 7.90 (s, 1H), 7.48 (dd, J=8.4, 4.4 Hz, 1H), 6.91 (s, 2H), 5.6.2 (t, J=5.9 Hz, 1H), 5.10 ((bs, 2H), 4.92 (s, 2H), 2.87 (s, 3H), 1.35 (s, 6H); $^{13}$C NMR (75. MHz, DMSO-$d_6$) δ 154.2, 152.3, 142.3, 140.3, 133.4, 133.1, 132.9, 128.8, 122.1, 57.2, 56.4, 54.3, 44.1, 25.1; MS (APCI) m/z 365 (M+H)+; Anal. Calcd for $C_{15}H_{20}N_6O_3S$: C, 49.44; H, 5.53; N, 23.06. Found: C, 49.48; H, 5.40; N, 23.31.

Example 3

N-{4-{4-Amino-2-(2-hydroxyethyl)-1H-imidazo[4,5-c][1,5]naphthyridin-1-yl]butyl}methanesulfonamide

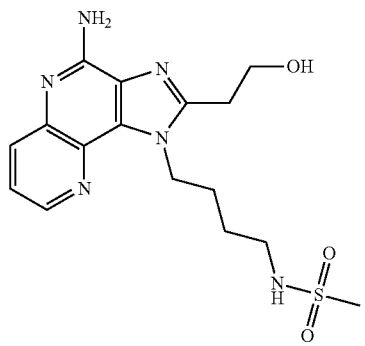 [SMILES: CS(=O)(=O)NCCCCn1c(CCO)nc2c(N)nc3cccnc3c21]

Part A

3-Methoxypropionyl chloride (2.7 g, 22 mmol) was added dropwise to a chilled (ice bath) solution of tert-butyl N-{4-[(3-amino[1,5]naphthyridin-4-yl)amino]butyl}carbamate 6.7 g, 20 mmol, U.S. Pat. No. 6,194,425, Example 42) in anhydrous pyridine (75 mL). The reaction mixture was heated at 120° C. overnight. The reaction was repeated on the same scale. The reaction mixtures were combined and concentrated under reduced pressure to provide 28 g of crude tert-butyl N-((4-{([3-(3-methoxypropionyl)amino[1,5]naphthyridin-4-yl]amino}butyl))carbamate as a red oil.

Part B

The crude material from Part A was dissolved in pyridine (150 mL). Pyridine hydrochloride (2.1 g) was added and the reaction mixture was heated at reflux overnight. The reaction mixture was concentrated under reduced pressure. The residue; was diluted with dichloromethane and washed with brine. The aqueous layer was extracted with dichloromethane (×4). The combined organics were concentrated under reduced pressure. The residue was purified by prep HPLC (COMBIFLASH system eluting with a gradient of 0-7% methanol in dichloromethane containing 1% ammonium hydroxide) to provide 9.72 g of tert-butyl N-{4-[2-(2-methoxyethyl)-1H-imidazo[4,5-c][1,5]naphthyridin-1-yl]buytl}carbamnate as a brown glassy solid.

Part C

3-Chloroperoxybenzoic acid (7.8 g of 77%) was added in a single portion to a solution of tert-butyl N-{4-[2-(2-methoxyethyl)-1H-imidazo[4,5-c][1,5]naphthyridin-1-yl]
buytl}carbamate (7 g) in dichloroethane (100 mL). The reaction mixture was stirred at ambient temperature for 3 hours. Concentrated ammonium hydroxide (100 mL) was added and the reaction mixture was stirred until a suspension formed. Para-toluenesulfonyl chloride (3.6 g) was added in a single portion. The reaction mixture was stirred at ambient temperature for 2 hours and then diluted with dichloromethane and brine. The organic layer was separated, washed with brine (×2), dried over magnesium sulfate, filtered through a layer of CELITE filter aid, and then concentrated under reduced pressure to provide 8.83 g of crude tert-butyl N-{4-[4-amino-2-(2-methoxyethyl)-1H-imidazo[4,5-c][1,5]naphthyridin-1-yl]buytl}carbamate as a brown solid.

Part D

The material from Part C was diluted with a small amount of dichloromethane and then hydrochloric acid in dioxane (126 mL of 4 M) was slowly added. The reaction mixture was stirred at ambient temperature overnight and then concentrated under reduced pressure. The residue was purified by prep HPLC (COMBIFLASH system eluting with a gradient of 0-7% methanol in dichloromethane containing 1% ammonium hydroxide) to provide 8 g of crude 1-(4-aminobutyl)-2-(2-methoxyethyl)-1H-imidazo[4,5-c][1,5]naphthyridin-4-amine.

Part E

Triethylamine (3.9 mL) was added to a solution of a portion (1.8 g) of the material from Part D in pyridine (20 mL). Methanesulfonyl chloride (485 µL) was added dropwise. The reaction mixture was stirred at ambient temperature for 2 hours, quenched with water (25 mL), and the stirred overnight. The reaction mixture was concentrated under reduced pressure and then diluted with dichloromethane. The organic layer was washed with brine (×2) and then concentrated under reduced pressure. The residue was purified by prep HPLC (COMBIFLASH system eluting with a gradient of 0-5% methanol in dichloromethane containing 1% ammonium hydroxide for 5 minutes and then holding at 5%) to provide 400 mg of N-{4-{4-amino-2-(2-methoxyethyl)-71H-imidazo[4,5-c][1,5]naphthyridin-1-yl]butyl}methanesulfonamide.

Part F

Boron tribromide (2.55 mL of 1 M in dichloromethane) was slowly added to a chilled mixture of the material from Part E in dichloromethane (10 mL). The reaction mixture was stirred at ambient temperature overnight and then concentrated under reduced pressure. The residue was dissolved in methanol, combined with hydrochloric acid (50 mL of 6 M), heated at 50° C. for 2 hours, and concentrated under reduced pressure. The residue was combined with a solution of ammonia in methanol (about 50 mL of 7 M) and then concentrated again. This procedure was repeated 3 times. The residue from the final concentration was purified by prep HPLC (COMBIFLASH system eluting with a gradient of 0-10% methanol in dichloromethane containing 1% ammonium hydroxide for 10 minutes). The combined fractions were concentrated and then distributed onto solid phase-extraction cartridges. The cartridges were eluted with ammonia in methanol (7 M). The resulting material was triturated with hot acetonitrile, cooled, isolated, and then dried in a vacuum oven to provide 111 mg of N-{4-{4-amino-2-(2-hydroxyethyl)-1H-imidazo[4,5-c][1,5]naphthyridin-1-yl]butyl}methanesulfonamide, mp 194-195° C. Anal. calcd for $C_{16}H_{22}N_6O_3S$: % C, 50.78; % H, 5.86; % N, 22.21. Found: % C, 50.83; % H, 6.12; % N, 21.70.

Example 4

N-[2-(4-Amino-2-hydroxymethyl-1H-imidazo[4,5-c][1,5]naphthyridin-1-yl)ethyl]methanesulfonamide

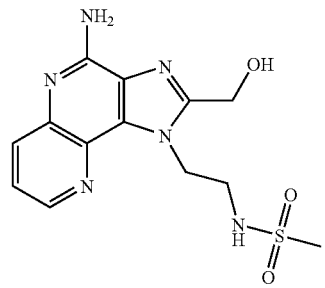 [SMILES: CS(=O)(=O)NCCn1c(CO)nc2c(N)nc3cccnc3c21]

Part A

Methoxyacetyl chloride (5.9 g, 54 mmol) was added dropwise to a chilled (ice bath) solution of tert-butyl N-{2-[(3-amino[1,5]naphthyridin-4-yl)amino]ethyl}carbamate (15.0 g, 49.5 mmol, U.S. Pat. No. 6,194,425, Example 87) in anhydrous pyridine (100 mL). The reaction mixture was heated at reflux until analysis by liquid chromatography/mass spectroscopy (LCMS) indicated that the reaction was complete. The reaction mixture was concentrated under reduced pressure. The residue was diluted with ethanol (100 mL), combined with potassium carbonate solution (200 mL of 2 M), and heated at reflux for 4 hours. The reaction mixture was cooled and then concentrated under reduced pressure. The residue was partitioned between water and dichloromethane. The aqueous layer was extracted with dichloromethane. The combined organics were dried over magnesium sulfate, filtered, and then concentrated under reduced pressure to provide 14 g of tert-butyl N-[2-(2-methoxymethyl-1H-imidazo[4,5-c][1,5]naphthyridin-1-yl)ethyl]carbamate.

Part B

Using the method of Example 3 Part C, the material from Part A was oxidized and then aminated to provide 17 g of crude tert-butyl N-[2-(4-amino-2-methoxymethyl-1H-imidazo[4,5-c][1,5]naphthyridin-1-yl)ethyl]carbamate as a sticky amber solid.

Part C

The material from Part B was dissolved in a mixture of dichloromethane (20 mL) and methanol (5 mL). Hydrochloric acid in dioxane (28 mL of 4 M) was added. More dichloromethane was added to facilitate stirring. The reaction mixture was stirred at ambient temperature overnight and then concentrated under reduced pressure to provide crude 1-(2-aminoethyl)-2-methoxymethyl-1H-imidazo[4,5-c][1,5]naphthyridin-4-amine as an orange solid.

Part D

Triethylamine (35.6 mL) was added to a mixture of the material from Part C and pyridine (100 mL). The reaction mixture was cooled in an ice bath and then methanesulfonyl chloride (4.3 mL) was added dropwise. The reaction mixture was stirred at ambient temperature for 1 hour. Twice, more methanesulfonyl chloride (0.43 mL) was added and the reaction mixture was stirred at ambient temperature for 2 hours. The reaction mixture was partitioned between water and dichloromethane. The aqueous layer was extracted with dichloromethane (×2). The combined organics were dried over magnesium sulfate, filtered through a layer of CELITE filter aid, and then concentrated under reduced pressure to provide 14 g of N-[2-(4-amino-2-methoxymethyl-1H-imidazo[4,5-c][1,5]naphthyridin-1-yl)ethyl]methanesulfonamide.

Part E

Boron tribromide (71.4 mL of 1 M in dichloromethane) was slowly added to a chilled (ice bath) mixture of the material from Part D in dichloromethane (50 mL). The reaction mixture was stirred at ambient temperature for 2 hours. Additional boron tribromide (0.5 eq) was added and the reaction mixture was stirred at ambient temperature overnight. The reaction mixture was concentrated under reduced pressure. The residue was dissolved in methanol, combined with hydrochloric acid (50 mL of 6 M), heated at 50° C. for 2 hours, and concentrated under reduced pressure. The residue was combined with a solution of ammonia in methanol (about 40 mL of 7 M) and then concentrated again. This procedure was repeated 3 times. The residue from the final concentration was purified by prep HPLC (COMBIFLASH system eluting with a gradient of 0-5% methanol in dichloromethane containing 1% ammonium hydroxide with a 10 minute ramp and a 20 minute hold, then with gradient of 6-10% methanol in dichloromethane containing 1% ammonium hydroxide with a 10 minute ramp and a 20 minute hold, and finally with gradient of 11-20% methanol in dichloromethane containing 1% ammonium; hydroxide with a 10 minute ramp and a 20 minute hold) to provide 2.4 g of a brown solid. A small portion of this material was combined with hot acetonitrile containing a small amount of methanol, cooled, and then isolated by filtration. This procedure was carried out 3 times. After the final isolation the material was rinsed with ether and dried in a vacuum oven to provide 75 mg of N-[2-(4-amino-2-hydroxymethyl-1H-imidazo[4,5-c][1,5]naphthyridin-1-yl)ethyl]methanesulfonamide as a beige solid, mp 239-242° C. Anal. calcd for $C_{13}H_{16}N_6O_3S$: % C, 46.42; % H, 4.79; % N, 24.98. Found: % C, 46.35; % H, 4.70; % N, 24.70.

Example 5

N-{2-[4-Amino-2-(2-hydroxyethyl)-1H-imidazo[4,5-c][1,5]naphthyridin-1-yl]ethyl}methanesulfonamide

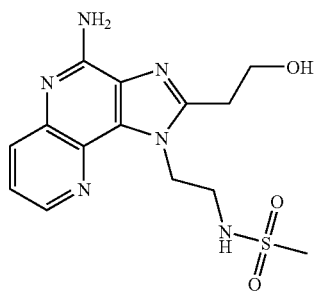 [SMILES: CS(=O)(=O)NCCn1c(CCO)nc2c(N)nc3cccnc3c21]

Part A

Using the general method of Example 4 Part A, tert-butyl N-{2-[(3-amino[1,5]naphthyridin-4-yl)amino]ethyl}carbamate (17.0 g, 56.1 mmol) was reacted with 3-methoxypropionyl chloride (7.5 g, 61.7 mmol) to provide 9.0 g of crude product. Analysis by LCMS indicated that the crude product was about a 1:1 mixture of tert-butyl N-{2-[2-(2-methoxyethyl)-1H-imidazo[4,5-c][1,5]naphthyridin-1-yl]ethyl}carbamate and 1-(2-aminoethyl)-2-(2-methoxyethyl)-1H-imidazo[4,5-c][1,5]naphthyridine.

Part B

Triethylamine (13.8 mL) was added to a mixture of the material from Part A and dichloromethane (70 mL). The resulting solution was chilled in an ice bath. Di-tert-butyl dicarbonate (8.6 g) was added. The reaction mixture was stirred at ambient temperature for 2 hours and then quenched with water. The layers were separated. The organic layer was washed with sodium carbonate, dried over magnesium sulfate, filtered through a layer of CELITE filter aid, and then concentrated under reduced pressure to provide 11 g of tert-butyl N-{2-[2-(2-methoxyethyl)-1H-imidazo[4,5-c][1,5]naphthyridin-1-yl]ethyl}carbamate as a tan solid.

Part C

3-Chloroperoxybenzoic acid (13.2 g of 77%) was added in a single portion to a solution of the material from Part B (11 g, 29.6 mmol) in dichloroethane (50 mL). The reaction mixture was stirred at ambient temperature for 1.5 hours, then diluted with dichloromethane and washed with aqueous ammonium hydroxide (25 mL of concentrated ammonium hydroxide in 250 mL of water). The aqueous layer was extracted with dichloromethane. The combined organics were concentrated under reduced pressure. The residue was dissolved in dichloroethane (100 mL). Concentrated ammonium hydroxide (70 mL) was added and the reaction mixture was stirred until a suspension formed. Para-Toluenesulfonyl chloride (6.2 g, 32.5 mmol) was added in a single portion. The reaction mixture was stirred at ambient temperature for 1.5 hours, then diluted with aqueous sodium bicarbonate and extracted with dichloromethane (×3). The combined organics were dried over magnesium sulfate, filtered through a layer of CELITE filter aid, and then concentrated under reduced pressure. The residue was purified by prep HPLC (COMBIFLASH system eluting with a gradient of 0-5% methanol in dichloromethane containing 1% ammonium hydroxide over 6 minutes and then holding at 5%) to provide 3.5 g of tert-butyl N-{2-[4-amino-2-(2-methoxyethyl)-1H-imidazo[4,5-c][1,5]naphthyridin-1-yl]ethyl}carbamate as an orange solid.

Part D

A solution of hydrochloric acid in dioxane (58 mL of 4 M) was added to a solution of tert-butyl N-{2-[4-amino-2-(2-methoxyethyl)-1H-imidazo[4,5-c][1,5]naphthyridin 1-yl]ethyl}carbamate (3 g) in a small amount of dichloromethane/methanol. The reaction; mixture was stirred overnight at ambient temperature and then concentrated under reduced pressure to provide 3.7 g of crude 1-(2-aminoethyl)-2-(2-methoxyethyl)-1H-imidazo[4,5-c][1,5]naphthyridine-4-amine hydrochloride.

Part E

Using the general method of Example 4 Part D, a portion (1.1 g) of the material from Part D was reacted with methanesulfonyl chloride (322 mL) to provide 1.0 g of N-{2-[4-amino-2-(2-methoxyethyl)-1H-imidazo[4,5-c][1,5]naphthyridin-1-yl]ethyl}methanesulfonamide as a red solid.

Part F

Boron tribromide (7 mL of 1 M in dichloromethane) was slowly added to a chilled (ice bath) mixture of the material from Part E in dichloromethane (25 mL). The reaction mixture was stirred at ambient temperature overnight and then concentrated under reduced pressure. The residue was dissolved in methanol, combined with hydrochloric acid (50 mL of 6 M), heated at 50° C. for 2 hours, and concentrated under reduced pressure. The residue was combined with a solution of ammonia in methanol (about 30 mL of 7 M) and then concentrated again. This procedure was repeated 3 times. The residue from the final concentration was purified by prep HPLC (COMBIFLASH system eluting with a gradient of 0-10% methanol in dichloromethane containing 1% ammonium hydroxide). The residue was combined with hot acetonitrile, cooled, and the acetonitrile was decanted off. This procedure was carried out 3 times. The material was isolated by filtration, rinsed with ether and dried in a vacuum oven to provide 950 mg of N-{2-[4-amino-2-(2-hydroxyethyl)-1H-imidazo[4,5-c][1,5]naphthyridin-1-yl]ethyl}methanesulfonamide, mp 136-138° C. Anal. calcd for $C_{14}H_{18}N_6O_3S$: % C, 47.99; % H, 5.18; % N, 23.98. Found: % C, 47.69; % H, 5.36; % N, 23.77.

Example 6

1-(4-Amino-2-hydroxymethyl-1H-imidazo[4,5-c][1,5]naphthyridin-1-yl)-2-methylpropan-2-ol

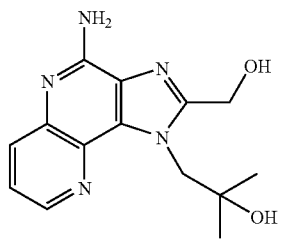 [SMILES: CC(C)(O)Cn1c(CO)nc2c(N)nc3cccnc3c21]

Part A

Under a nitrogen atmosphere, 1-amino-2-methylpropan-2-ol (25.5 g, 0.28 mol) was added over a period of 30 minutes to a solution of 4-chloro-3-nitro[1,5]naphthyridine (54.5 g, 0.26 mol) in dichloromethane (1 L). A water bath was used to control the exotherm and maintain the temperature of the reaction at or below 27° C. The reaction mixture was stirred at ambient temperature overnight. The resulting precipitate (crop 1) was isolated by filtration. The filtrate was concentrated under reduced pressure to provide crop 2. The two crops were slurried separately with de-ionized water for 2 hours and then isolated by filtration. Crop 1: 40.53 g of 2-methyl-2-[(3-nitro[1,5]naphthyridin-4-yl)amino]propan-2-ol as a yellow solid. Crop 2: tan solid. Crop 2 was dissolved in dichloromethane and loaded onto an alumina column. The column was eluted first with 1% methanol in dichloromethane and then with acetone. The combined eluents were concentrated under reduced pressure. The residue was recrystallized from ethanol (10 mL/g) to provide 6.95 g of 2-methyl-1-[(3-nitro[1,5]naphthyridin-4-yl)amino]propan-2-ol.

Part B

A Parr vessel was charged with 2-methyl-1-[(3-nitro[1,5]naphthyridin-4-yl)amino]propan-2-ol (44.12 g, 0.17 mol), 5% Pt/C (4.4 g) and isopropyl alcohol (890 mL). The vessel was placed under hydrogen pressure (35 psi, 2.4×1 Pa) until hydrogen uptake ceased. The reaction mixture was filtered through a layer of filter aid. The filter cake was rinsed with additional isopropyl alcohol. The filtrate was concentrated under reduced pressure to provide 1-[(3-amino[1,5]naphthyridin-4-yl)amino]-2-methylpropan-2-ol as a thick oil.

Part C

Under a nitrogen atmosphere, ethoxyacetyl chloride (19.1 g, 0.156 mol) was added over a period of 12 minutes to a mixture of 1-[(3-amino[1,5]naphthyridin-4-yl)amino]-2-methylpropan-2-ol (28.95 g, 0.125 mol) in pyridine (300 mL). The reaction mixture was stirred at ambient temperature for 4 hours and then at reflux for 4 hours. The reaction mixture was allowed to cool to ambient temperature overnight and then concentrated under high vacuum. The residue was dissolved in 5% potassium carbonate (200 mL) and then extracted with dichloromethane (200 mL). The extract was filtered to remove some insoluble material, dried over magnesium sulfate, filtered, and then concentrated under high vacuum. The residue was dissolved in dichloromethane (150 mL) and eluted through a short column of alumina. The eluent was concentrated under reduced pressure and air dried to provide 31.9 g of 1-(2-ethoxymethyl-1H-imidazo[4,5-c][1,5]naphthyridin-1-yl)-2-methylpropan-2-ol.

Part D

A flask containing a solution of 1-(2-ethoxymethyl-1H-imidazo[4,5-c][1,5]naphthyridin-1-yl)-2-methylpropan-2-ol (29.94 g, 83 mmol) in dichloromethane (300 mL) was covered with aluminum foil. 3-Chloroperoxybenzoic acid (28.65 g of 50%) was added in portions over a period of 50 minutes. The reaction mixture was stirred for an additional 40 minutes, then diluted with 5% aqueous potassium carbonate and stirred. The organic layer was separated, washed with brine (100 mL), dried over magnesium sulfate, filtered, and then concentrated under reduced pressure to provide a yellow paste. This material was combined with ether (100 mL) and stirred overnight. The resulting solid was isolated by filtration to provide 11.84 g of 1-(2-ethoxymethyl-5-oxo-1H-imidazo[4,5-c][1,5]naphthyridin-1-yl)-2-methylpropan-2-ol. The aqueous potassium carbonate layer was partially concentrated, saturated with additional potassium carbonate, and then extracted with dichloromethane. The extract was dried over magnesium sulfate, filtered, and then concentrated under reduced pressure to provide 15.23 g of a dark oil. The oil was combined with ether (100 mL) and stirred overnight. The resulting solid was isolated by filtration to provide 11.51 g of 1-(2-ethoxymethyl-5-oxo-1H-imidazo[4,5-c][1,5]naphthyridin-1-yl)-2-methylpropan-2-ol.

Part E

Concentrated ammonium hydroxide (241 mL) was added to a solution of 1-(2-ethoxymethyl-5-oxo-1H-imidazo[4,5-c][1,5]naphthyridin-1-yl)-2-methylpropan-2-ol (23.35 g, 74 mmol) in dichloromethane (300 mL). A solution of para-toluenesulfonyl chloride (15.52 g, 81 mmol) in dichloromethane (50 mL) was added with rapid stirring over a period of 25 minutes. The reaction mixture was stirred overnight. Concentrated ammonium hydroxide (25 mL) and a solution of para-toluenesulfonyl chloride (2 g) in dichloromethane (10 mL) was added and the reaction mixture was stirred for 5 hours. The organic phase was separated, washed with a solution of potassium carbonate (16 g) in water (300 mL), dried over magnesium sulfate, filtered, and concentrated under reduced pressure to provide 30.17 g of crude product. This material was combined with acetonitrile (300 mL), stirred, heated to reflux, and then allowed to cool with stirring to ambient temperature. The resulting solid was isolated by filtration and then dried at 75° C. under vacuum to provide 14.4 g of a solid. This material was recrystallized from ethyl acetate (17.5 mL/g), isolated by filtration, and then dried under vacuum at 75° C. for 22 hours to provide 12.29 g of 1-(4-amino-2-ethoxymethyl-1H-imidazo[4,5-c][1,5]naphthyridin-1-yl)-2-methylpropan-2-ol as an off white solid, mp 157-159° C. Anal. calcd for $C_{16}H_{21}N_5O_2$: % C, 60.94; % H, 6.71; % N, 22.21. Found: % C, 61.06; % H, 6.67; % N, 22.37.

Part F

A solution of boron tribromide in dichloromethane (11.8 mL of 1 M) was added to a chilled (0° C.) suspension of 1-(4-amino-2-ethoxymethyl-1H-imidazo[4,5-c][1,5]naphthyridin-1-yl)-2-methylpropan-2-ol hydrobromide (1.24 g, 3.93 mmol) in dichloromethane (30 mL). The reaction mixture was allowed to come to ambient temperature with stirring for 16 hours. Methanol (15 mL) and hydrochloric acid (10 mL of 6 N) were added and the reaction mixture was heated at reflux for 2.5 hours. The reaction mixture was made basic with sodium hydroxide and the layers were separated. The aqueous layer was extracted with ethyl acetate (3×100 mL). The combined extracts were washed sequentially with water and brine, dried over magnesium sulfate, and then concentrated under reduced pressure to provide a white solid. This material was crystallized from ethyl acetate and then dried under vacuum at 95° C. for 16 hours to provide 0.55 g of 1-(4-amino-2-hydroxymethyl-1H-imidazo[4,5-c][1,5]naphthyridin-1-yl)-2-methylpropan-2-ol as a white powder, mp 235-237° C. Anal. calcd for $C_{14}H_{17}N_5O_2$: % C, 58.52; % H, 5.96; % N, 24.37. Found: % C, 58.40; % H, 5.82; % N, 24.45.

Example 7

1-[4-Amino-2-(2-hydroxyethyl)-1H-imidazo[4,5-c][1,5]naphthyridin 1-yl]-2-methylpropan-2-ol

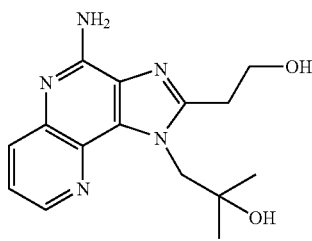 [SMILES: CC(C)(O)Cn1c(CCO)nc2c(N)nc3cccnc3c21]

Part A

A mixture of triethyl orthoformate (10 mL, 60.1 mmol) and 2,2-dimethyl-[1,3]-dioxane-4,6-dione (40.9 g, 0.23 mol) (Meldrum's acid) was heated at 92° C. for 90 minutes and then cooled to 70° C. over one hour. 3-Amino-5-bromopyridine (40.9 g, 0.20 mol) was slowly added over 10 minutes with an ethanol rinse while maintaining the reaction temperature between 60 and 70° C. The reaction was then heated for an additional 20 minutes and allowed to cool to room temperature. The reaction mixture was filtered and washed with ethanol (150 mL) yielding a tan solid. The solid was dried under vacuum for 2 hours to yield 59.14 g of 5-{[(5-bromopyridin-3-yl)imino]methyl}-2,2-dimethyl-1,3-dioxane-4,6-dione as a light yellow crystalline solid, mp 200-202° C.

Part B

5-{[(5-Bromopyridin-3-yl)imino]methyl}-2,2-dimethyl-1,3-dioxane-4,6-dione (59 g, 0.18 mol) was slowly added to DOWTHERM A heat transfer fluid (2000 mL) over a period of 5 minutes at 235-238° C. Following addition, the reaction was maintained for an additional 5 minutes and then allowed to cool to 40° C. A brown precipitate formed, which was filtered and washed with hexanes (150 mL). The brown solid was suspended in an ethanol/water mixture (90:10, 1500 mL), heated to a boil for 30 minutes, isolated by filtration, and washed with ethanol (200 mL) to yield 30.8 g of 7-bromo[1,5]naphthyridin-4-ol as a dark brown powder.

Part C

A mixture of 7-bromo[1,5]naphthyridin-4-ol (33 g, 0.147 mol) and fuming nitric acid (350 mL) was heated at reflux (90° C. internal reaction vessel temperature) for 3 hours. The reaction mixture was cooled to 50° C., poured over 1 L of ice and neutralized to pH 2-3 with a solution of 50% aqueous sodium hydroxide. The resulting precipitate was filtered, washed with water, and dried over vacuum for 3 days to yield 25.1 g of 7-bromo-3-nitro[1,5]naphthyridin-4-ol as a yellow crystalline solid.

Part D

Phosphorous oxychloride (16.76 g, 10.19 mL, 109.3 mmol) was added slowly dropwise to a suspension of 7-bromo-3-nitro[1,5]naphthyridin-4-ol (21.09 g, 78.1 mmol) in N,N-dimethylformamide (250 mL) (DMF) at ambient temperature and maintained overnight. The reaction mixture was then added to ice water (400 mL) with stirring. A solid precipitate formed, which was isolated by vacuum filtration and washed with water. The material was dried under high vacuum at ambient temperature overnight to yield 20.79 g of 7-bromo-4-chloro-3-nitro[1,5]naphthyridine as a tan solid.

Part E

Triethylamine (35.95 mL, 257.9 mmol) was added to a suspension of 7-bromo-4-chloro-3-nitro[1,5]naphthyridine (49.6 g, 172 mmol) in dichloromethane (500 mL). 1-Amino-2-methylpropan-2-ol (16.86 g, 189 mmol) was added dropwise. The reaction mixture was stirred at ambient temperature for 16 hours and then-concentrated under reduced pressure. The residue was triturated with water and stirred for 1 hour. The precipitated solid was isolated by filtration, washed with water, and dried. This material was suspended in diethyl ether (400 mL), sonicated, isolated by filtration, and then dried in a vacuum oven at 40° C. for 16 hours to provide 58.1 g of 1-[(7-bromo-3-nitro[1,5]naphthyridin-4-yl)amino]-2-methylpropan-2-ol as a yellow solid, mp 189-190° C.

Part F

A Parr vessel was charged with 5% Pt/C (5.8 g) and a suspension of 1-[(7-bromo-3-nitro[1,5]naphthyridin-4-yl)amino]-2-methylpropan-2-ol (58.00 g) in acetonitrile (800 mL) and methanol (400 mL). The vessel was placed under hydrogen pressure (30 psi, $2.1 \times 10^5$ Pa) for 8 hours. The reaction mixture was filtered through a layer of CELITE filter aid. The filtrate was concentrated under reduced pressure to provide 52.70 g of 1-[(3-amino-7-bromo[1,5]naphthyridin-4-yl)amino]-2-methylpropan-2-ol as a yellow foam.

Part G

3-Methoxypropionyl chloride (24.90 g, 203 mmol) was added over a period of 5 minutes to a mixture of 1-[(3-amino-7-bromo[1,5]naphthyridin-4-yl)amino]-2-methylpropan-2-ol (52.70 g, 169 mmol), chloroform (100 mL), and acetonitrile (530 mL). The reaction mixture was stirred at ambient temperature overnight. The precipitated solid was isolated by filtration, washed well with acetonitrile, and then dried to provide 60.10 g of N-{7-bromo-4-[(2-hydroxy-2-methylpropyl)amino][1,5]naphthyridin-3-yl}-3-methoxypropionamide hydrochloride as a brown solid, mp 206-208° C.

Part H

A mixture of N-{7-bromo-4-[(2-hydroxy-2-methylpropyl)amino][1,5]naphthyridin-3-yl}-3-methoxypropionamide hydrochloride (60.00 g, 138 mmol), potassium carbonate (60 g), water (300 mL), and ethanol (900 mL) was heated at reflux for 16 hours and then concentrated under reduced pressure. The precipitated solid was isolated by filtration, washed sequentially with water and methanol, and dried to provide a brown solid. This material was dissolved in a 3/1 mixture of chloroform/methanol and decolorized with activated charcoal to provide 38.5 g of 1-[7-bromo-2-(2-methoxyethyl)-1H-imidazo[4,5-c][1,5]naphthyridin-1-yl]-2-methylpropan-2-ol as a white solid, mp 125° C. Anal. calcd for $C_{16}H_{19}BrN_4O_2$: % C, 50.67; % H, 5.05; % N, 14.77. Found: % C, 50.86; % H, 4.94; % N, 15.01.

Part I

3-Chloroperoxybenzoic acid (34.77 g of 75%, 151 mmol) was added to a solution of 1-[7-bromo-2-(2-methoxyethyl)-

1H-imidazo[4,5-c][1,5]naphthyridin-1-yl]-2-methylpropan-2-ol (38.2 g, 101 mmol) in dichloromethane (450 mL) and the reaction mixture was stirred for 3 hours. The reaction mixture was diluted with dichloromethane (200 mL), washed sequentially with 4% aqueous sodium carbonate (2×150 mL) and brine (1×150 mL), and concentrated under reduced pressure to provide the N-oxide derivative. The N-oxide derivative was combined with dichloromethane (450 mL) and concentrated ammonium hydroxide (200 mL) and the mixture was cooled in an ice bath. Para-Toluenesulfonyl chloride (24 g) was added in portions. After the addition was complete the ice bath was removed and the reaction mixture was stirred at ambient temperature for 16 hours. The reaction mixture was diluted with dichloromethane (200 mL). Suspended solids were isolated by filtration, washed with water, and dried to provide 7.60 g of 1-[4-amino-7-bromo-2-(2-methoxyethyl)-1H-imidazo[4,5-c][1,5]naphthyridin-1-yl]-2-methylpropan-2-ol as an off white solid, mp 210-211° C. Anal. calcd for $C_{16}H_{20}BrN_5O_2$: % C, 48.74; % H, 5.11; % N, 17.76. Found: % C, 48.63; % H, 5.10; % N, 17.80.

Part J

A Parr vessel was charged with 10% Pd/C (0.6 g) and a suspension of 1-[4-amino-7-bromo-2-(2-methoxyethyl)-1H-imidazo[4,5-c][1,5]naphthyridin-1-yl]-2-methylpropan-2-ol (4.0 g) in acetonitrile (150 mL) and methanol (50 mL). The vessel was placed under hydrogen pressure (50 psi, $3.4 \times 10^5$ Pa) for 3 hours. The reaction mixture was diluted with 1/1 chloroform/methanol (100 mL), filtered through a layer of CELITE filter aid, and concentrated under reduced pressure. The residue was triturated with acetonitrile to provide 3.55 g of 1-[4-amino-2-(2-methoxyethyl)-1H-imidazo[4,5-c][1,5]naphthyridin-1-yl]-2-methylpropan-2-ol hydrobromide as a white powder, mp 234-235° C. Anal. calcd for $C_{16}H_{22}BrN_5O_2$: % C, 48.49; % H, 5.60; % N, 17.67. Found: % C, 48.64; % H, 5.69; % N, 17.62.

Part K

A solution of boron tribromide in dichloromethane (22.71 mL of 1 M) was added to a chilled (0° C.) suspension of 1-[4-amino-2-(2-methoxyethyl)-1H-imidazo[4,5-c][1,5] naphthyridin-1-yl]-2-methylpropan-2-ol hydrobromide (3.00 g, 7.57 mmol) in dichloromethane (100 mL). The reaction mixture was allowed to come to ambient temperature with stirring for 16 hours. Methanol (30 mL) and hydrochloric acid (30 mL of 6 N) were added and the reaction mixture was heated at reflux for 2.5 hours. The reaction mixture was made basic with sodium hydroxide and the layers were separated. The aqueous layer was extracted with dichloromethane (100 mL). The extract was washed sequentially with water and brine, dried over magnesium sulfate, and then concentrated under reduced pressure to provide a pink solid. This material was crystallized from acetonitrile to provide 0.68 g of 1-[4-amino-2-(2-hydroxyethyl)-1H-imidazo[4,5-c][1,5]naphthyridin-1-yl]-2-methylpropan-2-ol. The aqueous layer was combined with the water and brine washings and allowed to stand overnight. A precipitate was isolated by filtration, washed with water, and dried under vacuum at 95° C. for 3 hours to provide 1.16 g of 1-[4-amino-2-(2-hydroxyethyl)-1H-imidazo[4,5-c][1,5]naphthyridin-1-yl]-2-methylpropan-2-ol as a pink crystalline solid, mp 194-195° C. Anal. calcd for $C_{15}H_{19}N_5O_2$: % C, 59.79; % H, 6.36; % N, 23.24. Found: % C, 59.51; % H, 6.59; % N, 23.34.

Examples 8-13

Preparation of N-[2-(4-amino-2-ethoxymethyl-1H-imidazo[4,5-c][1,5]naphthyridin-1-yl)-1,1-dimethyl-ethyl]-2-methylpropionamide

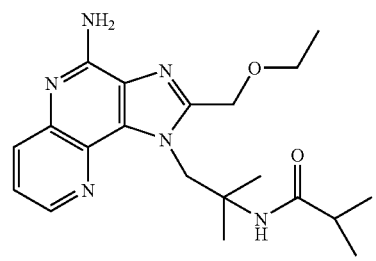 [SMILES: CCOCc1nc2c(N)nc3cccnc3c2n1CC(C)(C)NC(=O)C(C)C]

Triethylamine (556 μL, 4.00 mmol) and isobutyryl chloride (230 μL, 2.20 mmol) were added sequentially to a chilled (0° C.) solution of 1-(2-amino-2-methylpropyl)-2-ethoxymethyl-1H-imidazo[4,5-c][1,5]naphthyridin-4-amine (628 mg, 2.00 mmol) in dichloromethane (20 mL). The reaction mixture was allowed to warm slowly to ambient temperature overnight. The reaction mixture was quenched with aqueous saturated sodium bicarbonate and diluted with dichloromethane (50 mL) The organic layer was separated, washed sequentially with water and brine, dried over sodium sulfate, filtered, and then concentrated under reduced pressure to an amber foam. This material was dissolved in hot propyl acetate (10 mL) and then allowed to cool overnight. Hexanes were added and the now cloudy solution was heated until clear and then allowed stand until crystals formed. The solvent was removed by pipette. The crystals were rinsed with cold propyl acetate/hexanes and then dried under high vacuum at 70° C. to provide 464 mg of N-[2-(4-amino-2-ethoxymethyl-1H-imidazo[4,5-c][1,5]naphthyridin-1-yl)-1,1-dimethylethyl]-2-methylpropionamide as an off white crystalline solid, mp 154.5-155.5° C. Anal. calcd for $C_{20}H_{28}N_6O_2$: % C, 62.48; % H, 7.34; % N, 21.86. Found: % C, 62.14; % H, 7.62; % N, 21.71.

Preparation of 1-[2-(4-amino-2-ethoxymethyl-1H-imidazo[4,5-c][1,5]naphthyridin-1-yl)-1,1-dimethyl-ethyl]-3-(1-methylethyl)urea

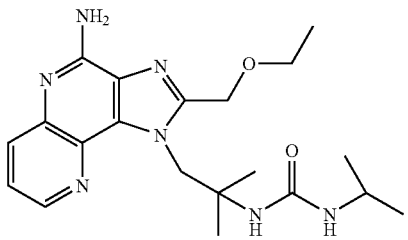 [SMILES: CCOCc1nc2c(N)nc3cccnc3c2n1CC(C)(C)NC(=O)NC(C)C]

Under a nitrogen atmosphere, isopropyl isocyanate (206 μL, 2.10 mmol) was added to a chilled (0° C.) solution of 1-(2-amino-2-methylpropyl)-2-ethoxymethyl-1H-imidazo [4,5-c][1,5]naphthyridin-4-amine (628 mg, 2.00 mmol) in dichloromethane (20 mL). The reaction mixture was allowed to warm slowly to ambient temperature overnight. The resulting precipitate was isolated by filtration and then dried under vacuum at 70° C. to provide 669 mg of 1-[2-(4-amino-2-ethoxymethyl-1H-imidazo[4,5-c][1,5]naphthyridin-1-yl)-1,1-dimethylethyl]-3-(1-methylethyl)urea as white powder, mp 172.5-173.5° C. Anal. calcd for $C_{20}H_{29}N_7O_2$: % C, 60.13; % H, 7.32; % N, 24.54. Found: % C, 59.88; % H, 7.55; % N, 24.51.

A solution of boron tribromide in dichloromethane (about 4 eq of 1 M) was added to a tube containing a chilled (0° C.) solution of a compound of Formula Xa (25 mg, 1 eq) in dichloromethane (1 mL). The tube was vortexed, maintained at 0° C. for 0.5 hour, and then shaken overnight at ambient temperature. The reaction mixture was diluted with methanol (1 mL) and hydrochloric acid (500 μL of 6 N), vortexed, and then the solvents were removed by vacuum centrifugation. The compounds were purified by preparative high performance liquid chromatography (prep HPLC) using a Waters FractionLynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. Table 1 shows the structure of the starting material, the structure of the resulting compound, and the observed accurate mass for the isolated trifluoroacetate salt.

TABLE 1

Starting material Xa (4-amino-2-(ethoxymethyl)-1H-imidazo[4,5-c][1,5]naphthyridine with $R_1$ substituent) → Product Ia (4-amino-2-(hydroxymethyl)-1H-imidazo[4,5-c][1,5]naphthyridine with $R_1$ substituent)

| Example | $R_1$ | Measured Mass (M + H) |
|---|---|---|
| 8 | –CH$_2$–C(CH$_3$)$_2$–OH (2-hydroxy-2-methylpropyl) | 288.1440 |
| 9 | –CH$_2$–C(CH$_3$)$_2$–NH–S(O)$_2$–CH$_3$ (2-methyl-2-(methanesulfonylamino)propyl) | 365.1378 |
| 10 | –CH$_2$–C(CH$_3$)(CH$_2$CH$_3$)–NH–C(O)–cyclohexyl | 397.2348 |
| 11 | –CH$_2$–C(CH$_3$)$_2$–NH$_2$ with ethyl (2-amino-2-methylbutyl) | 287.1607 |
| 12 | –CH$_2$–C(CH$_3$)(CH$_2$CH$_3$)–NH–C(O)–CH(CH$_3$)$_2$ | 357.2055 |
| 13 | –CH$_2$–C(CH$_3$)(CH$_2$CH$_3$)–NH–C(O)–NH–CH(CH$_3$)$_2$ | 372.2157 |

Example 14

[4-Amino-1-(2-fluoro-2-methylpropyl)-1H-imidazo[4,5-c][1,5]naphthyridin-2-yl]methanol

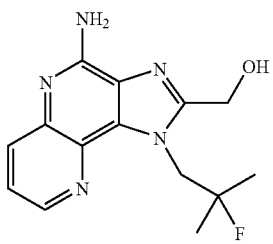 [SMILES: CC(C)(F)Cn1c(CO)nc2c(N)nc3cccnc3c21]

Part A

A solution of 1-amino-2-methylpropan-2-ol (23.4 g, 263 mmol) dissolved in 150 mL of THF was treated with 150 mL of 1.8 M aqueous NaOH solution and the mixture was placed in an ice bath. A solution of di-tert-butyl dicarbonate (57.3 g, 263 mmol) in 150 mL THF was then added drop-wise over 45 min. The mixture was allowed to warm to ambient temperature overnight. The THF was removed under reduced pressure and the remaining aqueous solution was treated with 1 M $H_2SO_4$ until the pH reached 3. The mixture was extracted with 200 mL of EtOAc. The organic portion was washed with $H_2O$ and brine, dried over $Na_2SO_4$, and concentrated under reduced pressure give tert-butyl 2-hydroxy-2-methylpropylcarbamate (50.4 g) as a colorless syrup which solidified on standing.

Part B

A stirred solution of tert-butyl 2-hydroxy-2-methylpropylcarbamate (7.81 g, 41.3 mmol) dissolved in 300 mL of anhydrous $CH_2Cl_2$ was cooled to −78° C. under an atmosphere of $N_2$. The reaction mixture was treated with diethylaminosulfur trifluoride (DAST) (6.2 mL, 47 mmol) and allowed to warm to ambient temperature overnight. The reaction mixture was treated with saturated $NaHCO_3$ solution and the layers were separated. The organic portion was washed successively with saturated $NaHCO_3$ solution, $H_2O$ and brine. The organic portion was dried over $Na_2SO_4$, filtered and concentrated under reduced pressure. Chromatography ($SiO_2$, 10% EtOAc/hexanes) gave 6.27 g of tert-butyl 2-fluoro-2-methylpropylcarbamate as an amber oil which solidified on standing.

Part C tert-Butyl 2-fluoro-2-methylpropylcarbamate (6.27 g, 32.8 mmol) was treated with 45 mL of 3.0 M HCl in ethanol and the mixture was heated to 90° C. for 2 hours. The reaction mixture was then concentrated under reduced pressure to give 4.02 g of 2-fluoro-2-methylpropan-1-amine hydrochloride as a white solid.

Part D

2-Fluoro-2-methylpropan-1-amine hydrochloride (4.02 g, 31.4 mmol) was dissolved in 80 mL of dry $CH_2Cl_2$. Triethylamine (13.1 mL, 94.2 mmol) and 4-chloro-3-nitro[1,5]naphthyridine (6.56 g, 31.4 mmol) were then added and the reaction was stirred under $N_2$ for 2 days. The reaction mixture was then concentrated under reduced pressure to give a dark-yellow solid. The solid was treated with 200 mL of $H_2O$ and the mixture was heated to reflux with rapid stirring. The mixture was cooled and the yellow solid was isolated by filtration. The material was washed with $H_2O$ and the dried under vacuum to give N-(2-fluoro-2-methylpropyl)-3-nitro[1,5]naphthyridin-4-amine (8.36 g) as a yellow powder.

Part E

A solution of N-(2-fluoro-2-methylpropyl)-3-nitro[1,5]naphthyridin-4-amine (2.64 g, 10.0 mmol) dissolved in 80 mL of acetonitrile was placed in a pressure bottle. Platinum on carbon (5%, 500 mg) was then added and the reaction mixture was shaken under $H_2$ at 50 PSI ($3.4 \times 10^5$ Pa). After 5 hours, the reaction mixture was filtered through a pad of CELITE filter agent. The pad was rinsed with acetonitrile and the combined filtrates were concentrated under reduced pressure to give 2.12 g of N-(2-fluoro-2-methylpropyl)[1,5]naphthyridine-3,4-diamine as a brown foam.

Part F $N^4$-(2-Fluoro-2-methylpropyl)[1,5]naphthyridine-3,4-diamine (2.12 g, 9.06 mmol) was dissolved in 90 mL of anhydrous $CH_2Cl_2$ and the stirred solution was cooled to, 0° C. under $N_2$. Triethylamine (1.39 mL, 10.0 mmol) and acetoxyacetyl chloride (1.07 mL, 10.0 mmol) were then added and the reaction mixture was stirred overnight. The reaction mixture was concentrated under reduced pressure and the resulting material was dissolved in 90 mL of ethanol and treated with 5 mL of triethylamine. The mixture was heated at reflux for 4 days. The reaction mixture was then cooled and concentrated under reduced pressure to give a purple solid. The purple solid was partitioned between $CH_2Cl_2$ (75 mL) and $H_2O$ (75 mL). The layers were separated and the aqueous portion was extracted with $CH_2Cl_2$ (2×20 mL). The combined organic portions were washed with brine, dried over $Na_2SO_4$, filtered and concentrated under reduced pressure to give a purple solid. The resulting material was dissolved in 50 mL of methanol and treated with 1 mL of saturated aqueous $K_2CO_3$ solution. After 1 hour, the mixture was treated with 3.5% $NaH_2PO_4$ solution and the methanol was removed by evaporation under reduced pressure. A brown solid precipitated out of the aqueous solution and was isolated by filtration. The brown solid was rinsed with $H_2O$ and then dried to give 1.81 g of [1-(2-fluoro-2-methylpropyl)-1H-imidazo[4,5-c][1,5]naphthyridin-2-yl]methanol.

Part G

A solution of [1-(2-fluoro-2-methylpropyl)-1H-imidazo[4,5-c][1,5]naphthyridin-2-yl]methanol (1.53 g, 5.58 mmol) dissolved in 50 mL of $CH_2Cl_2$ was treated with triethylamine (1.55 mL, 11.2 mmol), acetic anhydride (663 µL; 6.70 mmol), and 10 mg of 4-(dimethylamino)pyridine (DMAP). After stirring for 2 hours, the reaction mixture was treated with saturated $NaHCO_3$ solution and the layers were separated. The organic portion was washed successively with 3.5% $NaH_2PO_4$ solution, $H_2O$ and brine. The organic portion was dried over $Na_2SO_4$, filtered and concentrated under reduced pressure. Chromatography ($SiO_2$, 40-60% acetone/hexanes) gave 1.59 g of [1-(2-fluoro-2-methylpropyl)-1H-imidazo[4,5-c][1,5]naphthyridin-2-yl]methyl acetate as an off-white powder.

Part H

[1-(2-Fluoro-2-methylpropyl)-1H-imidazo[4,5-c][1,5]naphthyridin-2-yl]methyl acetate (1.59 g, 5.03 mmol) was dissolved in 50 mL of $CH_2Cl_2$ and treated with 3-chloroperoxybenzoic acid (1.52 g, 57-86% purity). After stirring for 2 hours, the reaction mixture was treated with 25 mL of $CH_2Cl_2$ and 20 mL of 5% $Na_2CO_3$ solution and the layers were separated. The organic layer was washed with $H_2O$ (20 mL) and brine (20 mL), dried over $Na_2SO_4$, filtered, and concentrated under reduced pressure to give 1.67 g of [1-(2-fluoro-2-methylpropyl)-5-oxido-1H-imidazo[4,5-c][1,5]naphthyridin-2-yl]methyl acetate as an off-white solid.

Part I

[1-(2-Fluoro-2-methylpropyl)-5-oxido-1H-imidazo[4,5-c][1,5]naphthyridin-2-yl]methyl acetate (1.67 g, 5.03 mmol)

was dissolved in 50 mL of $CH_2Cl_2$ and treated with 5 mL of concentrated aqueous $NH_4OH$ solution. The mixture was stirred rapidly and then p-toluenesulfonyl chloride (1.05 g, 5.53 mmol) was carefully added. Rapid stirring was continued for 1 hour. The reaction mixture was then treated with 20 mL of $H_2O$. The layers were separated and the organic portion was washed successively with 5% $Na_2CO_3$ solution, $H_2O$ and brine. The organic portion was dried over $Na_2SO_4$, filtered, and; concentrated under reduced pressure. Chromatography ($SiO_2$, 2.5% methanol/$CHCl_3$) gave 1.13 g of [4-amino-1-(2-fluoro-2-methylpropyl)-1H-imidazo[4,5-c][1,5]naphthyridin-2-yl]methyl acetate as a light-yellow solid.

Part J

A solution of [4-amino-1-(2-fluoro-2-methylpropyl)-1H-imidazo[4,5-c][1,5]naphthyridin-2-yl]methyl acetate (1.13 g, 3.41 mmol) dissolved in 10 mL of methanol was treated with 10 mL of a 7% solution of ammonia in methanol. The mixture was stirred for 2 hours and then concentrated under reduced pressure. The resulting solid was treated with $H_2O$ and the mixture was heated to reflux for 15 minutes. The mixture was cooled and the resulting light-yellow solid was isolated by filtration. The light-yellow, solid was then treated with 20 mL of $CH_2Cl_2$ and the mixture was stirred rapidly for several minutes. The mixture was filtered and the resulting white solid was washed with several portions of cold $CH_2Cl_2$ and dried with suction. Crystallization from ethanol/$H_2O$ gave 477 mg of [4-amino-1-(2-fluoro-2-methylpropyl)-1H-imidazo[4,5-c][1,5]naphthyridin-2-yl]methanol as fluffy cream colored crystals, mp 240-241° C. $^1$H NMR (300 MHz, DMSO-$d_6$) δ 8.50 (dd, J=1.5, 4.3 Hz, 1H), 7.93 (dd, J=1.5, 8.4 Hz, 1H), 7.46 (dd, J=4.3, 8.4 Hz, 1H), 6.92 (s, 2H), 5.62 (t, J=5.8 Hz, 1H), 5.33 (br s, 2H), 4.83 (d, J=4.7 Hz, 2H), 1.33 (d, J=20.3 Hz, 6H); $^{13}$C NMR (125 MHz, DMSO-$d_6$) δ 154.3, 152.7, 143.1, 140.8, 134.2, 133.4, 133.2, 128.7, 122.5, 96.8 (d, J=170 Hz), 56.7 (d, J=9.5 Hz), 52.7 (d, J=21.4 Hz), 24.5; MS (ESI) m/z 290 (+H)$^+$; Anal. calcd for $C_{14}H_{16}FN_5O$: C, 58.12; H, 5.57; N, 24.21. Found: C, 58.19; H, 5.54; N, 24.16.

Example 15

2-[4-Amino-1-(2-fluoro-2-methylpropyl)-1H-imidazo[4,5-c][1,5]naphthyridin-2-yl]ethanol

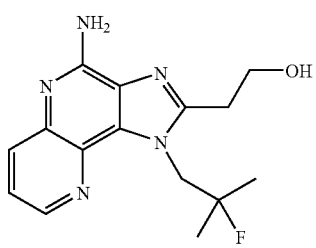 [SMILES: CC(C)(F)Cn1c(CCO)nc2c(N)nc3cccnc3c21]

Part A $N^4$-(2-Fluoro-2-methylpropyl)[1,5]naphthyridine-3,4-diamine (2.34 g, 10.0 mmol) was dissolved in 80 mL of anhydrous $CH_2Cl_2$ and the stirred solution was cooled to 0° C. under $N_2$. Triethylamine (2.78 mL, 10.0 mmol) and 3-(benzyloxy)propanoyl chloride, prepared by the method of Li, *J. Med. Chem.*, 42, pp. 706-721, (2.13 g, 10.0 mmol), were then added and the reaction mixture was stirred overnight. The reaction mixture was concentrated under reduced pressure. The resulting material was dissolved in 80 mL of ethanol and combined with 5 mL of triethylamine and the mixture was heated to reflux for 4 days. The reaction mixture was then cooled and concentrated under reduced pressure. The resulting solid was partitioned between $CH_2Cl_2$ (75 mL) and $H_2O$ (75 mL). The layers were separated and the organic portion was washed with brine, dried over $Na_2SO_4$, filtered, and concentrated under reduced pressure to give a solid. Chromatography ($SiO_2$, 1-2% CMA/$CHCl_3$) gave 0.83 g of uncyclized amide (3-(benzyloxy)-N-{4-[(2-fluoro-2-methylpropyl)amino][1,5]naphthyridin-3-yl}propanamide) and the desired 2-[2-(benzyloxy)ethyl]-1-(2-fluoro-2-methylpropyl)-1H-imidazo[4,5-c][1,5]naphthyridine. Additional chromatography (10% methanol/$CHCl_3$) of the desired material gave 1.39 g of a light-orange syrup. The isolated amide was converted to the desired imidazole by dissolving the material in 10 mL of 7% ammonia in methanol. The mixture was placed in a stainless-steel pressure vessel and the vessel was sealed and heated to 150° C. overnight. The reaction mixture was cooled and concentrated under reduced pressure. Chromatography ($SiO_2$, 2% CMA/$CHCl_3$) gave 0.50 g of the desired product which was combined with the first batch of material for the next reaction.

Part B

2-[2-(Benzyloxy)ethyl]-1-(2-fluoro-2-methylpropyl)-1H-imidazo[4,5-c][1,5]naphthyridine (1.89 g, 5.0 mmol) was dissolved in 50 mL of $CH_2Cl_2$ and treated with 3-chloroperoxybenzoic acid (1.50 g, 57-86% purity). After stirring for 2 hours, the reaction mixture was treated with 50 mL of 2% $Na_2CO_3$ solution and the layers were separated. The aqueous portion was extracted with an additional 25 mL of $CH_2Cl_2$. The combined organic layers were washed successively with 2% $Na_2CO_3$, $H_2O$ and brine, dried over $Na_2SO_4$, filtered, and concentrated under reduced pressure to give 1.97 g of 2-[2-(benzyloxy)ethyl]-1-(2-fluoro-2-methylpropyl)-1H-imidazo[4,5-c][1,5]naphthyridine 5-oxide as an off-white solid.

Part C

2-[2-(Benzyloxy)ethyl]-1-(2-fluoro-2-methylpropyl)-1H-imidazo[4,5-c][1,5]naphthyridine 5-oxide (1.97 g, 5.00 mmol) was dissolved in 50 mL of $CH_2Cl_2$ and treated with 5 mL of concentrated aqueous $NH_4OH$ solution. The mixture was stirred rapidly and then p-toluenesulfonyl chloride (1.00 g, 5.33 mmol) was carefully added. Rapid stirring was continued for 1 hour. The reaction mixture was then treated with 20 mL of $H_2O$. The layers were separated and the organic portion was washed successively with 5% $Na_2CO_3$ solution, $H_2O$ and brine. The organic portion was dried over $Na_2SO_4$, filtered, and concentrated under reduced pressure. Chromatography ($SiO_2$, 10% CMA/$CHCl_3$) gave 0.90 g of 2-[2-(benzyloxy)ethyl]-1-(2-fluoro-2-methylpropyl)-1H-imidazo[4,5-c][1,5]naphthyridin-4-amine as a yellow solid.

Part D

A solution of 2-[2-(benzyloxy)ethyl]-1-(2-fluoro-2-methylpropyl)-1H-imidazo[4,5-c][1,5]naphthyridin-4-amine (0.78 g, 1.98 mmol) dissolved in 20 mL of methanol was treated with 10% palladium on carbon (200 mg) and 0.68 mL of 3 M HCl in ethanol. The mixture was shaken under $H_2$ at 50 PSI (3.4×10$^5$ Pa) overnight. Additional 10% palladium on carbon (200 mg) and 3 M HCl in ethanol (0.33 mL) were added and shaking was continued for 24 hours. The reaction mixture was filtered through a pad of CELITE filter agent. The pad was rinsed with methanol and the combined filtrates were concentrated under reduced pressure. The resulting material was treated with 20 mL of H₂O and 2 mL of concentrated NH₄OH solution and extracted into CHCl₃ (3×25 mL). The combined organic layers were concentrated under reduced pressure. Chromatography (SiO₂, 15-30% CMA/ CHCl₃) gave a white powder. Crystallization from ethanol/ H₂O gave 276 mg of 2-[4-amino-1-(2-fluoro-2-methylpropyl)-1H-imidazo[4,5-c][1,5]naphthyridin-2-yl]ethanol as white needles, mp 224-225° C.

$^1$H NMR (300 MHz, DMSO-$d_6$, 354K) δ 8.470 (dd, J=1.3, 4.0 Hz, 1H), 7.91 (d, J=8.4 Hz, 1H), 7.40 (dd, J=4.1, 8.3 Hz, 1H), 6.46 (s, 2H), 5.25 (d, J=22.7 Hz, 2H), 4.57 (s, 1H), 3.91 (d, J=5.4 Hz, 2H), 3.14 (t, J=6.4 Hz, 2H), 1.33 (d, J=21.7 Hz, 6H); $^{13}$C NMR (125 MHz, DMSO-$d_6$) δ 154.0, 152.3, 143.0, 140.4, 134.1, 133.1, 132.6, 129.0, 122.2, 96.7 (d, J=170 Hz), 60.2, 52.5 (d, J=20.9 Hz), 30.6 (d, J=6.6 Hz), 24.4; MS (ESI) m/z 304 (M+H)$^+$; Anal. calcd for $C_{15}H_{18}FN_5O$: C, 59.39; H, 5.98; N, 23.09. Found: C, 59.57; H, 5.75; N, 23.07.

Examples 16-56

Part A

A solution of 1-(2-aminoethyl)-2-(2-methoxyethyl)-1H-imidazo[4,5-c][1,5]naphthyridin-4-amine (57 mg, 0.1 mmol, 1 eq, prepared according to the general method of Example 4 using methoxypropionyl chloride in lieu of methoxyacetyl chloride) and N,N-diisopropylethylamine (87 μL) in N,N-dimethylacetamide (1 mL) was added to a tube containing a reagent (1.1 eq) from the table below. The reaction mixture was vortexed overnight, the reaction was quenched with water (2 drops), and the solvent was removed by vacuum centrifugation. The reaction mixture was purified by solid-supported liquid-liquid extraction according to the following procedure. The sample was dissolved in chloroform (1 mL) then loaded onto diatomaceous earth that had been equilibrated with 2 M sodium carbonate solution (600 μL) for about 20 minutes. After 10 minutes chloroform (500 μL) was added to elute the product from the diatomaceous earth into a well of a collection plate. After an additional 10 minutes the process was repeated with additional chloroform (500 μL). The solvent was then removed by vacuum centrifugation.

Part B

The material from Part A was dissolved in dichloromethane (1 mL) and the solution was cooled to 0° C. Boron tribromide (400 μL of 1 M in dichloromethane) was added and the reaction mixture was vortexed overnight. Methanol (1 mL) and 6 N hydrochloric acid (500 μL) were added and the reaction mixture was vortexed for 15 minutes. The solvent was removed by vacuum. The compounds were purified as described for Examples 8-13. The table below shows the reagent used for each example, the structure of the resulting compound, and the observed accurate mass for the isolated trifluoroacetate salt.

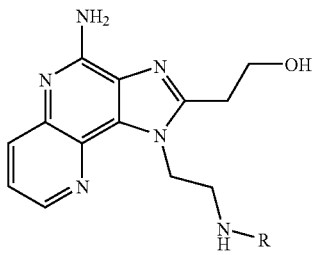

| Example | Reagent | R | Measured Mass (M + H) |
|---|---|---|---|
| 16 | None |  | 273.1479 |
| 17 | Cyclopropanecarbonyl chloride | 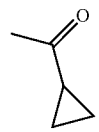 | 341.1730 |
| 18 | Isobutyryl chloride | 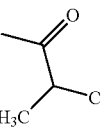 | 343.1909 |
| 19 | Cyclobutanecarbonyl chloride | 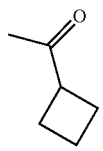 | 355.1909 |
| 20 | Cyclopentanecarbonyl chloride | 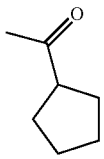 | 369.2062 |
| 21 | Benzoyl chloride | 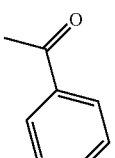 | 377.1747 |
| 22 | Cyclohexanecarbonyl chloride | 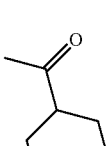 | 383.2206 |
| 23 | 3-Cyanobenzoyl chloride | 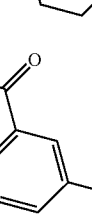 | 402.1702 |

53
-continued

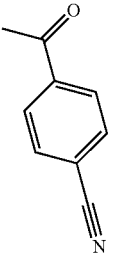

| Example | Reagent | R | Measured Mass (M + H) |
|---|---|---|---|
| 24 | 4-Cyanobenzoyl chloride | 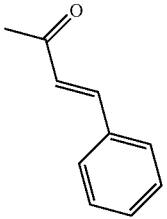 | 402.1700 |
| 25 | Cinnamoyl chloride | 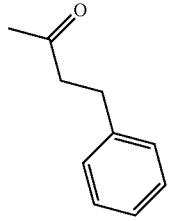 | 403.1890 |
| 26 | Hydrocinnamoyl chloride | 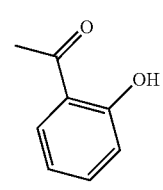 | 405.2044 |
| 27 | 2-Methoxybenzoyl chloride | 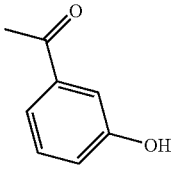 | 393.1672 |
| 28 | 3-Methoxybenzoyl chloride | 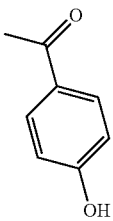 | 393.1689 |

54
-continued

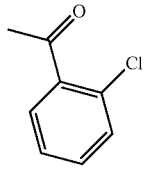

| Example | Reagent | R | Measured Mass (M + H) |
|---|---|---|---|
| 29 | p-Anisoyl chloride | 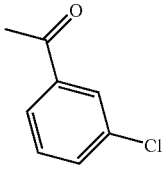 | 393.1678 |
| 30 | 2-Chlorobenzoyl chloride | 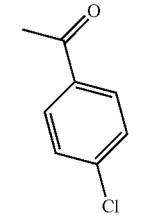 | 411.1306 |
| 31 | 3-Chlorobenzoyl chloride | 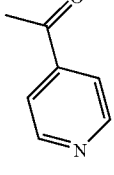 | 411.1369 |
| 32 | 4-Chlorobenzoyl chloride | | 411.1368 |
| 33 | Isonicotinoyl chloride hydrochloride | | 378.1698 |
| 34 | Nicotinoyl chloride hydrochloride | | 378.1676 |
| 35 | Methanesulfonyl chloride | 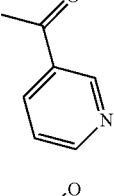 | 351.1256 |

-continued

[Structure: imidazo-naphthyridine core with NH2, CH2CH2OH, and N-CH2CH2-NHR substituent]

| Example | Reagent | R | Measured Mass (M + H) |
|---------|---------|---|---------|
| 36 | Ethanesulfonyl chloride | -SO2-CH2CH3 | 365.1386 |
| 37 | 1-Propanesulfonyl chloride | -SO2-CH2CH2CH3 | 379.1534 |
| 38 | Dimethylsulfamoyl chloride | -SO2-N(CH3)2 | 380.1512 |
| 39 | Benzenesulfonyl chloride | -SO2-phenyl | 413.1436 |
| 40 | 1-Methylimidazole-4-sulfonyl chloride | -SO2-(1-methylimidazol-4-yl) | 417.1462 |
| 41 | 2,2,2-Trifluoroethanesulfonyl chloride | -SO2-CH2CF3 | 419.1139 |
| 42 | alpha-Toluenesulfonyl chloride | -SO2-CH2-phenyl | 427.1569 |

-continued

[Structure: imidazo-naphthyridine core with NH2, CH2CH2OH, and N-CH2CH2-NHR substituent]

| Example | Reagent | R | Measured Mass (M + H) |
|---------|---------|---|---------|
| 43 | 3-Cyano-benzenesulfonyl chloride | -SO2-(3-cyanophenyl) | 438.1380 |
| 44 | 3-Methoxy-benzenesulfonyl chloride | -SO2-(3-hydroxyphenyl) | 429.1349 |
| 45 | 2-Chloro-benzenesulfonyl chloride | -SO2-(2-chlorophenyl) | 447.0996 |
| 46 | 4-Chloro-benzenesulfonyl chloride | -SO2-(4-chlorophenyl) | 447.1031 |
| 47 | Isopropyl isocyanate | -C(O)NH-CH(CH3)2 | 358.1994 |
| 48 | Phenyl isocyanate | -C(O)NH-phenyl | 392.1794 |

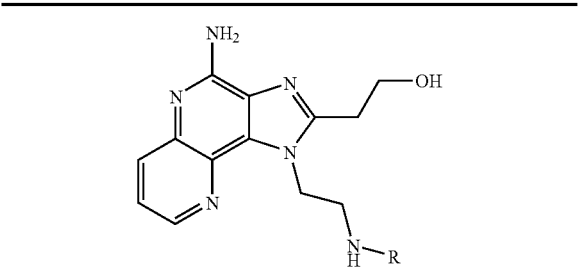

| Example | Reagent | R | Measured Mass (M + H) |
|---|---|---|---|
| 49 | Cyclohexyl isocyanate | 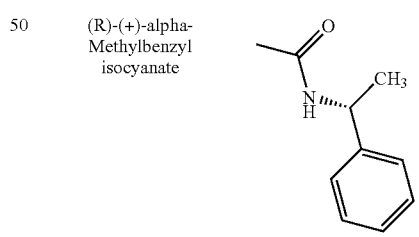 | 398.2305 |
| 50 | (R)-(+)-alpha-Methylbenzyl isocyanate | 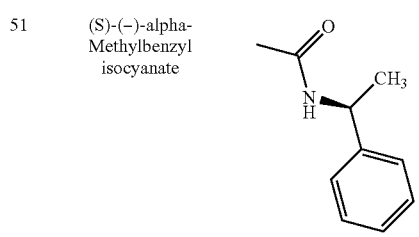 | 420.2178 |
| 51 | (S)-(−)-alpha-Methylbenzyl isocyanate | 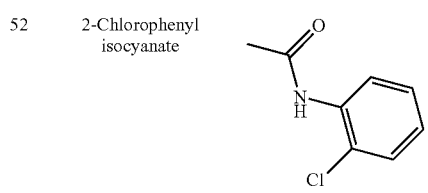 | 420.2149 |
| 52 | 2-Chlorophenyl isocyanate | 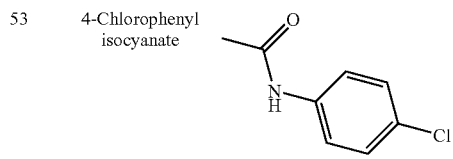 | 426.1453 |
| 53 | 4-Chlorophenyl isocyanate | 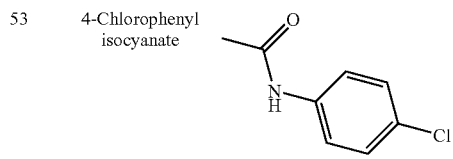 | 426.1460 |
| 54 | N,N-Dimethyl-carbamoyl chloride | 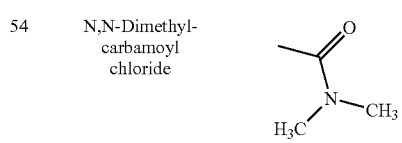 | 344.1856 |

| Example | Reagent | R | Measured Mass (M + H) |
|---|---|---|---|
| 55 | 1-Piperidine-carbonyl chloride | | 384.2137 |
| 56 | 4-Morpholinyl-carbonyl chloride | | 386.1976 |

Examples 57-95

The compounds in the table below were prepared and purified according to the methods described in Examples 16-56 using 1-(2-aminoethyl)-2-methoxymethyl-1H-imidazo[4,5-c][1,5]naphthyridin-4-amine in lieu of 1-(2-aminoethyl)-2-(2-methoxyethyl)-1H-imidazo[4,5-c][1,5]naphthyridin-4-amine. The table below shows the reagent used for each example, the structure of the resulting compound, and the observed accurate mass for the isolated trifluoroacetate salt.

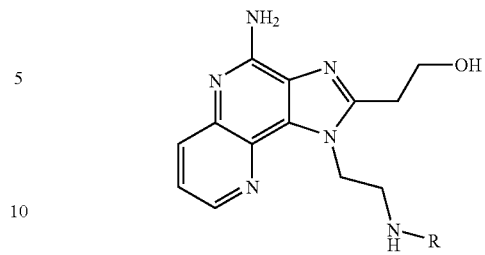

| Example | Reagent | R | Measured Mass (M + H) |
|---|---|---|---|
| 57 | Cyclopropanecarbonyl chloride | | 327.1581 |

-continued

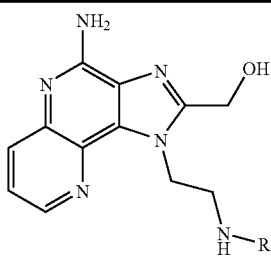

| Example | Reagent | R | Measured Mass (M + H) |
|---|---|---|---|
| 58 | Isobutyryl chloride | (isopropyl ketone) | 329.1709 |
| 59 | Cyclopentanecarbonyl chloride | (cyclopentyl ketone) | 355.1859 |
| 60 | Benzoyl chloride | (phenyl ketone) | 363.1563 |
| 61 | Cyclohexanecarbonyl chloride | (cyclohexyl ketone) | 369.2019 |
| 62 | 3-Cyanobenzoyl chloride | (3-cyanophenyl ketone) | 388.1517 |
| 63 | Hydrocinnamoyl chloride | (phenethyl ketone) | 391.1868 |
| 64 | 3-Methoxybenzoyl chloride | (3-hydroxyphenyl ketone) | 379.1512 |

-continued

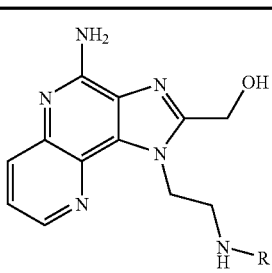

| Example | Reagent | R | Measured Mass (M + H) |
|---|---|---|---|
| 65 | p-Anisoyl chloride | (4-hydroxyphenyl ketone) | 379.1526 |
| 66 | 2-Chlorobenzoyl chloride | (2-chlorophenyl ketone) | 397.1193 |
| 67 | 3-Chlorobenzoyl chloride | (3-chlorophenyl ketone) | 397.1198 |
| 68 | Isonicotinoyl chloride hydrochloride | (4-pyridyl ketone) | 364.1515 |
| 69 | Nicotinoyl chloride hydrochloride | (3-pyridyl ketone) | 364.1535 |
| 70 | Picolinoyl chloride hydrochloride | (2-pyridyl ketone) | 364.1512 |

-continued

| Example | Reagent | R | Measured Mass (M + H) |
|---|---|---|---|
| 71 | trans-2-Phenyl-1-cyclo-propanecarbonyl chloride | 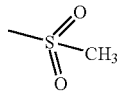 | 403.1852 |
| 72 | Methanesulfonyl chloride | 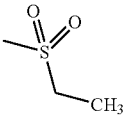 | 337.1070 |
| 73 | Ethanesulfonyl chloride | 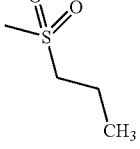 | 351.1212 |
| 74 | 1-Propanesulfonyl chloride | 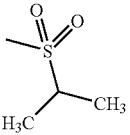 | 365.1386 |
| 75 | Isopropylsulfonyl chloride | 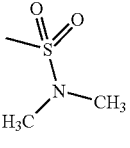 | 365.1433 |
| 76 | Dimethyl-sulfamoyl chloride | 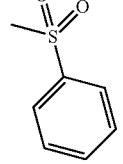 | 366.1355 |
| 77 | Benzenesulfonyl chloride | 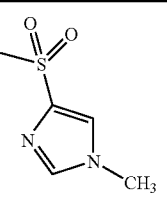 | 399.1214 |

-continued

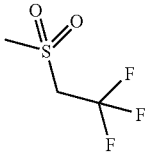

| Example | Reagent | R | Measured Mass (M + H) |
|---|---|---|---|
| 78 | 1-Methyl-imidazole-4-sulfonyl chloride | 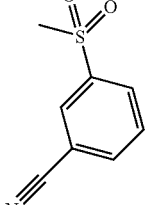 | 403.1311 |
| 79 | 2,2,2-Trifluoro-ethanesulfonyl chloride | 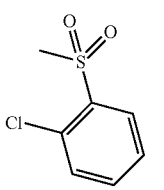 | 405.0953 |
| 80 | 3-Cyano-benzenesulfonyl chloride | 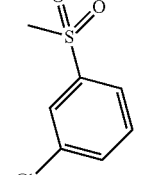 | 424.1229 |
| 81 | 2-Chloro-benzenesulfonyl chloride | 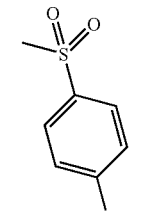 | 433.0872 |
| 82 | 3-Chloro-benzenesulfonyl chloride | | 433.0867 |
| 83 | 4-Chloro-benzenesulfonyl chloride | | 433.0853 |

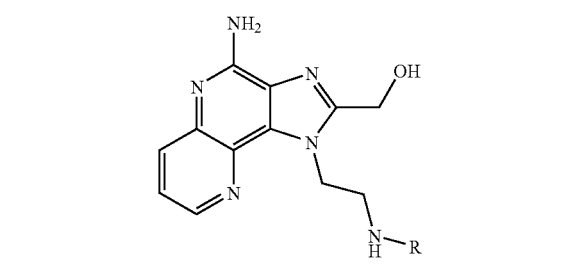

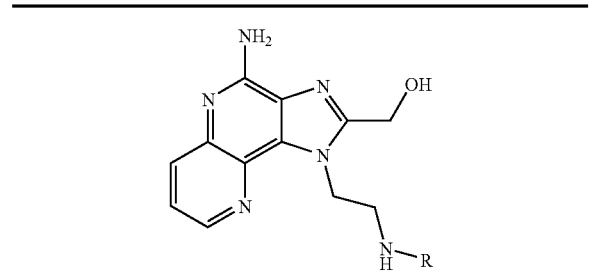

| Example | Reagent | R | Measured Mass (M + H) |
|---|---|---|---|
| 84 | Methyl isocyanate | -C(O)NHCH₃ | 316.1528 |
| 85 | Ethyl isocyanate | -C(O)NHCH₂CH₃ | 330.1660 |
| 86 | Isopropyl isocyanate | -C(O)NHCH(CH₃)₂ | 344.1819 |
| 87 | n-Propyl isocyanate | -C(O)NHCH₂CH₂CH₃ | 344.1809 |
| 88 | Cyclopentyl isocyanate | -C(O)NH-cyclopentyl | 370.1994 |
| 89 | Cyclohexyl isocyanate | -C(O)NH-cyclohexyl | 384.2152 |
| 90 | 3-Chlorophenyl isocyanate | -C(O)NH-(3-Cl-C₆H₄) | 412.1300 |
| 91 | 4-Chlorophenyl isocyanate | -C(O)NH-(4-Cl-C₆H₄) | 412.1273 |
| 92 | N,N-Dimethyl-carbamoyl chloride | -C(O)N(CH₃)₂ | 330.1686 |
| 93 | 1-Piperidine-carbonyl chloride | -C(O)-piperidinyl | 370.1979 |
| 94 | 4-Morpholinyl-carbonyl chloride | -C(O)-morpholinyl | 372.1811 |
| 95 | 4-Methyl-1-piperazine-carbonyl chloride | -C(O)-(4-methylpiperazinyl) | 385.2098 |

Example 96

[4-Amino-1-(2-methylpropyl)-1H-imidazo[4,5-c][1,5]naphthyridin-2-yl]methanol

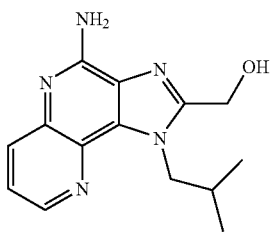 [SMILES: CC(C)Cn1c(CO)nc2c(N)nc3cccnc3c21]

To a chilled solution (ice bath) of 2-(ethoxymethyl)-1-(2-methylpropyl)-1H-imidazo[4,5-c][1,5]naphthyridin-4-amine (2.0 g, 6.69 mmol, prepared according to the general methods of Example 6 using 2-methylpropan-1-amine in lieu of 1-amino-2-methylpropan-2-ol) in dichloromethane (50 mL) was added boron tribromide (20 mL, 1M solution in dichloromethane). The mixture turned light purple and was stirred at ambient temperature for 44 hours. The reaction was quenched with methanol (20 mL) and aqueous hydrochloric acid (6N, 10 mL). After stirring for 4 hours, the pH was adjusted to 10 by the addition of aqueous sodium hydroxide (50%). Dichloromethane (50 mL) was added with stirring and the layers were separated. The aqueous fraction was extracted with chloroform (2×250 mL). The combined organic fractions were concentrated to provide 1.4 g of [4-amino-1-(2-methylpropyl)-1H-imidazo[4,5-c][1,5]naphthyridin-2-yl]methanol as a white powder, mp 226-228° C.

$^1$H NMR (300 MHz, DMSO-$d_6$) δ 8.52-8.51 (dd, J=1.6, 4.3 Hz, 1H), 7.93-7.89 (dd, J=1.6, 8.4 Hz, 1H), 7.46-7.42 (dd, J=4.3, 8.4 Hz, 1H), 6.83 (s, 2H), 5.69-5.65 (t, J=5.8 Hz, 1H), 4.79-4.77 (d, J=5.8 Hz, 2H), 4.74-4.71 (d, J=7.6 Hz, 2H), 2.44-2.39 (m, 1H), 0.91-0.88 (d, J=6.7 Hz, 6H);

Anal. calcd for $C_{14}H_{17}N_5O$: C, 61.98; H, 6.31; N, 25.81. Found: C, 61.26; H, 6.07; N, 25.75.

Exemplary Compounds

Certain exemplary compounds, including some of those described above in the Examples, have the following Formula Ib and the following substituents n and $R_1$ wherein each line of the table is matched to Formula Ib to represent a specific embodiment of the invention.

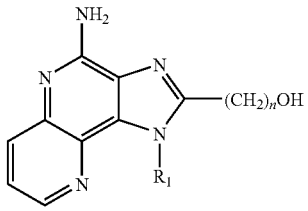

Ib

| n | $R_1$ |
|---|---|
| 1 | 2-[(cyclohexylcarbonyl)amino]-2-methylpropyl |
| 1 | 2-[(cyclopropylcarbonyl)amino]ethyl |
| 1 | 4-[(cyclopropylcarbonyl)amino]butyl |
| 1 | 2,3-dihydroxypropyl |
| 1 | 2,2-dimethyl-3-(methylsulfonyl)propyl |
| 1 | 2-fluoro-2-methylpropyl |
| 1 | 2-hydroxy-2-methylpropyl |
| 1 | 2-methylpropyl |
| 1 | 2-methyl-2-({[(1-methylethyl)amino]carbonyl}amino)propyl |
| 1 | 2-{[(1-methylethyl)carbonyl]amino}ethyl |
| 1 | 4-{[(1-methylethyl)carbonyl]amino}butyl |
| 1 | 2-methyl-2-[(methylsulfonyl)amino]propyl |
| 1 | 4-[(methylsulfonyl)amino]butyl |
| 1 | 2-[(methylsulfonyl)amino]ethyl |
| 1 | 4-[(4-morpholinecarbonyl)amino]butyl |
| 1 | 2-[(4-morpholinecarbonyl)amino]ethyl |
| 1 | tetrahydro-2H-pyran-4-ylmethyl |
| 2 | 2-[(cyclohexylcarbonyl)amino]-2-methylpropyl |
| 2 | 2-[(cyclopropylcarbonyl)amino]ethyl |
| 2 | 4-[(cyclopropylcarbonyl)amino]butyl |
| 2 | 2,3-dihydroxypropyl |
| 2 | 2,2-dimethyl-3-(methylsulfonyl)propyl |
| 2 | 2-fluoro-2-methylpropyl |
| 2 | 2-hydroxy-2-methylpropyl |
| 2 | 2-methylpropyl |
| 2 | 2-methyl-2-({[(1-methylethyl)amino]carbonyl}amino)propyl |
| 2 | 2-{[(1-methylethyl)carbonyl]amino}ethyl |
| 2 | 4-{[(1-methylethyl)carbonyl]amino}butyl |
| 2 | 2-methyl-2-[(methylsulfonyl)amino]propyl |
| 2 | 4-[(methylsulfonyl)amino]butyl |
| 2 | 2-[(methylsulfonyl)amino]ethyl |
| 2 | 4-[(4-morpholinecarbonyl)amino]butyl |
| 2 | 2-[(4-morpholinecarbonyl)amino]ethyl |
| 2 | tetrahydro-2H-pyran-4-ylmethyl |

Cytokine Induction in Human Cells

An in vitro human blood cell system is used to assess cytokine induction. Activity is based on the measurement of interferon (α) and tumor necrosis factor (α) (IFN-α, and TNF-α, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood Fla.) centrifuge frit tubes containing density gradient medium. The PBMC layer is collected and washed twice with DPBS or HBSS and re-suspended at $4\times10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 µM. Controls include cell samples with media only, cell samples with DMSO only (no compound), and cell samples with reference compound.

Incubation

The solution of test compound is added at 60 µM to the first well containing RPMI complete and serial 3 fold dilutions are made in the wells. The PBMC suspension is then added to the wells in an equal volume, bringing the test compound concentrations to the desired range (usually 30-0.014 µM). The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype colorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*" and is noted as not reliably detectable. In subsequent calculations and statistics, "*" is treated as a zero. Second, all, background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (µmolar) is the lowest of the tested compound concentrations that induces a response over a fixed cytokine concentration for the tested cytokine (usually 20 pg/mL for IFN-α and 40 pg/mL for TNF-α). The maximal response (pg/mL) is the maximal response attained in the dose response curve.

Compounds of the invention and close analogs were tested for their ability to induce cytokine biosynthesis using the test method described above. The analogs used are shown in Table 2 below.

TABLE 2

| Analog | Chemical Name | Reference |
|---|---|---|
| 1 | 1-(4-amino-2-ethoxymethyl-1H-imidazo[4,5-c][1,5]naphthyridin-1-yl)-2-methylpropan-2-ol | Example 6 Part E |
| 2 | 1-[4-amino-2-(2-methoxyethyl)-1H-imidazo[4,5-c][1,5]naphthyridin-1-yl]-2-methylpropan-2-ol | Example 7 Part J |

Figure 2:
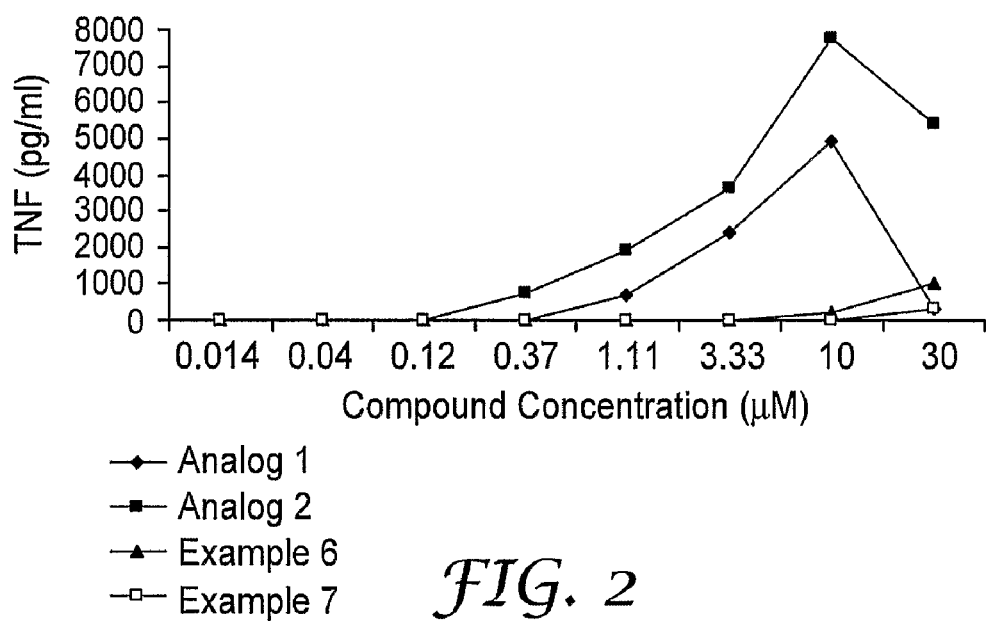
FIG. 2 shows the TNF-α dose response curves (corresponding to values shown in Table 3 below) for Example 6, Example 7, Analog 1, and Analog 2.

The compounds of Examples 6 and 7 and several closely related analogs were tested using the test method described above. The IFN-α dose response curves for Example 6, Example 7, Analog 1, and Analog 2 are shown in FIG. 1. The TNF-α dose response curves for Example 6, Example 7, Analog 1, and Analog 2 are shown in FIG. 2. The minimum effective concentration for the induction of IFN-α, minimum effective concentration for the induction of TNF-α, the maximal response for IFN-α, and the maximal response for TNF-α are shown in Table 3 below where # is the number of separate experiments in which the compound was tested. When a compound was tested in more than one experiment the values shown are the median values.

TABLE 3

| Compound | $R_2$ | Minimum Effective Concentration (µM) | | Maximal Response (pg/mL) | | # |
|---|---|---|---|---|---|---|
| | | IFN | TNF | IFN | TNF | |
| Example 6 | —$CH_2OH$ | 1.11 | 10.0 | 3038 | 684 | 2 |
| Example 7 | —$(CH_2)_2OH$ | 3.33 | 30.0 | 1849 | 342 | 1 |
| Analog 1 | —$CH_2OCH_2CH_3$ | 0.12 | 1.11 | 658 | 4921 | 1 |
| Analog 2 | —$(CH_2)_2OCH_3$ | 0.04 | 0.37 | 4143 | 7762 | 7 |

Compounds of the invention and in some instances, close analogs (Table 5 below), were tested for their ability to induce cytokine biosynthesis using the test method described above. The minimum effective concentration for the induction of IFN-α, minimum effective concentration for the induction of TNF-α, the maximal response for IFN-α, and the maximal response for TNF-α are shown in Table 4 below where # is the number of separate experiments in which the compound was tested. When a compound, was tested in more than one experiment the values shown are the median values.

TABLE 4

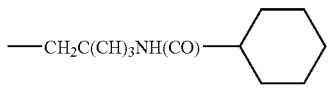

| Compound | $R_1$ | $R_2$ | Minimum Effective Concentration (μM) IFN | Minimum Effective Concentration (μM) TNF | Maximal Response (pg/mL) IFN | Maximal Response (pg/mL) TNF | # |
|---|---|---|---|---|---|---|---|
| Example 6 | —CH$_2$C(CH$_3$)$_2$OH | —CH$_2$OH | 1.11 | 10 | 2290 | 1316 | 3 |
| Example 7 | —CH$_2$C(CH$_3$)$_2$OH | —(CH$_2$)$_2$OH | 3.33 | 30 | 2063 | 331 | 2 |
| Analog 1 | —CH$_2$C(CH$_3$)$_2$OH | —CH$_2$OCH$_2$CH$_3$ | 0.12 | 1.11 | 1674 | 7275 | 2 |
| Analog 2 | —CH$_2$C(CH$_3$)$_2$OH | —(CH$_2$)$_2$OCH$_3$ | 0.04 | 0.37 | 3142 | 7503 | 2 |
| Analog 3 | —CH$_2$C(CH$_3$)$_2$OH | —CH$_3$ | 0.37 | 3.33 | 1952 | 6519 | 1 |
| Analog 4 | —CH$_2$C(CH$_3$)$_2$OH | —CH$_2$CH$_3$ | 0.37 | 3.33 | 2150 | 3863 | 1 |
| Analog 5 | —CH$_2$C(CH$_3$)$_2$OH | —CH$_2$CH$_2$CH$_3$ | 0.12 | 1.11 | 2484 | 5526 | 1 |
| Example 1 | —CH$_2$C(CH)$_3$NH(CO)—〈cyclohexyl〉 | —CH$_2$OH | 1.11 | 10 | 1467 | 798 | 1 |
| Analog 6 | —CH$_2$C(CH)$_3$NH(CO)—〈cyclohexyl〉 | —CH$_2$OCH$_2$CH$_3$ | 0.014 | 0.014 | 1647 | 8691 | 1 |
| Example 2 | —CH$_2$C(CH$_3$)$_2$NHS(O)$_2$CH$_3$ | —CH$_2$OH | 10 | 30 | 1914 | 170 | 1 |
| Analog 7 | —CH$_2$C(CH$_3$)$_2$NHS(O)$_2$CH$_3$ | —CH$_2$OCH$_2$CH$_3$ | 0.04 | 0.37 | 2465 | 9234 | 1 |
| Example 14 | —CH$_2$CF(CH$_3$)$_2$ | —CH$_2$OH | 1.11 | 3.33 | 1833 | 1922 | 1 |
| Example 15 | —CH$_2$CF(CH$_3$)$_2$ | —(CH$_2$)$_2$OH | 1.11 | 10 | 1646 | 84 | 1 |
| Analog 8 | —CH$_2$CF(CH$_3$)$_2$ | —CH$_3$ | 0.37 | 10 | 2120 | 1679 | 2 |
| Example 96 | —CH$_2$CH(CH$_3$)$_2$ | —CH$_2$OH | 1.11 | 30 | 1592 | 363 | 1 |
| Analog 9 | —CH$_2$CH(CH$_3$)$_2$ | —CH$_2$OCH$_2$CH$_3$ | 0.12 | 1.11 | 1524 | 3160 | 2 |
| Analog 10 | —CH$_2$CH(CH$_3$)$_2$ | —CH$_3$ | 0.37 | 1.11 | 1117 | 699 | 12 |
| Example 3 | —(CH$_2$)$_4$NHS(O)$_2$CH$_3$ | —(CH$_2$)$_2$OH | 1.11 | 30 | 3008 | 7 | 2 |
| Example 4 | —(CH$_2$)$_2$NHS(O)$_2$CH$_3$ | —CH$_2$OH | 10 | >30 | 1520 | * | 1 |
| Example 5 | —(CH$_2$)$_2$NHS(O)$_2$CH$_3$ | —(CH$_2$)$_2$OH | 30 | >30 | 49 | * | 1 |

* Below the experimental background of 40 pg/mL

TABLE 5

| Analog | Chemical Name | Reference |
|---|---|---|
| 1 | 1-(4-amino-2-ethoxymethyl-1H-imidazo[4,5-c][1,5]naphthyridin-1-yl)-2-methylpropan-2-ol | Example 6 Part E |
| 2 | 1-[4-amino-2-(2-methoxyethyl)-1H-imidazo[4,5-c][1,5]naphthyridin-1-yl]-2-methylpropan-2-ol | Example 7 Part J |
| 3 | 1-(4-amino-2-methyl-1H-imidazo[4,5-c][1,5]naphthyridin-1-yl)-2-methylpropan-2-ol | U.S. Pat. No. 6,194,425** |
| 4 | 1-(4-amino-2-ethyl-1H-imidazo[4,5-c][1,5]naphthyridin-1-yl)-2-methylpropan-2-ol | U.S. Pat. No. 6,194,425** |
| 5 | 1-(4-amino-2-propyl-1H-imidazo[4,5-c][1,5]naphthyridin-1-yl)-2-methylpropan-2-ol | U.S. Pat. No. 6,194,425** |
| 6 | N-[2-(4-amino-2-ethoxymethyl-1H-imidazo[4,5-c][1,5]naphthyridin-1-yl)-1,1-dimethylethyl]cyclohexanecarboxamide | Example 1 Part H |
| 7 | N-[2-(4-amino-2-ethoxoxymethyl-1H-imidazo[4,5-c][1,5]naphthyridin-1-yl)-1,1-dimethylethyl]methanesulfonamide | Example 2 Part A |
| 8 | 1-(2-fluoro-2-methylpropyl)-2-methyl-1H-imidazo[4,5-c][1,5]naphthyridin-4-amine | U.S. Pat. No. 6,194,425** |
| 9 | 2-ethoxymethyl-1-(2-methylpropyl)-1H-imidazo[4,5-c][1,5]naphthyridin-4-amine | U.S. Pat. No. 6,194,425** |
| 10 | 2-methyl-1-(2-methylpropyl)-1H-imidazo[4,5-c][1,5]naphthyridin-4-amine | U.S. Pat. No. 6,194,425 Example 36 |

**Although not a working example, the compound is readily prepared using the disclosed synthetic methods.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A compound of Formula I:

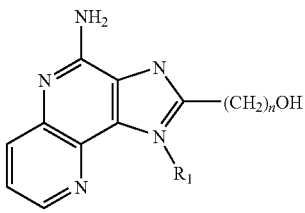

wherein:
n is 1 or 2;
$R_1$ is selected from the group consisting of:
  alkyl, aminoalkyl, dihydroxyalkyl, haloalkyl, hydroxyalkyl, heterocyclylalkylenyl that can be unsubstituted or substituted by one or more $C_{1-4}$ alkyl groups;
  —X—Y—$R_4$, and
  —X—$R_5$;
X is straight chain or branched chain $C_{1-6}$ alkylene which can be optionally interrupted by one —O— group;
Y is
  —N($R_8$)-Q-;
$R_4$ is selected from the group consisting of straight chain or branched chain alkyl, cycloalkyl, aryl, arylalkylenyl, and heteroaryl that is unsubstituted or substituted by methyl, wherein-the aryl and arylalkylenyl groups can be unsubstituted or substituted by a-substituent selected from the group consisting of alkyl halogen hydroxy and cyano;
$R_5$ is selected from the group consisting of

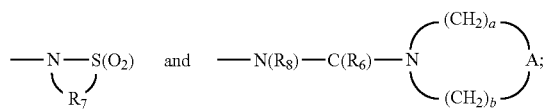

$R_6$ is =O;
$R_7$ is propylene;
$R_8$ is selected from the group consisting of hydrogen and alkyl;
A is —O—;
Q is selected from the group consisting of —C($R_6$)—, —S(O)$_2$, —C($R_6$)—N($R_8$)—, and —S(O)$_2$—N($R_8$); and
a and b are each 2;
or a pharmaceutically acceptable salt thereof.

2. The compound or salt of claim 1 wherein n is 1.
3. The compound or salt of claim 1 wherein n is 2.
4. The compound or salt of claim 1 wherein $R_1$ is selected from the group consisting of alkyl, aminoalkyl, dihydroxyalkyl, haloalkyl, and hydroxyalkyl.

5. The compound or salt of claim 4 wherein $R_1$ is selected from the group consisting of methyl, ethyl, n-propyl, n-butyl, 2-methylpropyl, 2-amino-2-methylpropyl, 3-amino-2,2-dimethylpropyl, 2,3-dihydroxypropyl, 2-fluoro-2-methylpropyl, and 2-hydroxy-2-methylpropyl.

6. The compound or salt of claim 1 wherein $R_1$ is heterocyclylalkylenyl which can be unsubstituted or substituted by one or more $C_{1-4}$ alkyl groups.

7. The compound or salt of claim 6 wherein heterocyclyl is selected from the group consisting of 1,3-dioxolanyl, tetrahydropyranyl, tetrahydrofuranyl, pyrrolidinyl, piperidinyl, and morpholinyl, and alkylenyl is $C_{1-4}$ alkylenyl.

8. The compound or salt of claim 6 wherein $R_1$ is selected from the group consisting of tetrahydro-2H-pyran-4-ylmethyl and (2,2-dimethyl-1,3-dioxolan-4-yl)methyl.

9. The compound or salt of claim 1 wherein $R_1$ is —X—Y—$R_4$ wherein X is straight chain or branched chain $C_{1-6}$ alkylene which may be interrupted by one —O— group; Y is selected from the group consisting of —N($R_8$)—C(O)—, —N($R_8$)—S(O)$_2$—, and —N($R_8$)—C(O)—N($R_8$)—, wherein $R_8$ is selected from hydrogen and methyl; and $R_4$ is selected from the group consisting of $C_{1-6}$ alkyl, isoquinolinyl, N-methylimidazolyl, pyridinyl, quinolinyl, phenyl, and phenyl substituted by a substituent selected from the group consisting of chloro, cyano, fluoro, hydroxy, and methyl.

10. The compound or salt of claim 1 wherein $R_1$ is selected from the group consisting of 2-[(cyclopropylcarbonyl)amino]ethyl, 4-[(cyclopropylcarbonyl)amino]butyl, 2-[(cyclohexylcarbonyl)amino]-2-methylpropyl, 2-{[(1-methylethyl)carbonyl]amino}ethyl, 4-{[(1-methylethyl)carbonyl]amino}butyl, 2-methyl-2-{[(1-methylethyl)carbonyl]amino}propyl, 2-[(methylsulfonyl)amino]ethyl, 4-[(methylsulfonyl)amino]butyl, 2-methyl-2-[(methylsulfonyl)amino]propyl, and 2-methyl-2-({[(1-methylethyl)amino]carbonyl}amino)propyl.

11. The compound or salt of claim 1 wherein $R_1$ is —X—Y—$R_4$ wherein X is straight chain or branched chain $C_{1-6}$ alkylene which may be interrupted by one —O— group; Y is selected from the group consisting of —N($R_8$)—C(O)—, —N($R_8$)—S(O)$_2$—, —N($R_8$)—C(O)—N($R_8$)—, and —N($R_8$)—S(O)$_2$—N($R_8$)—, wherein $R_8$ is selected from hydrogen and methyl; and $R_4$ is selected from the group consisting of $C_{1-6}$ alkyl, aryl, arylalkylenyl, and heteroaryl which is unsubstituted or substituted by methyl, wherein aryl and arylalkyleneyl are unsubstituted or substituted by a substituent selected from the group consisting of chloro, cyano, fluoro, hydroxy, and methyl.

12. The compound or salt of claim 1 wherein $R_1$ is selected from the group consisting of 4-(1,1-dioxidoisothiazolidin-2-yl)butyl, 4-[(4-morpholinecarbonyl)amino]butyl, and 2-[(4-morpholinecarbonyl)amino]ethyl.

13. 2-Hydroxymethyl-1-(2-methylpropyl)-1H-imidazo[4,5-c][1,5]naphthyridin-4-amine or a pharmaceutically acceptable salt thereof.

14. A compound selected from the group consisting of 1-(4-amino-2-hydroxymethyl-1H-imidazo[4,5-c][1,5]naphthyrin-1-yl)-2-methylpropan-2-ol and 1-[4-amino-2-(2-hydroxyethyl)-1H-imidazo[4,5-c][1,5]naphthyrin-1-yl]-2-methylpropan-2-ol, or a pharmaceutically acceptable salt thereof.

15. A compound selected from the group consisting of N-[4-(4-amino-2-hydroxymethyl-1H-imidazo[4,5-c][1,5]naphthyrin-1-yl)butyl]methanesulfonamide and N-{4-[4-amino-2-(2-hydroxyethyl)-1H-imidazo[4,5-c][1,5]naphthyrin-1-yl]butyl]}methane sulfonamide, or a pharmaceutically acceptable salt thereof.

16. A pharmaceutical composition comprising a therapeutically effective amount of a compound or salt of claim 1 and a pharmaceutically acceptable carrier.

17. A method of preferentially inducing the biosynthesis of IFN-α in an animal comprising administering an effective amount of a compound or salt of claim 1 to the animal.

18. The method of claim 17 wherein the compound or salt is administered systemically.

* * * * *